United States Patent
Hogset et al.

(10) Patent No.: US 10,610,582 B2
(45) Date of Patent: Apr. 7, 2020

(54) COMPOUND AND METHOD FOR VACCINATION AND IMMUNISATION

(71) Applicant: PCI Biotech AS, Lysaker (NO)

(72) Inventors: Anders Hogset, Oslo (NO); Pal Johansen, Winterthur (CH)

(73) Assignee: PCI BIOTECH AS, Oslo (NO)

( * ) Notice: Subject to any disclaimer, the term of this patent is extended or adjusted under 35 U.S.C. 154(b) by 0 days.

(21) Appl. No.: 14/914,758

(22) PCT Filed: Aug. 28, 2014

(86) PCT No.: PCT/EP2014/068313
§ 371 (c)(1),
(2) Date: Feb. 26, 2016

(87) PCT Pub. No.: WO2015/028574
PCT Pub. Date: Mar. 5, 2015

(65) Prior Publication Data
US 2016/0206725 A1    Jul. 21, 2016

(30) Foreign Application Priority Data

Aug. 28, 2013 (GB) .................. 1315292.1
Apr. 11, 2014 (GB) .................. 1406597.3

(51) Int. Cl.
| | | |
|---|---|---|
| *A61K 39/39* | (2006.01) | |
| *A61K 39/12* | (2006.01) | |
| *A61K 39/00* | (2006.01) | |
| *A61K 31/437* | (2006.01) | |
| *A61K 31/409* | (2006.01) | |
| *A61K 31/7115* | (2006.01) | |
| *A61K 41/00* | (2020.01) | |
| *A61K 47/69* | (2017.01) | |
| *A61N 5/06* | (2006.01) | |
| *C12N 7/00* | (2006.01) | |
| *A61K 35/74* | (2015.01) | |

(52) U.S. Cl.
CPC ............ *A61K 39/12* (2013.01); *A61K 31/409* (2013.01); *A61K 31/437* (2013.01); *A61K 31/7115* (2013.01); *A61K 39/0011* (2013.01); *A61K 39/39* (2013.01); *A61K 41/00* (2013.01); *A61K 41/0057* (2013.01); *A61K 47/6901* (2017.08); *A61N 5/062* (2013.01); *C12N 7/00* (2013.01); *A61K 35/74* (2013.01); *A61K 2039/5154* (2013.01); *A61K 2039/5156* (2013.01); *A61K 2039/54* (2013.01); *A61K 2039/55511* (2013.01); *A61K 2039/55561* (2013.01); *A61K 2039/55572* (2013.01); *A61K 2039/572* (2013.01); *C12N 2710/20034* (2013.01)

(58) Field of Classification Search
None
See application file for complete search history.

(56) References Cited

U.S. PATENT DOCUMENTS

| | | |
|---|---|---|
| 8,216,587 B1 | 7/2012 | Berg et al. |
| 2002/0022032 A1 | 2/2002 | Curry et al. |
| 2005/0013812 A1* | 1/2005 | Dow .................. A61K 39/02 424/144.1 |
| 2009/0062719 A1* | 3/2009 | Neuberger ......... A61K 41/0071 604/20 |
| 2009/0209508 A1 | 8/2009 | Lange et al. |
| 2010/0129432 A1 | 5/2010 | Chen et al. |
| 2010/0222538 A1 | 9/2010 | Kwon et al. |
| 2012/0087859 A1 | 4/2012 | Tae et al. |
| 2012/0294885 A1 | 11/2012 | David et al. |

FOREIGN PATENT DOCUMENTS

| | | | |
|---|---|---|---|
| GB | 2 420 784 | 6/2006 | |
| NZ | 514228 | 1/2004 | |
| WO | 96/07432 | 3/1996 | |
| WO | 00/54802 | 9/2000 | |
| WO | WO 0054802 A2 * | 9/2000 | ......... A61K 39/0011 |
| WO | 02/44395 | 6/2002 | |
| WO | 02/44396 | 6/2002 | |
| WO | 03/020309 | 3/2003 | |
| WO | 2007/133728 | 11/2007 | |
| WO | 2008/007073 | 1/2008 | |

(Continued)

OTHER PUBLICATIONS

Wesch et al. 2011 (Modulation of gd T cell responses by TLR ligands, Cell Mol Life Sci 68:2357-2370).*
Verdurmen et al. 2011 (Biological responses towards cationic peptides and drug carriers, Trends in Pharmacological Sciences 32(2):116-124.*
Kornbluth et al. 2006 (Immunostimulatory combination: designing the next generation of vaccine adjuvants; Journal of Leukocyte Biology 80: 1084).*
Cheng et al. 2010 (Anticancer function of polyinosinic-polycytidylic acid; Cancer Biology & Therapy 10:12: 1219-1223).*
Berg et al. 2011 (Disulfonated tetraphenyl chlorin (TPCS2a), a novel photosensitizer developed for clinical utilization of photochemical internalization; Photochemical and Photobiological Sciences 10: 1637 (Year: 2011).*

(Continued)

*Primary Examiner* — Mary Maille Lyons
(74) *Attorney, Agent, or Firm* — Wenderoth, Lind & Ponack, L.L.P.

(57) ABSTRACT

A method of vaccination or immunisation involving the use of a photosensitizing agent, an antigenic molecule, e.g. a vaccine component, and an agent which enhances the effect of photochemical internalization (PCI)-mediated vaccination is disclosed wherein the agent is a ligand for a Toll-like receptor (TLR), and irradiation is with light of a wavelength effective to activate the photosensitizing agent. Antigenic, e.g. vaccine compositions, useful in such a method are also disclosed along with a method of generating antigen presenting cells which may be used to generate an immune response based on introducing antigenic molecules, e.g. vaccine components, into cells to achieve antigen presentation. The invention also provides methods of achieving vaccination in a subject using such cells.

23 Claims, 22 Drawing Sheets

Specification includes a Sequence Listing.

(56) References Cited

FOREIGN PATENT DOCUMENTS

| WO | WO 2008007073 A2 * | 1/2008 | ....... A61K 47/48969 |
|---|---|---|---|
| WO | 2009/077908 | 6/2009 | |
| WO | 2009/118296 | 10/2009 | |
| WO | 2010/143942 | 12/2010 | |
| WO | 2011/018635 | 2/2011 | |
| WO | 2011/018636 | 2/2011 | |
| WO | WO 2011018635 A2 * | 2/2011 | ......... A61K 41/0071 |
| WO | WO 2011018636 A2 * | 2/2011 | ........... A61K 9/0014 |
| WO | 2013/106852 | 7/2013 | |
| WO | 2014/139597 | 9/2014 | |
| WO | 2015/154832 | 10/2015 | |

OTHER PUBLICATIONS

Norum et al. 2009 (Photochemical internalization (PCI) in cancer therapy: from bench towards bedside medicine; J or Photochem Photobio B: Biology 96:83-92) (Year: 2009).*

Martinez de Pinillos Bayona et al. 2015 Enhancing the efficacy of cytotoxic agents for cancer therapy using Photochemical Internalisation; International Journal of Cancer; DOI: 10.1002/ijc.29510/abstract;jsessionid=BEC17FA0039AABE351DA6C02CB638B2D.f02t03 • Source: PubMed (Year: 2015).*

Baglo et al.; Enhanced Efficacy of Bleomycin in Bladder Cancer Cells by Photochemical Internalization; BioMed Research International; vol. 77; No. 3; 2014; pp. 759-10.

Folini et al.; Photochemical Internalization of Peptide Nucleic Acid Targeting the Catalytic Subunit of Human Telomerase; Cancer Research; vol. 63; No. 13; 2003; pp. 3490-3494.

Selbo et al.; Photochemical Internalization of Therapeutic Macromolecular Agents; A Novel Strategy to Kill Multidrug-Resistant Cancer Cells; Journal of Pharmacology and Experimental Therapeutics; vol. 319; No. 2; 2006; pp. 604-612.

Selbo et al.; Multi-Modality Therapeutics with Potent Anti-Tumor Effects; Photochemical Internalization Enhances Delivery of the Fusion Toxin scFvMEL/rGel; PLOS One; vol. 4; No. 8; Aug. 19, 2009; e6691; pp. 1-10.

Stratford et al.; Photochemical Internalization of CD133-Targeting Immunotoxins Efficiently Depletes Sarcoma Cells with Stem-Like Properties and Reduces Tumorigenicity; Biochimica et Biophysica Acta; vol. 1830; No. 8; 2013; pp. 4235-4243.

Razonable et al.; Stimulation of Toll-Like Receptor 2 with Bleomycin Results in Cellular Activation and Secretion of Pro-Inflammatory Cytokines and Chemokines; Toxicology and Applied Pharmacology; vol. 210; No. 3; 2006; pp. 181-189.

Raemdonck et al.; Prolonged Gene Silencing by Combining siRNA Nanogels and Photochemical Internalization; Journal of Controlled Release; vol. 145, No. 3; 2010; pp. 281-288.

Berg et al.; Disulfonated Tetraphenyl Chlorin (TPC2a), a Novel Photosensitizer Developed for Clinical Utilization of Photochemical Internalization; Photochemical & Photobiological Sciences; vol. 10; 2011; pp. 1637-1651.

International Search Report dated Jan. 8, 2015 in Application No. PCT/EP2014/068313.

Search Report dated Apr. 29, 2014 in counterpart United Kingdom Application No. GB1315292.1.

Week et al.; "TLR ligands differentially affect uptake and presentation of cellular antigens"; Blood; vol. 109; No. 9; 2007; pp. 3890-3894.

First Examination Report dated Sep. 9, 2014 in counterpart New Zealand Application No. 629644.

Belyakov et al.; "Mucosal immunization with HIV-1 peptide vaccine induces mucosal and systemic cytotoxic T lymphocytes and protective immunity in mice against intrarectal recombinant HIV-vaccinia challenge" Proceedings of National Academy of Sciences of the USA; vol. 95; No. 4; 1998; pp. 1709-1714.

Berg et al.; "Lysosomes and Microtubules as Targets for Photochemotherapy of Cancer"; Photochemistry and Photobiology; vol. 65; No. 3; 1997; pp. 403-409.

Casal et al.; "Peptide Vaccine against Canine Parvovirus: Identification of Two Neutralization Subsites in the N Terminus of VP2 and Optimization of the Amino Acid Sequence"; Journal of Virology; vol. 69; No. 11; 1995; pp. 7274-7277.

Germain; "MHC-Dependent Antigen Processing and Peptide PResentation: Providing Ligands for T Lymphocyte Activation"; Cell; vol. 76; No. 2; 1994; pp. 287-299.

Hodi; "Well-Defined Melanoma Antigens as Progression Markers for Melanoma: Insights into Differential Expression and Host Response Based on Stage"; Clinical Cancer Research; vol. 12; No. 3; 2006; pp. 673-678.

Itoh et al.; "A synthetic peptide vaccine invloving the product of the pre-S(2) region of hepatitis B virus DNA: Protective efficacy in chimpanzees"; Proceedings of the National Academy of Sciences of the USA; vol. 83; No. 23; 1986; pp. 9174-9178.

Kabeya et al.; "An effective peptide vaccine to eliminate bovine leukaemia virus (BVL) infected cells in carrier sheep" Vaccine; vol. 14; No. 12; 1996; pp. 1118-1122.

Ma et al.; "HPV and Therapeutic Vaccines: Where are We in 2010?"; Current Cancer Therapy Reviews; vol. 6; 2010; pp. 81-103.

Naruse et al.; "A potential peptide vaccine against two different strains of influenza virus isolated at intervals of about 10 years"; Proceedings of the National Academy of Sciences of the USA; vol. 91; No. 20; 1994; pp. 9588-9592.

Phanuphak et al.; "International clinical trials of HIV vaccines: I. Phase I trial of an HIV-1 synthetic peptide vaccine in Bangkok, Thailand"; Asian Pacific Journal of Allergy and Immunology; vol. 15; 1997; pp. 41-48.

Renkvist et al.; "A listing of human tumor antigens recognized by T cells"; Cancer Immunology, Immunotherapy; vol. 50; 2001; pp. 3-15.

Rock; "A new foreign policy: MHC class I molecules monitor the outside world"; Immunology Today; vol. 17; No. 13; 1996; pp. 131-137.

Rosenberg et al.; "Immunologic abd therapeutic evaluation of a synthetic peptide vaccine for the treatment of patients with metastatic melanoma"; Nature Medicine; vol. 4; No. 3; 1998; pp. 321-327.

Schirrmacher; "Biotherapy of cancer: Perspectives of immunotherapy and gene therapy"; Journal of Cancer Research and Clinical Oncology; vol. 121; 1995; pp. 443-451.

Wilson et al.; "Results of a phase I clincal trial of a T-cell receptor peptide vaccine in patients with multiple sclerosis. I. Analysis of T-cell receptor utilization in CSF cell populations"; Journal of Neuroimmunology; vol. 76; 1997; pp. 15-28.

Yewdell et al.; "Cell Biology of Antigen Processing and Presentation to Major Histocompatibility Complex Class I Molecule-Restricted T Lymphocytes"; Advances in Immunology; vol. 52; 1992; pp. 1-123.

Benediktsdottir et al.; "Scientific and Technological Aspects of Industrially Important Polysaccharides"; Carbohydrate Polymers; vol. 86; 2011; pp. 1451-1460.

Lee et al.; "Tumor-homing photosensitizer-conjugated glycol chitosan nanoparticles for synchronous photodynamic imaging and therapy based on cellular on/off system"; Biomaterials; vol. 32; 2011; pp. 4021-4029.

Lee et al.; "Comparative Study of Photosensitizer Loaded and Conjugated Glycol Chitosan Nanoparticles for Cancer Therapy" Journal of Controlled Release; vol. 152; 2011; pp. 21-29.

Park et al.; "Targeted delivery of low molecular drugs using chitosan and its derivatives"; Advanced Drug Delivery Reviews; vol. 62; 2010; pp. 28-41.

Rúmarsson et al.; "Antibacterial activity of N-quaternary chitosan derivatives: Synthesis, characterization and structure activity relationship (SAR) investigations"; European Polymer Journal; vol. 46; 2010; pp. 1251-1267.

Rúmarsson et al.; "tert-Butyldimethylsilyl O-protected chitosan and chitooligosaccharides: useful precursors for N-modifications in common organic solvents"; Carbohydrate Research; vol. 343; 2008; pp. 2576-2582.

Song et al.; "Functionalized superhydrophobic biomimetic chitosan-based films"; Carbohydrate Polymers; vol. 81; 2010; pp. 140-144.

(56) References Cited

OTHER PUBLICATIONS

Waeckerle-Men et al.; "Photochemical targeting of antigens to the cytosol for stimulation of MHC class-I-restricted T-cell responses"; European Journal of Pharmaceutics and Biopharmaceutics; vol. 85; 2013; pp. 34-41.

Zaharoff et al.; "Chitosan solution enhances both humoral and cell-mediated immune responses to subcutaneous vaccination"; Vaccine; vol. 25; 2007; pp. 2085-2094.

Zaharoff et al.; "Intravesical Immunotherapy of Superficial Bladder Cancer with Chitosan/Interleukin-12"; Cancer Research; vol. 69; No. 15; 2009; pp. 6192-6199.

Håkerud et al.; "Intradermal photosensitisation facilities stimulation of MHC class-I restricted CD8 T-cell responses of co-administered antigen"; Journal of Controlled Release; vol. 174; 2014; pp. 143-150.

Steinhagen et al., "TLR-Based Immune Adjuvants", Vaccine, 29(17): 3341-3355 (2011).

Liu et al., "Therapeutic implications of the TLR and VDR partnership", Trends in Molecular Medicine, 13(3): 117-124 (2007).

O'Neill et al., "Therapeutic Targeting of Toll-Like Receptors for Infections and Inflammatory Diseases and Cancer", Pharmacological Reviews, 61(2): 177-197 (2009).

* cited by examiner

A

B

Scheme 4

A

B

Compound 26 is a mixture of inseparable isomers. Here and onwards only one of the possible isomers is shown.

28
TPC-CO-pip

Scheme 5A

Scheme 5B

SEQUENCE LISTING

<160> NUMBER OF SEQ ID NOS: 11

<210> SEQ ID NO 1
<211> LENGTH: 35
<212> TYPE: PRT
<213> ORGANISM: Human papillomavirus type 16

<400> SEQUENCE: 1

Gly Gln Ala Glu Pro Asp Arg Ala His Tyr Asn Ile Val Thr Phe Cys
1               5                   10                  15

Cys Lys Cys Asp Ser Thr Leu Arg Leu Cys Val Gln Ser Thr His Val
            20                  25                  30

Asp Ile Arg
        35

<210> SEQ ID NO 2
<211> LENGTH: 9
<212> TYPE: PRT
<213> ORGANISM: Human papillomavirus type 16

<400> SEQUENCE: 2

Arg Ala His Tyr Asn Ile Val Thr Phe
1               5

<210> SEQ ID NO 3
<211> LENGTH: 10
<212> TYPE: PRT
<213> ORGANISM: Artificial Sequence
<220> FEATURE:
<223> OTHER INFORMATION: Synthetic lipoprotein derived from Mycoplasma
      salivarium

<400> SEQUENCE: 3

Cys Gly Asp Pro Lys His Pro Lys Ser Phe
1               5                   10

<210> SEQ ID NO 4
<211> LENGTH: 20
<212> TYPE: DNA
<213> ORGANISM: Artificial Sequence
<220> FEATURE:
<223> OTHER INFORMATION: Type B unmethylated CpG oligonucleotide (ODN)
      1826

<400> SEQUENCE: 4
tccatgacgt tcctgacgtt                                              20

<210> SEQ ID NO 5
<211> LENGTH: 22
<212> TYPE: DNA
<213> ORGANISM: Artificial Sequence
<220> FEATURE:
<223> OTHER INFORMATION: Type C unmethylated CpG oligonucleotide (ODN)
      2395

<400> SEQUENCE: 5
tcgtcgtttt cggcgcgcgc cg                                           22

<210> SEQ ID NO 6
<211> LENGTH: 12
<212> TYPE: DNA
<213> ORGANISM: Artificial Sequence
<220> FEATURE:
<223> OTHER INFORMATION: Palindromic sequence

<400> SEQUENCE: 6

```
cggcgcgcgc cg                                                            12

<210> SEQ ID NO 7
<211> LENGTH: 10
<212> TYPE: DNA
<213> ORGANISM: Artificial Sequence
<220> FEATURE:
<223> OTHER INFORMATION: Bacterial ribosomal RNA sequence

<400> SEQUENCE: 7
cggaaagacc                                                               10

<210> SEQ ID NO 8
<211> LENGTH: 19
<212> TYPE: RNA
<213> ORGANISM: Artificial Sequence
<220> FEATURE:
<223> OTHER INFORMATION: TLR13 ligand

<400> SEQUENCE: 8
ggacggaaag accccgugg                                                     19

<210> SEQ ID NO 9
<211> LENGTH: 8
<212> TYPE: PRT
<213> ORGANISM: Artificial Sequence
<220> FEATURE:
<223> OTHER INFORMATION: Ovalbumin antigenic peptide

<400> SEQUENCE: 9

Ser Ile Ile Asn Phe Glu Lys Leu
1               5

<210> SEQ ID NO 10
<211> LENGTH: 9
<212> TYPE: PRT
<213> ORGANISM: Artificial Sequence
<220> FEATURE:
<223> OTHER INFORMATION: TRP-2 epitope

<400> SEQUENCE: 10

Ser Val Tyr Asp Phe Phe Val Trp Leu
1               5

<210> SEQ ID NO 11
<211> LENGTH: 9
<212> TYPE: PRT
<213> ORGANISM: Artificial Sequence
<220> FEATURE:
<223> OTHER INFORMATION: gp100 epitope

<400> SEQUENCE: 11

Lys Val Pro Arg Asn Gln Asp Trp Leu
1               5
```

COMPOUND AND METHOD FOR VACCINATION AND IMMUNISATION

The present invention relates to a method of vaccination or immunisation involving the use of a photosensitizing agent, an antigenic molecule, e.g. a vaccine component, and an agent which enhances the effect of photochemical internalization (PCI)-mediated vaccination wherein the agent is a ligand for a Toll-like receptor (TLR) as defined herein, and irradiation with light of a wavelength effective to activate the photosensitizing agent. The invention also relates to antigenic, e.g. vaccine compositions, useful in such a method. The invention also provides a method of generating antigen presenting cells which may be used to generate an immune response, e.g. for vaccination, which involves using the same components as above to introduce antigenic molecules, e.g. vaccine components, into cells to achieve antigen presentation, and to antigenic compositions useful in such a method. The invention also provides use of cells generated in vitro by such methods for administration to a patient in vivo to elicit an immune response, e.g. to achieve vaccination. A method of internalising an antigenic molecule into a cell is also provided.

Vaccination involves administration of antigenic molecules to provoke the immune system to stimulate development of an adaptive immunity to a pathogen. Vaccines can prevent or improve morbidity from infection. Vaccination is the most effective method of preventing infectious diseases, and widespread immunity due to vaccination is largely responsible for the worldwide eradication of smallpox and the restriction of diseases such as polio, measles, and tetanus from much of the world.

The active agent of a vaccine may be intact but inactivated (non-infective) or attenuated (with reduced infectivity) forms of the causative pathogens, or purified components of the pathogen that have been found to be immunogenic (e.g., outer coat proteins of a virus). Toxoids are produced for immunization against toxin-based diseases, such as the modification of tetanospasmin toxin of tetanus to remove its toxic effect but retain its immunogenic effect.

Since most vaccines are taken up by antigen presenting cells through endocytosis and transported via endosomes to lysosomes for antigen digestion and presentation via the MHC class-II pathway, vaccination primarily activates CD4 T-helper cells and B cells. To combat disorders or diseases such as cancer, as well as intracellular infections, the stimulation of cytotoxic CD8 T-cell responses is important. However, the induction of cytotoxic CD8 T cells usually fails due to the difficulty in delivering antigen to the cytosol and to the MHC class-I pathway of antigen presentation. Photochemical internalisation (PCI) improves delivery of molecules into the cytosol and methods of vaccination which employ PCI are known. PCI is a technique which uses a photosensitizing agent, in combination with an irradiation step to activate that agent, and is known to achieve release of molecules co-administered to a cell into the cell's cytosol. This technique allows molecules that are taken up by the cell into organelles, such as endosomes, to be released from these organelles into the cytosol, following irradiation. PCI provides a mechanism for introducing otherwise membrane-impermeable (or poorly permeable) molecules into the cytosol of a cell in a manner which does not result in widespread cell destruction or cell death.

The basic method of photochemical internalisation (PCI), is described in WO 96/07432 and WO 00/54802, which are incorporated herein by reference. In such methods, the molecule to be internalised (which in the present invention would be the antigenic molecule), and a photosensitizing agent are brought into contact with a cell. The photosensitizing agent and the molecule to be internalised are taken up into a cellular membrane-bound subcompartment within the cell, i.e. they are endocytosed into an intracellular vesicle (e.g. a lysosome or endosome). On exposure of the cell to light of the appropriate wavelength, the photosensitizing agent is activated which directly or indirectly generates reactive species which disrupt the intracellular vesicle's membranes. This allows the internalized molecule to be released into the cytosol.

It was found that in such a method the functionality or the viability of the majority of the cells was not deleteriously affected. Thus, the utility of such a method, termed "photochemical internalisation" was proposed for transporting a variety of different molecules, including therapeutic agents, into the cytosol i.e. into the interior of a cell.

WO 00/54802 utilises such a general method to present or express transfer molecules on a cell surface. Thus, following transport and release of a molecule into the cell cytosol, it (or a part of that molecule) may be transported to the surface of the cell where it may be presented on the outside of the cell i.e. on the cell surface. Such a method has particular utility in the field of vaccination, where vaccine components i.e. antigens or immunogens, may be introduced to a cell for presentation on the surface of that cell, in order to induce, facilitate or augment an immune response.

Whilst vaccination has achieved some noteworthy successes, there remains a need for alternative and improved vaccination methods. The present invention addresses this need.

The present inventors have surprisingly found that, advantageously, a method involving the use of a photosensitizing agent, an antigenic molecule, e.g. a vaccine component, and a TLR ligand as defined herein, and irradiation with light of a wavelength effective to activate the photosensitizing agent results in improved vaccination or an improved immune response.

As will be described in more detail in the Examples below, it has been demonstrated that the method of the invention results in improved vaccination or an improved immune response, e.g. production of an increased amount of antigen-specific T cells. For example, FIG. 1 demonstrates that in vivo vaccination of mice using an antigen, TLR ligands (either a CpG oligonucleotide or an imidazoquinoline), a photosensitiser and irradiation with light of a wavelength effective to activate the photosensitiser led to a significantly increased percentage of antigen-specific T cells in the blood and spleen of said mice, compared with treatment with the antigen and photosensitiser/light irradiation alone. Synergistic effects are also demonstrated in the present Examples in vivo with a range of other TLR ligands, for example poly(IC), imiquimod and MPLA Thus, the present inventors have demonstrated that synergistic improvements of the immune response can be achieved in vivo using a range of TLR ligands in the method of the invention.

Whilst not wishing to be bound by theory, it is believed that the methods of the invention result in increased antigen presentation on MHC Class I molecules leading to an increased CD8+ T cell responses and hence improved vaccination methods. As discussed below, some of the present Examples utilise a model system of OT-1 cells, which is used for assessing MHC class I presentation (see e.g. Delamarre et al. J. Exp. Med. 198:111-122, 2003). In this model system MHC class I presentation of the antigen epitope SIINFEKL (SEQ ID NO:9) leads to activation of the OT-1 T-cells, and the activation can be measured as an increase in proliferation of the antigen-specific T-cells or increased production of IFNγ or IL-2. The results with the methods of the present invention show increased numbers of antigen-specific T cells, and increased IL-2 and IFNγ production by the T cells, which is correlated with increased or improved antigen presentation.

Thus, in a first aspect the present invention provides a method of expressing an antigenic molecule or a part thereof on the surface of a cell, comprising contacting said cell with said antigenic molecule, a photosensitizing agent, and a TLR ligand, and irradiating the cell with light of a wavelength effective to activate the photosensitising agent, wherein said antigenic molecule is released into the cytosol of the cell and the antigenic molecule or a part thereof is subsequently presented on the cell's surface.

Preferably this method (and subsequently described methods) employ only the above described three active ingredients (agents) in said method and the agents are present at appropriate levels (e.g. at the minimum levels described below) in the methods such that they affect the efficacy of the method (i.e. have an active role in enhancing PCI vaccination/antigen presentation/immune response stimulation). Thus preferably the agents are present in buffers with no other active ingredients.

In such methods said antigenic molecule and said photosensitizing agent, and optionally said TLR ligand as defined herein, are each taken up into an intracellular vesicle; and when the cell is irradiated the membrane of the intracellular vesicle is disrupted releasing the antigenic molecule into the cytosol of the cell.

The various agents may be taken up into the same or a different intracellular vesicle relative to each other. It has been found that active species produced by photosensitizers may extend beyond the vesicle in which they are contained and/or that vesicles may coalesce allowing the contents of a vesicle to be released by coalescing with a disrupted vesicle. As referred to herein "taken up" signifies that the molecule taken up is wholly contained within the vesicle. The intracellular vesicle is bounded by membranes and may be any such vesicle resulting after endocytosis, e.g. an endosome or lysosome.

As used herein, a "disrupted" compartment refers to destruction of the integrity of the membrane of that compartment either permanently or temporarily, sufficient to allow release of the antigenic molecule contained within it.

A "photosensitizing agent" as referred to herein is a compound that is capable of translating the energy of absorbed light into chemical reactions when the agent is activated on illumination at an appropriate wavelength and intensity to generate an activated species. The highly reactive end products of these processes can result in cyto- and vascular toxicity. Conveniently such a photosensitizing agent may be one which localises to intracellular compartments, particularly endosomes or lysosomes.

Photosensitisers may exert their effects by a variety of mechanisms, directly or indirectly. Thus for example, certain photosensitisers become directly toxic when activated by light, whereas others act to generate toxic species, e.g. oxidising agents such as singlet oxygen or other reactive oxygen species, which are extremely destructive to cellular material and biomolecules such as lipids, proteins and nucleic acids.

A range of such photosensitizing agents are known in the art and are described in the literature, including in WO96/07432, which is incorporated herein by reference, and may be used in method of the invention. There are many known photosensitising agents, including porphyrins, phthalocyanines, purpurins, chlorins, benzoporphyrins, lysomotropic weak bases, naphthalocyanines, cationic dyes and tetracyclines or derivatives thereof (Berg et al., (1997), J. Photochemistry and Photobiology, 65, 403-409). Other photosensitising agents include texaphyrins, pheophorbides, porphycenes, bacteriochlorins, ketochlorins, hematoporphyrin derivatives, and endogenous photosensitizers induced by 5-aminolevulinic acid and derivatives thereof, Photofrin, dimers or other conjugates between photosensitizers.

Porphyrins are the most extensively studied photosensitising agents. Their molecular structure includes four pyrrole rings linked together via methine bridges. They are natural compounds which are often capable of forming metal-complexes. For example in the case of the oxygen transport protein hemoglobin, an iron atom is introduced into the porphyrin core of heme B.

Chlorins are large heterocyclic aromatic rings consisting, at the core, of three pyrroles and one pyrroline coupled through four methine linkages. Unlike porphyrin, a chlorin is therefore largely aromatic, but not aromatic through the entire circumference of the ring.

The skilled man will appreciate which photosensitisers are suitable for use in the present invention. Particularly preferred are photosensitizing agents which locate to endosome or lysosomes of cells. Thus, the photosensitizing agent is preferably an agent which is taken up into the internal compartments of lysosomes or endosomes. Preferably the photosensitizing agent is taken up into intracellular compartments by endocytosis. Preferred photosensitisers are di- and tetrasulfonated aluminium phthalocyanine (e.g. $AlPcS_{2a}$), sulfonated tetraphenylporphines ($TPPS_n$), sulfonated tetraphenyl bacteriochlorins (e.g. $TPBS_{2a}$), nile blue, chlorin $e_6$ derivatives, uroporphyrin I, phylloerythrin, hematoporphyrin and methylene blue. Further appropriate photosensitizers for use in the invention are described in WO03/020309, which is also incorporated herein by reference, namely sulfonated meso-tetraphenyl chlorins, preferably $TPCS_{2a}$. Preferred photosensitizing agents are amphiphilic photosensitizers (e.g. disulfonated photosensitizers) such as amphiphilic phthalocyanines, porphyrins, chlorins and/or bacteriochlorins, and in particular include $TPPS_{2a}$ (tetraphenylporphine disulfonate), $AlPcS_{2a}$ (aluminium phthalocyanine disulfonate), $TPCS_{2a}$ (tetraphenyl chlorin disulfonate) and $TPBS_{2a}$ (tetraphenyl bacteriochlorin disulfonate), or pharmaceutically acceptable salts thereof. Also preferred are hydrophilic photosensitizing agents, for example $TPPS_4$ (meso-tetraphenylporphine tetrasulfonate). Particularly preferred photosensitizing agents are sulfonated aluminium phthalocyanines, sulfonated tetraphenylporphines, sulfonated tetraphenylchlorins and sulfonated tetraphenylbacteriochlorins, preferably $TPCS_{2a}$, $AlPcS_{2a}$, $TPPS_4$ and $TPBS_{2a}$. In a particularly preferred embodiment of the present invention the photosensitizing agent is the chlorin $TPCS_{2a}$ (Disulfonated tetraphenyl chlorin, e.g. Amphinex®).

A photosensitiser may be linked to a carrier to provide the photosensitising agent. Thus, in a preferred aspect of this embodiment of the invention the photosensitising agent is a conjugate of a photosensitiser and chitosan as defined in formula (I):

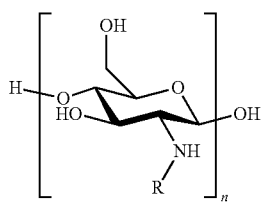
(I)

wherein n is an integer greater than or equal to 3;

R appears n times in said compound, and in 0.1%-99.9% (preferably 0.5%-99.5%) of said total Rn groups, each R is a group A selected from:

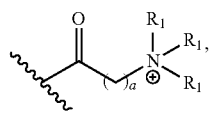

wherein each $R_1$, which may be the same or different, is selected from H, $CH_3$ and —$(CH_2)_b$—$CH_3$; a is 1, 2, 3, 4 or 5; and b is 0, 1, 2, 3, 4 or 5 (in which the counter-ion may be, for example, $Cl^-$); preferably $R_1$, is $CH_3$ and b is 1, and

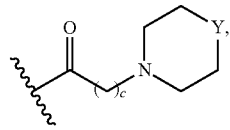

wherein Y is O; S; $SO_2$, —$NCH_3$, or —$N(CH_2)_d CH_3$; c=1, 2, 3, 4 or 5; and d=1, 2, 3, 4 or 5, preferably Y is $NCH_3$ and c is 1, wherein each R group may be the same or different, and in 0.1%-99.9% (preferably 0.5%-99.5%) of said total Rn groups, each R is a group B selected from:

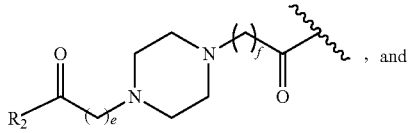, and

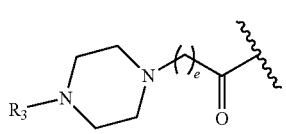

wherein e is 0, 1, 2, 3, 4 or 5; and f is 1, 2, 3, 4 or 5; preferably e and f=1, $R_2$ is a group selected from:

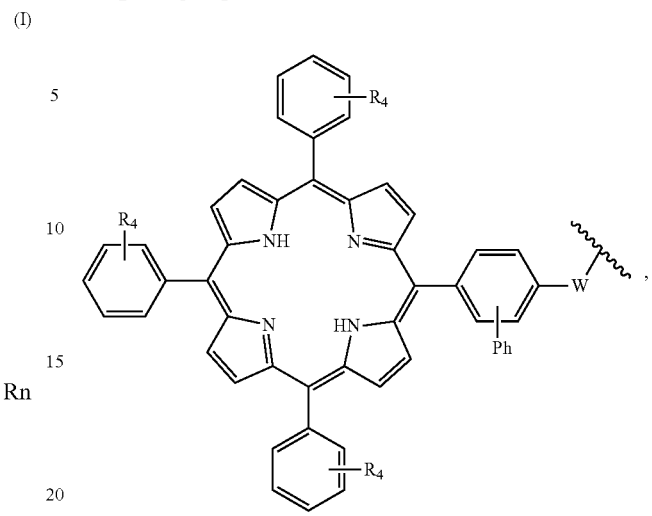

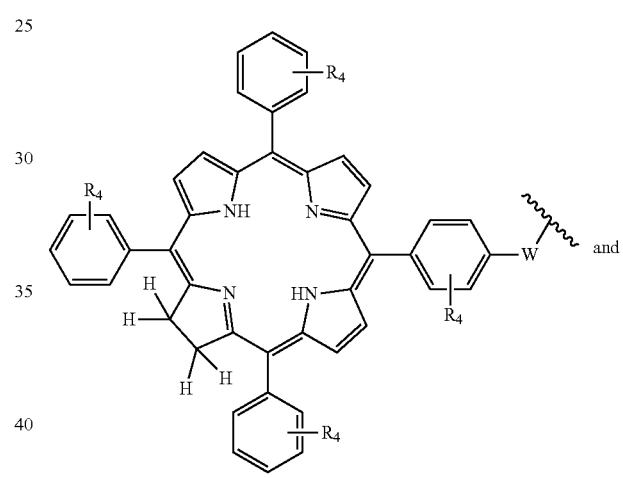 and

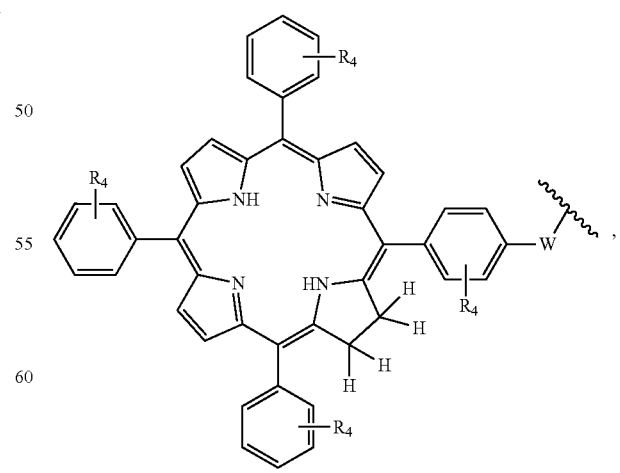,

W is a group selected from O, S, NH or $N(CH_3)$; preferably NH, $R_3$ is a group selected from:

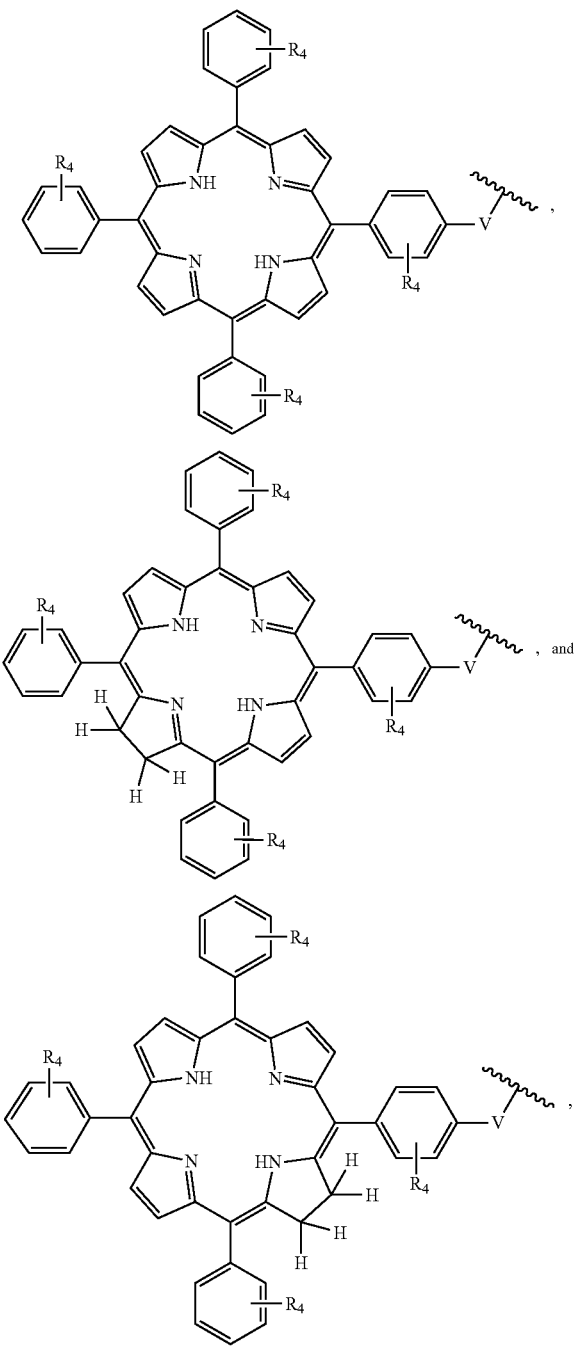

V is a group selected from CO, SO₂, PO, PO₂H or CH₂; preferably CO, and $R_4$ is a group (substituted in the o, m or p position), which may be the same or different, selected from H, —OH, —OCH₃, —CH₃, —COCH₃, C(CH₃)₄, —NH₂, —NHCH₃, —N(CH₃)₂ and —NCOCH₃, preferably H, wherein each R group may be the same or different.

The chitosan polymer has at least 3 units (n=3). However, preferably n is at least 10, 20, 50, 100, 500, 1000 e.g. from 10 to 100 or 10 to 50.

In a preferred embodiment $R_2$ is selected from

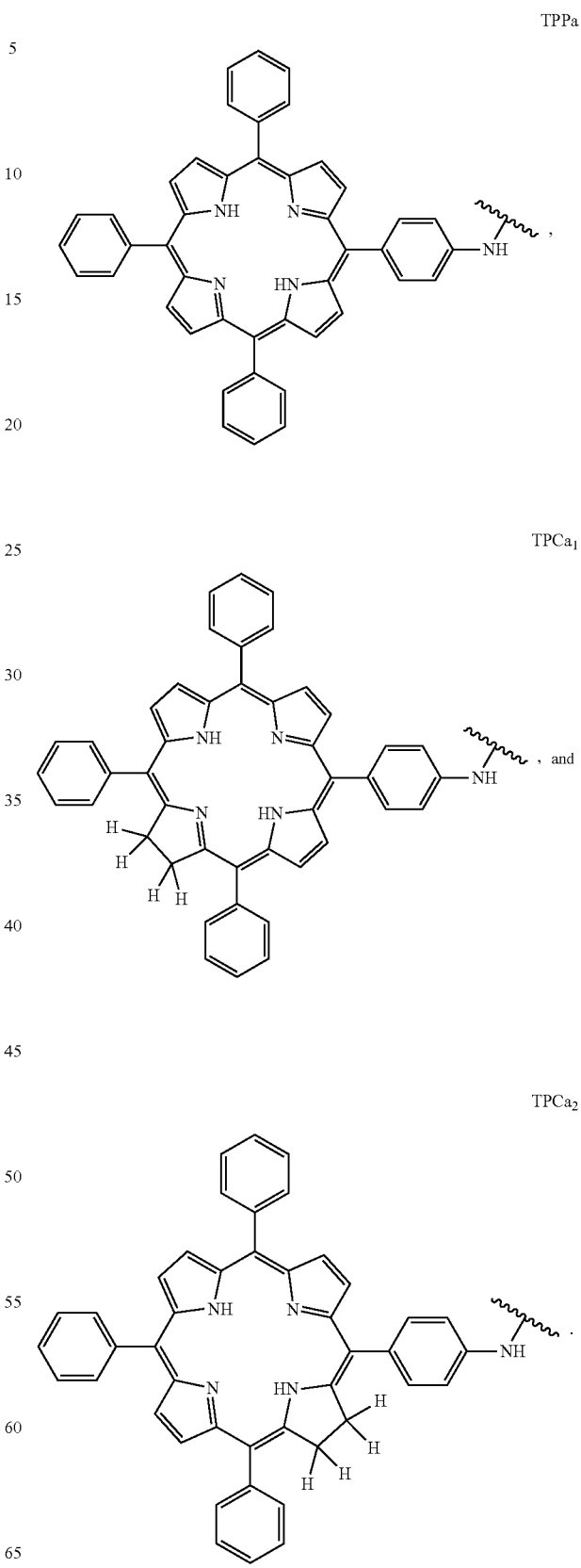

In a further preferred embodiment $R_3$ is selected from
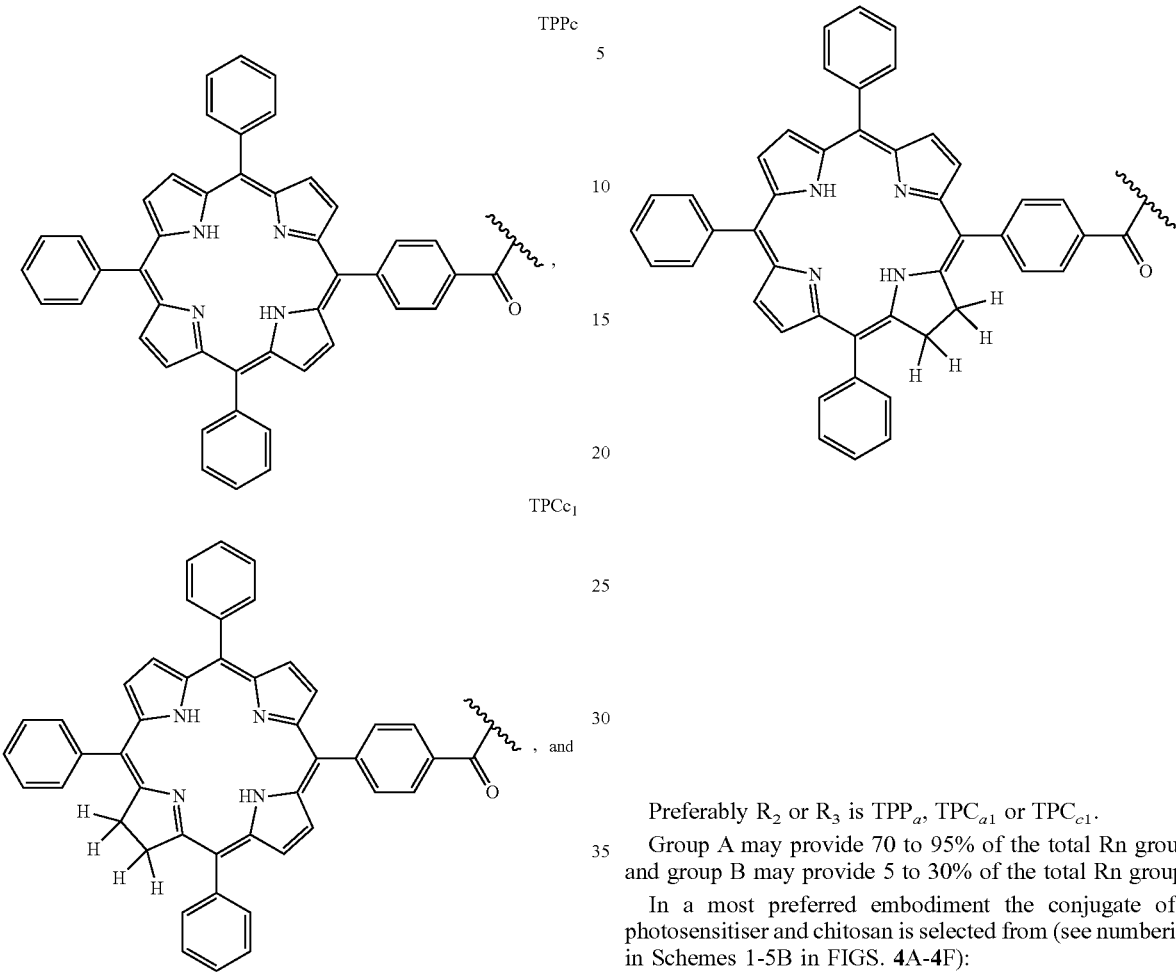
Preferably $R_2$ or $R_3$ is $TPP_a$, $TPC_{a1}$ or $TPC_{c1}$.
Group A may provide 70 to 95% of the total Rn groups and group B may provide 5 to 30% of the total Rn groups.
In a most preferred embodiment the conjugate of a photosensitiser and chitosan is selected from (see numbering in Schemes 1-5B in FIGS. 4A-4F):
17: B:25%, A:75%
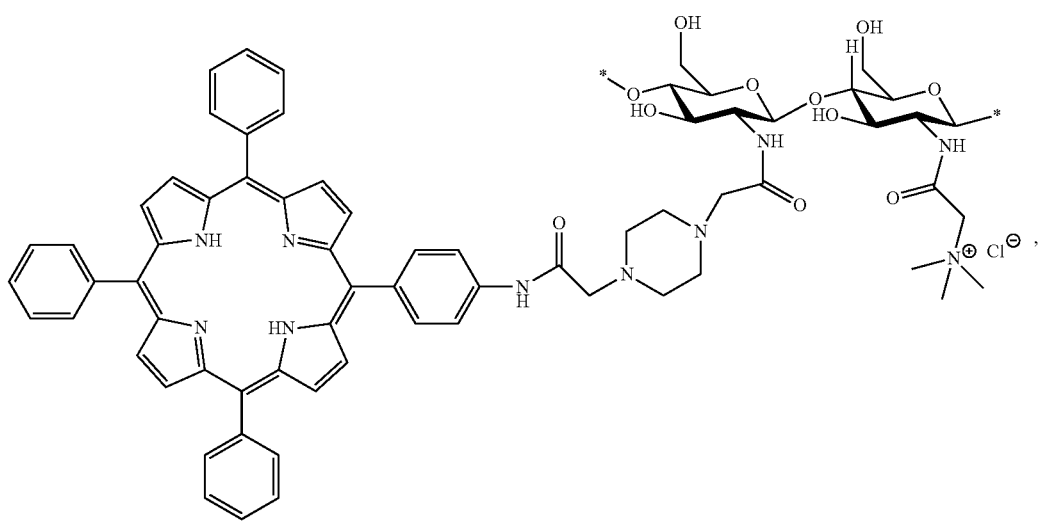

19: B:25%, A:75%
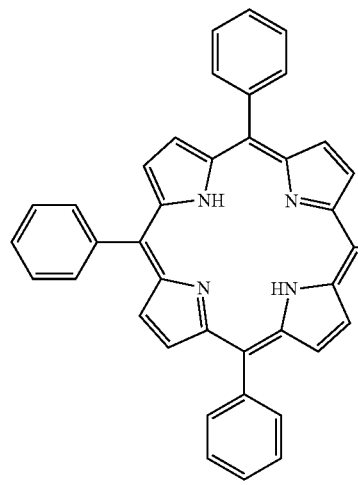 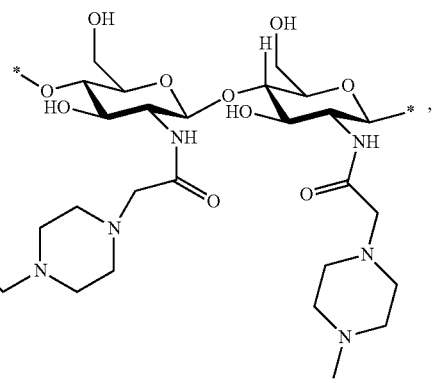
33: B:10%; A:90%
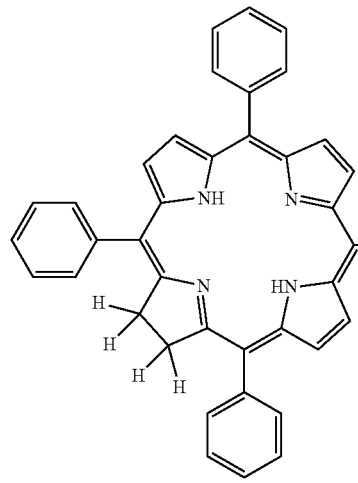 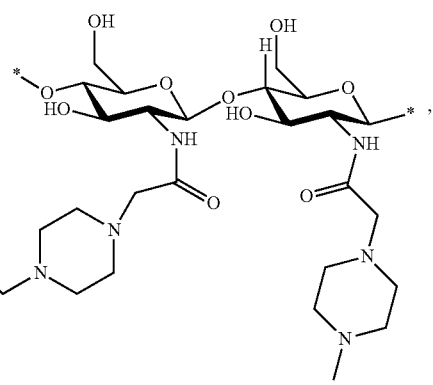
and
37: B:10%; A:90%
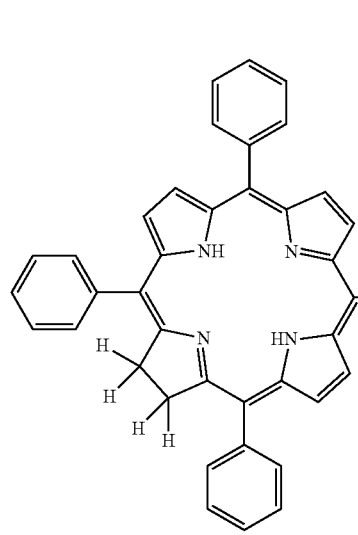 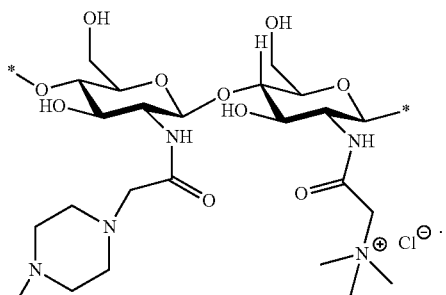

In the above structures, the A/B % values provided refer to the proportion of Rn groups which are group A or B. The asterisks denote the remainder of the chitosan polymer.

These compounds may be made by synthesis methods which utilise procedures standard in the art, which will be familiar to the skilled man. By way of example, synthesis of the preferred conjugates discussed below, numbers 17, 19, 33 and 37, is shown in reaction schemes 1-5B in FIGS. 4A-4F (and see also FIG. 4 legend).

An "antigenic" molecule as referred to herein is a molecule which itself, or a part thereof, is capable of stimulating an immune response, when presented to the immune system or immune cells in an appropriate manner. Advantageously, therefore the antigenic molecule will be a vaccine antigen or vaccine component, such as a polypeptide containing entity.

Many such antigens or antigenic vaccine components are known in the art and include all manner of bacterial or viral antigens or indeed antigens or antigenic components of any pathogenic species including protozoa or higher organisms. Whilst traditionally the antigenic components of vaccines have comprised whole organisms (whether live, dead or attenuated) i.e. whole cell vaccines, in addition sub-unit vaccines, i.e. vaccines based on particular antigenic components of organisms e.g. proteins or peptides, or even carbohydrates, have been widely investigated and reported in the literature. Any such "sub-unit"-based vaccine component may be used as the antigenic molecule of the present invention.

However, the invention finds particular utility in the field of peptide vaccines. Thus, a preferred antigenic molecule according to the invention is a peptide (which is defined herein to include peptides of both shorter and longer lengths i.e. peptides, oligopeptides or polypeptides, and also protein molecules or fragments thereof e.g. peptides of 5-500 e.g. 10 to 250 such as 15 to 75, or 8 to 25 amino acids).

A vast number of peptide vaccine candidates have been proposed in the literature, for example in the treatment of viral diseases and infections such as AIDS/HIV infection or influenza, canine parvovirus, bovine leukaemia virus, hepatitis, etc. (see e.g. Phanuphak et al., Asian Pac. J. Allergy. Immunol. 1997, 15(1), 41-8; Naruse, Hokkaido Igaku Zasshi 1994, 69(4), 811-20; Casal et al., J. Virol., 1995, 69(11), 7274-7; Belyakov et al., Proc. Natl. Acad. Sci. USA, 1998, 95(4), 1709-14; Naruse et al., Proc. Natl. Sci. USA, 1994 91(20), 9588-92; Kabeya et al., Vaccine 1996, 14(12), 1118-22; Itoh et al., Proc. Natl. Acad. Sci. USA, 1986, 83(23) 9174-8. Similarly bacterial peptides may be used, as indeed may peptide antigens derived from other organisms or species.

In addition to antigens derived from pathogenic organisms, peptides have also been proposed for use as vaccines against cancer or other diseases such as multiple sclerosis. For example, mutant oncogene peptides hold great promise as cancer vaccines acting as antigens in the stimulation of cytotoxic T-lymphocytes. (Schirrmacher, Journal of Cancer Research and Clinical Oncology 1995, 121, 443-451; Curtis Cancer Chemotherapy and Biological Response Modifiers, 1997, 17, 316-327). A synthetic peptide vaccine has also been evaluated for the treatment of metastatic melanoma (Rosenberg et al., Nat. Med. 1998, 4(3), 321-7). A T-cell receptor peptide vaccine for the treatment of multiple sclerosis is described in Wilson et al., J. Neuroimmunol. 1997, 76(1-2), 15-28. Any such peptide vaccine component may be used as the antigenic molecule of the invention, as indeed may any of the peptides described or proposed as peptide vaccines in the literature. The peptide may thus be synthetic or isolated or otherwise derived from an organism.

In a preferred embodiment of the present invention the antigen is a melanoma antigen. The "melanoma antigen" can include one or more different antigens.

For example, in one aspect, the melanoma antigen is a melanoma protein or peptide, for example an antigenic peptide or T-cell epitope, for example one or more selected from gp100, Melan-A, tyrosinase, MAGE-1, MAGE-3 and tyrosinase related protein-2 (TRP-2) or a peptide epitope thereof. Details of these and further suitable melanoma antigens are disclosed in Renkvist et al., Cancer Immunol. Immunother. 50:3-15, 2001 (and references therein), and Hodi, Clin. Cancer. Res. 12:673-678, 2006, which are hereby incorporated by reference. In particular, gp100, Melan-2, tyrosinase, MAGE-1, MAGE-3 and TRP-2 and their peptide epitopes are as described in Renkvist et al., supra. Thus the invention extends to use of gp100, Melan-2, tyrosinase, MAGE-1, MAGE-3 or TRP-2, or an antigen comprising or consisting of their disclosed peptide epitopes, as disclosed in Renkvist et al., supra or a sequence with at least 95% sequence identity thereto (over a relevant window of comparison) using standard comparison techniques known in the art. In a preferred embodiment the antigen is TRP-2 and/or gp100, preferably TRP-2.

Peptide antigens, for example up to at least 200 amino acids, may be obtained from companies performing custom peptide synthesis, e.g. United BioSystems Inc (formerly United Peptide Corp., Herndon, Va., USA).

In an alternative preferred embodiment the antigenic molecule is derived from a Human Papilloma Virus (HPV). The papillomavirus genome is divided into an early region (E), encoding six (E1, E2, E4, E5, E6, and E7) open reading frames (ORF) that are expressed immediately after initial infection of a host cell, and a late region (L) encoding a major capsid protein L1 and a minor capsid protein L2. All viral ORFs are encoded on one DNA strand.

In a preferred embodiment the antigenic molecule comprises a protein or peptide, or fragment thereof, i.e. an antigen from a Human papillomavirus (HPV) (e.g. is derived from said virus) which is preferably a protein or part thereof of one of the early or late proteins referred to herein. Thus, the HPV antigen can be one or more known antigenic peptide or T-cell epitope, for example one or more selected from any known antigen from any type of HPV. Details of HPV types and antigens can be found in Ma et al. Current Cancer Therapy Reviews 6: 81-103, 2010.

For example, the antigenic peptide may be derived from HPV-16 and/or HPV-18 type HPV, or type 31 or type 45 HPV. For example, the antigen may be derived from any of the E1, E2, E4, E5, E6 or E7 proteins or any of the L1 and L2 proteins. The antigenic peptide may be derived from one or more of the E2, E6, and E7 proteins of HPV-16 and 18. In a preferred embodiment the antigenic molecule contains the HPV-16 E7 sequence GQAEPDRAHYNIVTFCCKCD-STLRLCVQSTHVDIR (SEQ ID NO:1; the CD8 epitope is shown in bold). Thus, the HPV antigen may be a 35 amino acid peptide. Alternatively, the antigenic molecule may be only the CD8 epitope RAHYNIVTF (SEQ ID NO:2), i.e. a shorter peptide.

HPV peptide antigens may be obtained from companies performing custom peptide synthesis, e.g. United BioSystems Inc (formerly United Peptide Corp., Herndon, Va., USA).

Once released in the cell cytosol by the photochemical internalisation process, the antigenic molecule may be processed by the antigen-processing machinery of the cell. Thus, the antigenic molecule expressed or presented on the surface of the cell may be a part or fragment of the antigenic molecule which is internalised (endocytosed). A "part" of an antigenic molecule which is presented or expressed preferably comprises a part which is generated by antigen-processing machinery within the cell. Parts may, however, be generated by other means which may be achieved through appropriate antigen design (e.g. pH sensitive bonds) or through other cell processing means. Conveniently such parts are of sufficient size to generate an immune response, e.g. in the case of peptides greater than 5, e.g. greater than 10 or 20 amino acids in size.

The agent which enhances PCI-mediated vaccination according to the present invention is a ligand for a Toll-like receptor (TLR). Toll-like receptors are a class of proteins that play a key role in the innate immune system as well as the digestive system. TLRs and Interleukin-1 receptors form a receptor superfamily, named the Interleukin-1 Receptor/Toll-like Receptor superfamily. All members of this family have a Toll-IL-1 receptor domain (TIR). Members of the interleukin-1 receptor (IL-1R) family are characterized by extracellular immunoglobulin-like domains and intracellular Toll/Interleukin-1R (TIR) domain. Receptors with subgroup 2 TIR domains are considered TLRs.

TLRs are single, membrane-spanning, non-catalytic receptors usually expressed in sentinel cells such as macrophages and dendritic cells, that recognize structurally conserved molecules derived from microbes. Once these microbes have breached physical barriers such as the skin or intestinal tract mucosa, they are recognized by TLRs, which activate immune cell responses. These receptors recognize molecules such as pathogen-associated molecules, which are thought to be critical to the pathogen's function and difficult to change through mutation. They may include bacterial cell-surface lipopolysaccharides (LPS), lipoproteins, lipopeptides, and lipoarabinomannan; proteins such as flagellin from bacterial flagella; double-stranded RNA of viruses; or the unmethylated CpG islands of bacterial and viral DNA; and also of the CpG islands found in the promoters of eukaryotic DNA; as well as certain other RNA and DNA molecules. For most of the TLRs, ligand recognition specificity has now been established by gene targeting.

It has been estimated that most mammalian species have between ten and fifteen types of Toll-like receptor. Thirteen TLRs (named simply TLR1 to TLR13) have been identified in humans and mice together (thirteen in mouse and ten in humans).

All ligands for TLR receptors are encompassed by the present invention. The term "ligand" is intended to mean a substance that forms a complex with a biomolecule to serve a biological purpose. In the context of a TLR ligand, it is a signal triggering molecule, binding to a site on a target TLR. When a ligand binds to its cognate receptor it may alter the chemical conformation of the receptor. The conformational state of a receptor protein determines its functional state.

Thus, a TLR ligand according to the present invention is a molecule that binds to at least one, or one or more, toll-like receptor (TLR) and results in activation of the TLR, for example activation of TLR-mediated cell signalling.

TLR signaling is divided into two distinct signaling pathways, the MyD88-dependent and TRIF-dependent pathway. A TLR ligand according to the invention activates one or both of these two pathways. Thus, a ligand according to the present invention is a molecule that binds to one or more TLRs and results in activation of the TLR, for example activation of TLR signalling via a conformational change of the receptor on binding of the ligand.

The MyD88-dependent response occurs on dimerization of the TLR receptor, and is utilized by every TLR except TLR3. Its primary effect is activation of NFκB and Mitogen-activated protein kinase. Ligand binding and conformational change that occurs in the receptor recruits the adaptor protein MyD88, a member of the TIR family. MyD88 then recruits IRAK 4, IRAK1 and IRAK2. IRAK kinases then phosphorylate and activate the protein TRAF6, which in turn polyubiquinates the protein TAK1, as well as itself in order to facilitate binding to IKKß. On binding, TAK1 phosphorylates IKKß, which then phosphorylates IκB causing its degradation and allowing NFκB to diffuse into the cell nucleus and activate transcription and consequent induction of inflammatory cytokines.

The other pathway is the TRIF-dependent pathway, which is used by both TLR3 and TLR4. For TLR3, dsRNA (or similar—see below) leads to activation of the receptor, recruiting the adaptor TRIF. TRIF activates the kinases TBK1 and RIP1, which creates a branch in the signaling pathway. The TRIF/TBK1 signaling complex phosphorylates IRF3 allowing its translocation into the nucleus and production of Interferon type I. Meanwhile, activation of RIP1 causes the polyubiquination and activation of TAK1 and NFκB transcription in the same manner as the MyD88—dependent pathway.

Standard methods for determining activation of TLR signalling are known in the art, for example determination of the phosphorylation state of appropriate signalling proteins. Alternatively, one may determine whether a ligand acts through a TLR by well known methods in the art, e.g. by genetically deleting the gene encoding the specific TLR and determining whether the effect of the ligand is maintained. This method can be used both in vitro and in vivo in transgenic knock-out mice, which are commercially available (TLR2, 3 and 4 knock-outs are available from The Jackson Laboratory and TLR 1, 2, 3, 4, 5, 6, 7 and 9 knock-outs from OrientalBioService Inc). In addition, HEK-Blue™ cells (Invivogen, San Diego, Calif., USA) are available which are designed to study stimulation of TLRs via assaying NF-κB/AP1 activation. Such cells are available for TLRs 2-9 and 13. Also, TLR antagonists such as those available from Invivogen can be used to determine whether antagonism of the TLR inhibits the action of a putative ligand. Thus, methods of determining whether a molecule is a TLR ligand, e.g. a specific TLR ligand, are well known in the art.

The structure of a TLR consists of a leucine-rich repeat (LRR) ectodomain, a helical transmembrane domain, and an intracellular Toll/IL-1 receptor homology (TIR) signaling domain. The ectodomain contains varying numbers of LRRs and resembles a solenoid bent into a horseshoe shape. At both ends there is a terminal LRR that shields the hydrophobic core of the horseshoe. These ectodomains are highly variable. They are directly involved in the recognition of a variety of pathogen-associated motifs including lipopolysaccharide, lipopeptide, cytosine-phosphate-guanine (CpG) DNA, flagellin, imidazoquinoline, and ds/ssRNA. Upon receptor activation, a TIR signaling complex is formed between the receptor and adaptor TIR domains.

The receptors TLR 7, 8, and 9 are a family with a longer amino acid sequence than other TLRs. They are localized intracellularly and signal in response to non-self nucleic acids. They also contain an irregular segment between their LRR14 and 15.

The sequences of TLR receptors are known and binding to those receptors by ligands described herein may be assessed, e.g. as described hereinbefore. By way of example, known TLR amino acid sequences are shown in Table 1 below.

TABLE 1

| TLR | NCBI Reference Sequence | UniProtKB/Swiss-Prot Reference |
|---|---|---|
| toll-like receptor 1 precursor (Homo sapiens) | NP_003254.2 | Q15399 |
| toll-like receptor 2 precursor (Homo sapiens) | NP_003255.2 | O60603 |
| toll-like receptor 3 precursor (Homo sapiens) | NP_003256.1 | O15455 |
| toll-like receptor 4 isoform C (Homo sapiens) | NP_003257.1 | O00206 |
| toll-like receptor 5 precursor (Homo sapiens) | NP_003259.2 | O60602 |
| toll-like receptor 6 precursor (Homo sapiens) | NP_006059.2 | Q9Y2C9 |
| toll-like receptor 7 precursor (Homo sapiens) | NP_057646.1 | Q9NYK1 |
| toll-like receptor 8 precursor (Homo sapiens) | NP_619542.1 | Q9NR97 |
| toll-like receptor 9 precursor (Homo sapiens) | NP_059138.1 | Q9NR96 |
| toll-like receptor 10 isoform a (Homo sapiens) | NP_001017388.1 | Q9BXR5 |
| toll-like receptor 11 (mouse) | | Q6R5P0 |
| toll-like receptor 12 (mouse) | | Q6QNU9 |
| toll-like receptor (mouse) | | Q6R5N8 |

TLR1 is a cell-surface receptor whose ligands include lipoproteins and multiple triacyl lipopeptides, such as those derived from bacteria. TLR 1 does not recognize ligands on its own, rather it acts in a complex with TLR 2. Thus, ligands recognise a complex between TLR1 and TLR2. TLR1 recognises peptidoglycan and (triacyl) lipoproteins in combination with TLR2 (as a heterodimer).

A lipoprotein/peptide is a molecule consisting of a lipid connected to a protein/peptide. Bacteria express such molecules. A triacyl lipoprotein/peptide comprises three acyl groups. Preferably the TLR1 ligand for use according to the invention is a triacyl lipopeptide.

TLR1 ligands can be purchased from Invivogen or Enzo Life Sciences (Farmingdale, N.Y., USA). For example, Pam3CSK4 (Invivogen) is a synthetic triacylated lipopeptide (LP) that mimics the acylated amino terminus of bacterial LPs.

Alternatively, Pam3Cys-Ser-(Lys)4 trihydrochloride (Enzo Life Sciences) may be used which is a selective agonist of TLR1 complexed with TLR2.

TLR2 is a cell surface receptor which is stimulated by a wide array of microbial molecules representing broad groups of species both of Gram-positive and Gram-negative bacteria, as well as *mycoplasma* and yeast. TLR2 recognizes cell-wall components such as peptidoglycan, lipoteichoic acid and lipoprotein from gram-positive bacteria, lipoarabinomannan from mycobacteria, and zymosan from yeast cell wall.

Preferred TLR2 ligands are lipoglycans, such as lipoarabinomannan and lipomannan from *Mycobacterium smegmatis*. Particularly preferred lipoglycans are lipopolysaccharides (LPS) specific for TLR2 (see FIG. 21). These molecules have a lipid and polysaccharide joined by a covalent bond and are found in the outer member of Gram-negative bacteria and act as endotoxins. In a preferred feature the LPS is from *Porphyromonas Gingivalis*. LPS consists of a polysaccharide region that is anchored in the outer bacterial membrane by a specific carbohydrate lipid moiety termed lipid A. Lipid A, also known as endotoxin, is responsible for the immunostimulatory activity of LPS.

The most active form of lipid A contains six fatty acyl groups and is found in pathogenic bacteria such as *Escherichia coli* and *Salmonella* species.

Other preferred TLR2 ligands are lipoteichoic acids e.g. which originate from different bacterial species such as *Bacillus subtilis* and *Staphylococcus aureus*; peptidoglycans, e.g. from bacterial species such as *Bacillus subtilis, E. coli* strains (e.g. 0111:B4 or K12), *Staphylococcus aureus*, and others; synthetic lipoproteins such as synthetic diacylated lipoprotein or synthetic triacylated lipoprotein and zymosan (e.g. from *Saccharomyces cerevisiae*) which is a glucan with repeating glucose units connected by ß-1,3-glycosidic linkages. TLR2 ligands are commercially available from Invivogen.

TLR3 is found in cellular compartments. Preferred ligands according to the invention are double-stranded RNA molecules mimicking viral dsRNA, e.g. Polyadenylic-polyuridylic acid (Poly(A:U)) or Polyinosine-polycytidylic acid (Poly(I:C)). Poly(I:C) is particularly preferred.

Double-stranded RNA (dsRNA) is RNA with two complementary strands, similar to the DNA found in all cells. dsRNA forms the genetic material of some viruses (double-stranded RNA viruses). Double-stranded RNA such as viral RNA or siRNA can trigger RNA interference in eukaryotes, as well as an interferon response in vertebrates.

In a preferred feature the ligand is Poly(I:C). Poly I:C is a mismatched double stranded RNA with one strand being a polymer of inosinic acid, the other a polymer of cytidylic acid. Such molecules may be generated by well known techniques. Various commercial sources exist, e.g. the following may be purchased from Invivogen and form preferred embodiments:

Poly(I:C) (HMW) with a high molecular weight and an average size of 1.5-8 kb, and Poly(I:C) (LMW) with a low molecular weight and an average size of 0.2-1 kb. Both high and low molecular weight forms are preferred forms for use according to the present invention.

TLR4 is also found on the cell surface and has several ligand types, including inter alia lipopolysaccharides (LPS), several heat shock proteins, fibrinogen, heparin sulphate fragments, hyaluronic acid fragments, nickel and various opioid drugs. In a preferred aspect the ligand is LPS. The LPS may originate from various bacterial species, e.g. from *E. coli* 0111:B4 or K12 or *Salmonella* (extracted by a phenol-water mixture), in a preferred feature the LPS is from *E. coli* or from *Salmonella minnesota* e.g. strain R595.

In another preferred aspect the TLR4 ligand is Monophosphoryl Lipid A (MPLA) which may be isolated from bacteria (e.g. *Salmonella minnesota* R595), or made synthetically. In general, TLR4 ligands are available commercially e.g. from Invivogen.

TLR5 binds to the ligand flagellin from both Gram-positive and Gram-negative bacteria such as *Bacillus subtilis, Pseudomonas aeruginosa, Salmonella typhimurium* and others. Flagellin is a globular protein that arranges itself in a hollow cylinder to form the filament in bacterial flagellum. It has a mass of about 30,000 to 60,000 daltons. Flagellin is the principal substituent of bacterial flagellum, and is present in large amounts on nearly all flagellated bacteria. Thus, preferred TLR5 ligands are flagellins, preferably from a bacteria as described above. TLR5 ligands are available commercially e.g. from Invivogen.

TLR6 binds to multiple diacyl lipopeptides. As discussed above, lipopeptides are found in bacteria and comprise a lipid joined to a peptide. A diacyl lipopeptide has 2 acyl groups and forms a preferred TLR6 ligand for use according to the invention. TLR6 ligands are available commercially from Invivogen. For example, FSL-1 (Pam2CGDPKHPKSF; SEQ ID NO:3) is a synthetic lipoprotein derived from *Mycoplasma salivarium* similar to MALP-2, a *M. fermentans* derived lipopeptide (LP). Mycoplasmal LPs, such as FSL-1, contain a diacylated cysteine residue, whereas bacterial LP contain a triacylated one. FSL-1 is recognized by TLR6 in combination with TLR2, whereas bacterial LPs are recognized by a combination of TLR2 and TLR1 as discussed above.

TLR7 ligands include the small synthetic compounds imidazoquinoline, base analogs such as adenine and guanosine analogs (e.g. loxoribine) and bropirimine, and also single-stranded RNA.

Imidazoquinoline compounds are double cyclic organic molecules, preferably with the formula indicated below in which the groups at $R_1$ and $R_2$ may be varied.

Preferably the imidazoquinoline compound has the formula 1:

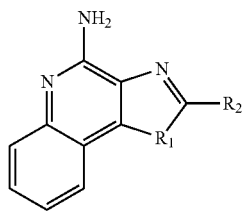

(1)

wherein $R_1$ is an amino-alkyl group, optionally substituted, e.g. with a hydroxyl group and $R_2$ is an alkyl group optionally interrupted with an oxygen or nitrogen group; wherein preferably $R_1$, is N—$CH_2$—$C(CH_3)_2$—$R_3$;

$R_2$ is —$CH_2$—X—$CH_2CH_3$ or a hydrogen atom;

$R_3$ is OH or a hydrogen atom and X is O or NH;

or a pharmaceutically acceptable salt thereof.

In the above formula an alkyl group may be a $C_1$-$C_{10}$ group.

Examples of these compounds are known in the art, e.g. Resiquimod (or R848) (1-[4-amino-2-(ethoxymethyl)imidazo[4,5-c]quinolin-1-yl]-2-methylpropan-2-ol), Imiquimod (3-(2-methylpropyl)-3,5,8-triazatricyclo[7.4.9.0$^{2,6}$]trideca-1(9),2(6),4,7,10,12-hexaen-7-amine) and gardiquimod (R1 is N—$CH_2$—$C(CH_3)_2OH$; $R_2$ is —$CH_2$—NH—$CH_2CH_3$; 1-[4-Amino-2-(ethylaminomethyl)imidazo[4,5-c]quinolin-1-yl]-2-methylpropan-2-ol) (all available from InvivoGen (San Diego Calif., USA)). In a preferred embodiment the compound is selected from Resiquimod and Imiquimod.

Pharmaceutically acceptable salts of these compounds are also encompassed in the invention. Appropriate salts include for example acetate, bromide, chloride, citrate, hydrochloride, maleate, mesylate, nitrate, phosphate, sulphate, tartrate, oleate, stearate, tosylate, calcium, meglumine, potassium and sodium salts.

Loxoribine is a guanosine analog derivatized at position $N^7$ and $C^8$. This nucleoside is a very powerful stimulator of the immune system.

Bropirimine is an experimental drug with anti-cancer and antiviral properties with the structure as shown below:

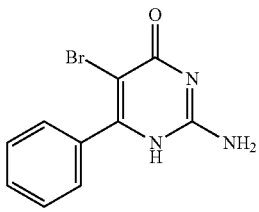 [SMILES: Nc1nc(=O)c(Br)c(-c2ccccc2)[nH]1]

Single stranded RNA is a preferred TLR7 ligand, e.g. ssPolyU, wherein preferably said single stranded molecule is between 20 and 200 nucleotides in length. Such molecules can be readily generated synthetically.

TLR8 ligands are generally small synthetic compounds or single-stranded RNA. Preferably said TLR8 ligand is an ssPolyU molecule as described above.

TLR9 ligands include unmethylated CpG Oligodeoxynucleotide DNA. A "CpG" oligonucleotide (or CpG ODN) is an example of such a ligand, and is a short single-stranded synthetic DNA molecule that results from binding a cytosine triphosphate deoxynucleotide ("C") to a guanine triphosphate deoxynucleotide ("G"). The "p" refers to the phosphodiester link between consecutive nucleotides, although some ODN have a modified phosphorothioate (PS) backbone instead. As referred to herein the CpG nucleotides are referred to as the CpG motif. The CpG motif is unmethylated. Sequences containing CpG motifs are considered pathogen-associated molecular patterns (PAMPs) due to their abundance in microbial genomes but their rarity in vertebrate genomes. The CpG PAMP is recognized by the pattern recognition receptor (PRR) Toll-Like Receptor 9 (TLR9). TLR9 recognizes specific unmethylated CpG oligonucleotides (ODN) sequences that distinguish microbial DNA from mammalian DNA.

Three main types of stimulatory ODNs have been described: type A, B and C. Type A CpG ODNs are constructed of a mixed phosphodiester/phosphorothioate backbone, and contain one or more CpG motif as part of a palindromic sequence. Type A CpG ODNs have poly G tails at the 3' and 5'ends (a structural motif that facilitates the formation of concatemers). Type A CpG ODNs typically contain 7 to 10 phosphorothioate-modified bases at one or both ends that resist degradation by nucleases and increase the stability of the ODN. For example, the internal palindrome sequence can be 8 to 16 (preferably 10, 12 or 14) base pairs in length and varies in the order of bases, however the pattern, 5'-Pu Pu CG Pu: Py CG Py Py-3', wherein the Pu, Py bases equidistant from the palindrome centre, marked with ":", are complementary, is preferred. The poly G tail found at either end of the DNA strand can vary in length.

Type B CpG ODNs may have one or more 6mer consensus sequences containing the CpG motif. A human consensus sequence may contain the sequence 5'-Pu Py C G Py Pu-3'. (Mouse sequences may be different.) Type B CpG ODNs have a fully phosphorothioated (PS-modified) backbone, and are generally 18 to 28 (e.g. 18-22) nucleotides in length. An example of a type B CpG ODN is ODN 1826 which has the sequence 5'-tccatgacgttcctgacgtt-3' (SEQ ID NO:4).

Type C CpG ODNs combine features of both types A and B. Type C CpG ODNs are composed entirely of phosphorothioate nucleotides and contain palindromic sequences containing one or more CpG motif. An example of a type C CpG ODN is ODN 2395 which has the sequence 5'-tcgtcgttttcggcgc:gcgccg-3' (palindrome underlined) (SEQ ID NO:5).

In addition, Type P CpG ODNs which contain two palindromic sequences, enabling them to form higher ordered structures, may also be used.

CpG oligonucleotides can be synthesised by standard oligonucleotide synthesis methods which are known in the art.

Thus CpG oligonucleotides of the invention extend to a single-stranded oligonucleotide of from 6-50 bases, preferably 18-27, preferably 20-25 bases, which includes at least one CpG motif and at least one base flanking said motif on each of the 3' and 5' sides, wherein said CpG motif is a cytosine followed by a guanine linked by a phosphate or phosphorothioate bond in which the pyrimidine ring of the cytosine is unmethylated. In one embodiment, the one or more motif is flanked by sequences, which together with the one or more motif provides a palindromic sequence. As referred to herein a "palindromic sequence" provides a forward sequence linked to the complementary sequence in reverse such that the sequence may form a hairpin, e.g. cggcgc:gcgccg (in which the centre of the palindrome is marked with ":") (SEQ ID NO:6). The CpG motif may form the centre of the sequence and/or be elsewhere in the palindromic sequence. Preferably the palindromic sequence (including both the forward and reverse sequence) is from 8 to 16, preferably 10-12 or 10-14, bases in length.

In a further preferred aspect the CpG oligonucleotide sequence contains the palindromic sequence 5'-Pu Pu CG Pu:Py CG Py Py-3', wherein the Pu, Py bases equidistant from the palindrome centre, marked with ":", are complementary, and/or one or more of the consensus sequences 5'-Pu Py CG Py Pu-3'. Optionally the CpG oligonucleotide may contain poly G tails at the 3' or 5' ends of 3 to 8 bases in length.

In a preferred embodiment of the present invention the CpG oligonucleotide is a type C CPG ODN, of 18-27 bases with a palindromic sequence of 10-14 bases and a phosphorothioate backbone. Particularly preferred is ODN 2395 which has the sequence:

5'-tcgtcgttttcggcgc:gcgccg-3' (SEQ ID NO: 5) (palindromic sequence underlined).

In an alternative preferred embodiment of the present invention the CpG oligonucleotide is a type B CPG ODN, of 18-22 bases and a phosphorothioate backbone. Particularly preferred is ODN 1826 which has the sequence:

5'-tccatgacgttcctgacgtt-3' (SEQ ID NO:4).

TLR11 and 12 ligands include profilin, which is an actin-binding protein involved in the dynamic turnover and restructuring of the actin cytoskeleton. Thus a preferred TLR11/12 ligand is profilin derived from *Toxoplasma gondii* which is an obligate, intracellular, parasitic protozoan that causes the disease toxoplasmosis. Profilin can be purchased from e.g. Enzo Life Sciences.

TLR13 ligands include the bacterial ribosomal RNA sequence "CGGAAAGACC" (SEQ ID NO:7), and nucleic acids comprising this nucleotide sequence and this ligand forms a preferred aspect of the invention. The oligonucleotide having the sequence 5'-GGACGGAAAGAC-CCCGUGG-3' (SEQ ID NO:8) is a TLR13 ligand and can be purchased from e.g. Invivogen.

Thus, preferably said TLR ligand is a TLR 2, 3, 4, 7, 8 or 9 ligand, preferably a ligand as described above. In a preferred embodiment the TLR ligand is a TLR 3 ligand, preferably as described above. In an alternative preferred embodiment the TLR ligand is a TLR 4 ligand, preferably as described above. In yet an alternative preferred embodiment the TLR ligand is a TLR7-9 ligand, or a TLR7 ligand, or a TLR8 ligand or a TLR 9 ligand, preferably as described above.

As used herein "expressing" or "presenting" refers to the presence of the antigenic molecule or a part thereof on the surface of said cell such that at least a portion of that molecule is exposed and accessible to the environment surrounding that cell, preferably such that an immune response may be generated to the presented molecule or part thereof. Expression on the "surface" may be achieved in which the molecule to be expressed is in contact with the cell membrane and/or components which may be present or caused to be present in that membrane.

The term "cell" is used herein to include all eukaryotic cells (including insect cells and fungal cells). Representative "cells" thus include all types of mammalian and non-mammalian animal cells, plant cells, insect cells, fungal cells and protozoa. Preferably, however, the cells are mammalian, for example cells from cats, dogs, horses, donkeys, sheep, pigs, goats, cows, mice, rats, rabbits, guinea pigs, but most preferably from humans. The cell which is subjected to the methods, uses etc. of the invention may be any cell which is capable of expressing, or presenting on its surface a molecule which is administered or transported into its cytosol.

The cell is conveniently an immune cell i.e. a cell involved in the immune response. However, other cells may also present antigen to the immune system and these also fall within the scope of the invention. The cells according to the present invention are thus advantageously antigen-presenting cells as described hereinafter. The antigen-presenting cell may be involved in any aspect or "arm" of the immune response as defined herein.

The stimulation of cytotoxic cells requires antigens to be presented to the cell to be stimulated in a particular manner by the antigen-presenting cells, for example MHC Class I presentation (e.g. activation of $CD8^+$ cytotoxic T-cells requires MHC-1 antigen presentation). Antibody-producing cells may also be stimulated by presentation of antigen by the antigen-presenting cells.

Antigens may be taken up by antigen-presenting cells by endocytosis and degraded in the endocytic vesicles to peptides. These peptides may bind to MHC class II molecules in the endosomes and be transported to the cell surface where the peptide-MHC class II complex may be recognised by CD4+ T helper cells and induce an immune response. Alternatively, proteins in the cytosol may be degraded, e.g. by proteasomes and transported into endoplasmic reticulum by means of TAP (transporter associated with antigen presentation) where the peptides may bind to MHC class I molecules and be transported to the cell surface (Yewdell and Bennink, 1992, Adv. Immunol. 52: 1-123). If the peptide is of foreign antigen origin, the peptide-MHC class I complex will be recognised by CD8+ cytotoxic T-cells (CTLs). The CTLs will bind to the peptide-MHC (HLA) class I complex and thereby be activated, start to proliferate and form a clone of CTLs. The target cell and other target cells with the same peptide-MHC class I complex on the cells surface may be killed by the CTL clone. Immunity against the foreign antigen may be established if a sufficient amount of the antigen can be introduced into the cytosol (Yewdell and Bennink, 1992, supra; Rock, 1996, Immunology Today 17: 131-137). This is the basis for development of inter alia cancer vaccines. One of the largest practical problems is to introduce sufficient amounts of antigens (or parts of the antigen) into the cytosol. This may be solved according to the present invention.

As mentioned previously, once released in the cell cytosol by the photochemical internalisation process, the antigenic molecule may be processed by the antigen-processing machinery of the cell and presented on the cell surface in an appropriate manner e.g. by Class I MHC. This processing may involve degradation of the antigen, e.g. degradation of a protein or polypeptide antigen into peptides, which peptides are then complexed with molecules of the MHC for presentation. Thus, the antigenic molecule expressed or presented on the surface of the cell according to the present invention may be a part or fragment of the antigenic molecule which is internalised (endocytosed).

A variety of different cell types can present antigen on their surface, including for example, lymphocytes (both T and B cells), dendritic cells, macrophages etc. Others include for example cancer cells e.g. melanoma cells. These cells are referred to herein as "antigen-presenting cells". "Professional antigen-presenting cells" which are cells of the immune system principally involved in the presentation of antigen to effector cells of the immune system are known in the art and described in the literature and include B lymphocytes, dendritic cells and macrophages. Preferably the cell is a professional antigen-presenting cell.

For antigen presentation by an antigen-presenting cell to a cytotoxic T-cell (CTL) the antigenic molecule needs to enter the cytosol of the antigen-presenting cell (Germain, Cell, 1994, 76, 287-299).

In embodiments of the invention, for example involving an in vitro or ex vivo method, or alternatively an in vivo method, the cell is a dendritic cell. Dendritic cells are immune cells forming part of the mammalian immune system. Their main function is to process antigenic material and present it on the surface to other cells of the immune system. Once activated, they migrate to the lymph nodes where they interact with T cells and B cells to initiate the adaptive immune response.

Dendritic cells are derived from hematopoietic bone marrow progenitor cells. These progenitor cells initially transform into immature dendritic cells which are characterized by high endocytic activity and low T-cell activation potential. Once they have come into contact with a presentable antigen, they become activated into mature dendritic cells and begin to migrate to the lymph node. Immature dendritic cells phagocytose pathogens and degrade their proteins into small pieces and upon maturation present those fragments at their cell surface using MHC molecules.

The dendritic cells may be derived from any appropriate source of dendritic cells, such as from the skin, inner lining of the nose, lungs, stomach and intestines or the blood. In a particularly preferred embodiment of the present invention the dendritic cells are derived from bone marrow.

Dendritic cells may be isolated from natural sources for use in the in vitro methods of the invention or may be generated in vitro. Dendritic cells arise from monocytes, i.e. white blood cells which circulate in the body and, depending on the right signal, can differentiate into either dendritic cells or macrophages. The monocytes in turn are formed from stem cells in the bone marrow. Monocyte-derived dendritic cells can be generated in vitro from peripheral blood mononuclear cells (PBMCs). Plating of PBMCs in a tissue culture flask permits adherence of monocytes. Treatment of these monocytes with interleukin 4 (IL-4) and granulocyte-macrophage colony stimulating factor (GM-CSF) leads to differentiation to immature dendritic cells (iDCs) in about a week. Subsequent treatment with tumor necrosis factor (TNF) further differentiates the iDCs into mature dendritic cells.

As used herein "contacting" refers to bringing the cells and the photosensitizing agent and/or the antigenic molecule and/or the TLR ligand as defined herein into physical contact with one another under conditions appropriate for internalization into the cells, e.g. preferably at 37° C. in an appropriate nutritional medium, e.g. from 25-39° C. or in vivo at body temperature, i.e. 36-38° C.

The cell may be contacted with the photosensitizing agent and antigenic molecule and the TLR ligand as defined herein sequentially or simultaneously. Preferably, and conveniently the components are contacted with the cell simultaneously. The photosensitizing agent and antigenic molecule (and optionally the TLR ligand) may be taken up by the cell into the same or different intracellular compartments (e.g. they may be co-translocated).

The cells are then exposed to light of suitable wavelengths to activate the photosensitizing compound which in turn leads to the disruption of the intracellular compartment membranes.

WO 02/44396 (which is incorporated herein by reference) describes a method in which the order of the steps in the method may be arranged such that for example the photosensitizing agent is contacted with the cells and activated by irradiation before the molecule to be internalised (in this case the antigenic molecule) is brought into contact with the cells. This method takes advantage of the fact that it is not necessary for the molecule to be internalised to be present in the same cellular subcompartment as the photosensitizing agent at the time of irradiation.

Thus in one embodiment, said photosensitizing agent and/or said antigenic molecule and/or the TLR ligand as defined herein are applied to the cell together, or separately relative to one another. Irradiation is then performed at a time when at least the photosensitizing agent and the antigenic molecule appear in the same intracellular compartment. This is referred to as a "light after" method.

In an alternative embodiment, said method can be performed by contacting said cell with the photosensitizing agent first, followed by contact with the antigenic molecule and/or the TLR ligand as defined herein, and irradiation is performed after uptake of the photosensitizing agent into an intracellular compartment, but prior to the cellular uptake of the antigenic molecule (and optionally the TLR ligand) into an intracellular compartment containing said photosensitizing agent (e.g. it may be present in a different intracellular compartment at the time of light exposure), preferably prior to cellular uptake into any intracellular compartment, e.g. prior to any cellular uptake. Thus for example the photosensitizing agent may be administered followed by irradiation and then administration of the remaining agents. This is the so-called "light before" method.

"Internalisation" as used herein, refers to the intracellular, e.g. cytosolic, delivery of molecules. In the present case "internalisation" may include the step of release of molecules from intracellular/membrane bound compartments into the cytosol of the cells.

As used herein, "cellular uptake" or "translocation" refers to one of the steps of internalisation in which molecules external to the cell membrane are taken into the cell such that they are found interior to the outer lying cell membrane, e.g. by endocytosis or other appropriate uptake mechanisms, for example into or associated with intracellular membrane-restricted compartments, for example the endoplasmic reticulum, Golgi body, lysosomes, endosomes etc.

The step of contacting the cells with the various agents may be carried out in any convenient or desired way. Thus, if the contacting step is to be carried out in vitro the cells may conveniently be maintained in an aqueous medium, such as for example appropriate cell culture medium, and at the appropriate time point the various agents can simply be added to the medium under appropriate conditions, for example at an appropriate concentration and for an appropriate length of time. For example, the cells may be contacted with the agents in the presence of serum-free medium, or with serum-containing medium.

The comments below discuss the application of the various agents to the cells separately. As discussed above however, these agents may be applied to cells together, separately, simultaneously or sequentially. As referred to herein, the application of the various agents used in the methods of the invention may be to cells in vitro or in vivo. In the latter case, the application may be via direct (i.e. localized) or indirect (i.e. systemic or non-localized) administration as described in more detail hereinbelow.

The photosensitizing agent is brought into contact with the cells at an appropriate concentration and for an appropriate length of time which can easily be determined by a skilled person using routine techniques, and will depend on such factors as the particular photosensitizing agent used and the target cell type and location. The concentration of the photosensitizing agent is conveniently such that once taken up into the cell, e.g. into, or associated with, one or more of its intracellular compartments and activated by irradiation, one or more cell structures are disrupted e.g. one or more intracellular compartments are lysed or disrupted. For example photosensitizing agents as described herein may be used at a concentration of, for example, 10 to 50 μg/ml.

For in vitro use the range can be much broader, e.g. 0.0005-500 μg/ml. For in vivo human treatments the photosensitizing agent may be used in the range 0.05-20 mg/kg body weight when administered systemically. Alternatively, a range of 0.005-20 mg/kg body weight may be used for systemic administration. More conveniently the photosensitizing agent is administered locally, for example by intradermal, subcutaneous or intratumoural administration, and in that case the dose may be in the region of 1-5000 μg, for example 10-2500, 25-1000, 50-500, 10-300 or 100-300 μg. Preferably the dose is selected from 100 μg, 150 μg, 200 μg and 250 μg. Preferably the dose is 75-125 μg, e.g. 100 μg. The doses provided are for a human of average weight (i.e. 70 kg). For intradermal injection the photosensitiser dose may be dissolved in 100 μl-1 ml, i.e. the concentration may be in the range of 1-50000 μg/ml. In smaller animals the concentration range may be different and can be adjusted accordingly though when administered locally, little variation in dosing is necessary for different animals.

The concentration of antigen to be used will depend on the antigen which is to be used. Conveniently a concentration of 0.001-500 μg/ml (e.g. 20-500, 20-300, 20-100 μg/ml, 20-50, 10-50, 5-50, 1-50, 0.01-50, or 0.001-50 μg/ml) antigen may be used in vitro. For a peptide antigen a lower concentration e.g. of 0.001-500, e.g. 0.001-1, 5, 25, 50 or 100 μg/ml may be used. For a protein antigen a higher concentration of e.g. 0.5-500 μg/ml may be used. For in vivo use the protein antigen dose may be in the range 0.5-500 μg, for example 10-100 μg or 10-200 μg. For peptide antigens an in vivo dose of 0.1-4000 μg, e.g. 0.1-2000 μg, 0.1-1000 μg or 0.1-500 μg, for example 0.1-100 μg, may be employed. Such doses are appropriate for local administration. An appropriate concentration can be determined depending on the efficiency of uptake of the agent in question into the cells in question and the final concentration it is desired to achieve in the cells.

The concentration of the TLR ligand as defined herein will also depend on the particular molecule which is to be used, and the skilled man will be aware of suitable concentrations or doses. Examples of suitable in vitro and in vivo concentrations or doses are shown in Table 2 below.

TABLE 2

| Ligand | In vitro concentration | In vivo dosage (preferably for local administration |
|---|---|---|
| LPS | 0.001-100 μg/ml | 0.1-100 μg |
| Flagellin | 1-100 μg/ml | 1-200 μg |
| Poly(IC) | 0.01-100 μg/ml | 1 μg-5 mg (or to 10 mg) (e.g. 10 μg-5 mg) |
| ssPolyU | 1-10 000 ng/ml | 10 μg-5 mg |
| MPLA | 1-10 000 ng/ml | 2-500 μg |
| Imidazoquinolines | 0.01-100 μg/ml | 10-1000 μg (or to 10 mg), e.g. 20-100 μg in mice and 10 μg-10 mg in humans |
| CpG ODNs | 1-100 μg/ml | 10-1000 μg (or to 10 mg) e.g. 20-100 μg in mice and 10 μg-10 mg in humans |

Thus, for example, conveniently a concentration of 1-100 μg/ml (e.g. 20-100 μg/ml, or 20-50 μg/ml) may be used in vitro. In vivo doses of 10-1000 μg of the imidazoquinoline compound may be used, for example 20-100 μg in a mouse, and in humans 10 μg-10 mg may be employed. For topical administration of e.g. imiquimod in humans, a dose of 2.5-50 mg, e.g. at 1-5 mg/cm$^2$, e.g. 2.5 mg/cm$^2$, may be used. For resiquimod the dose may be 0.1-50 mg, e.g. 1-5 mg, e.g. at 1-5 mg/cm$^2$. A similar dose is suitable for gardiquimod. For intradermal injection of the imidazoquinoline compound a smaller dose may be used, for example at least 10 μg or 50 μg, e.g. 10 μg-1 mg could be used. Similar doses may be used for the CpG oligonucleotide and other TLR ligands. Poly(IC) may be administered at an in vivo dose of 1-100 μg in mice and 1 μg-10 mg in humans.

In most cases the photosensitizing agent, the antigenic molecule and the TLR ligand as defined herein are administered together, but this may be varied. Thus different times or modes or sites of administration (or contact with the cell) are contemplated for each of the different components and such methods are encompassed within the scope of the invention.

In one embodiment the TLR ligand, for example a CpG oligonucleotide or an imidazoquinoline compound, an LPS or a poly(IC) molecule as defined herein is administered separately from the antigen, for example in a separate formulation, e.g. a cream or gel, or systemically, e.g. via oral administration (for example with resiquimod). Thus, in one embodiment the TLR ligand, e.g. a CpG oligonucleotide or imidazoquinoline compound may be administered prior to administration of the antigen and/or photosensitiser, for example 24 hours before, e.g. by local (topical) pretreatment. In some cases the TLR ligand, e.g. Poly(IC) or LPS is administered before, with or after the antigen.

The TLR ligand may be administered separately relative to the other agents, e.g. approximately 2 hours prior to illumination. In an alternative embodiment the agent may be administered with or at the same time, i.e. simultaneously, as the antigen.

The contact between the cell and the photosensitizing agent and/or antigenic molecule and/or the TLR ligand as defined herein is conveniently from 15 minutes to 24 hours, e.g. 30 minutes to four hours, preferably from 1.5 to 2.5 hours. Alternatively, the range of time may be from about 1 hour to about 48 hours, for example from about 2 hours to about 40 hours, or from about 6 hours to about 36 hours, e.g. from 12 hours to 30 hours, e.g. 16 hours to 20 hours, for example 18 hours or about 18 hours.

In a preferred embodiment the initial incubation of the cell is with the photosensitising agent. In one embodiment the time between the administration of the photosensitizing agent and the antigenic molecule and/or TLR ligand is a matter of hours. For example, the photosensitizing agent may be applied 16 to 20 hours, e.g. 18 hours, before illumination, and the antigenic molecule and/or TLR ligand may be applied 1 to 3 hours, e.g. 2 hours before illumination. Thus, the time between the administration of the photosensitizing agent and the antigenic molecule and/or the TLR ligand may be in the range of 15 to 23 hours.

Thus, the cell is then incubated with the antigen and/or TLR ligand as defined herein after the incubation with the photosensitiser. Conveniently the cells may be placed into photosensitizer/antigen-free medium after the contact with the photosensitizer/antigen and before irradiation, e.g. for 30 minutes to 4 hours, e.g. from 1.5 to 2.5 hours, depending on the timing of the incubation with the photosensitiser and antigenic molecule and TLR ligand.

In vivo an appropriate method and time of incubation by which the various agents are brought into contact with the target cells will be dependent on factors such as the mode of administration and the type of agents which are used. For example, if the agents are injected into a tumour, tissue or organ which is to be treated/irradiated, the cells near the injection point will come into contact with and hence tend to take up the agents more rapidly than the cells located at a greater distance from the injection point, which are likely to come into contact with the agents at a later time point and lower concentration. Conveniently a time of 6-24 hours may be used.

In addition, agents administered by intravenous injection or orally may take some time to arrive at the target cells and it may thus take longer post-administration e.g. several days, in order for a sufficient or optimal amount of the agents to accumulate in a target cell or tissue. The time of administration required for individual cells in vivo is thus likely to vary depending on these and other parameters.

Nevertheless, although the situation in vivo is more complicated than in vitro, the underlying concept of the present invention is still the same, i.e. the time at which the molecules come into contact with the target cells must be such that before irradiation occurs an appropriate amount of the photosensitizing agent has been taken up by the target cells and either: (i) before or during irradiation the antigenic molecule (and optionally the TLR ligand) has either been taken up, or will be taken up after sufficient contact with the target cells, into the cell, for example into the same or different intracellular compartments relative to the photosensitizing agent or (ii) after irradiation the antigenic molecule (and optionally the TLR ligand) is in contact with the cells for a period of time sufficient to allow its uptake into the cells.

For administration of agents described herein in vivo, any mode of administration common or standard in the art may be used, e.g. injection, infusion, topical administration, transdermal administration, both to internal and external body surfaces etc. For in vivo use, the invention can be used in relation to any tissue which contains cells to which the photosensitising agent containing compound or the molecule to be internalized is localized, including body fluid locations, as well as solid tissues. All tissues can be treated as long as the photosensitiser is taken up by the target cells, and the light can be properly delivered. Preferred modes of administration are intradermal, subcutaneous, topical or intratumoural administration or injection. Preferably administration is by intradermal injection.

To achieve the desired outcome, e.g. antigen presentation, generation of an immune response or vaccination, the methods or parts thereof may be repeated, e.g. "re-vaccination" may take place. Thus, the method in its entirety may be performed multiple times (e.g. 2, 3 or more times) after an appropriate interval or parts of the method may be repeated, e.g. further administration of the TLR ligand as defined herein or additional irradiation steps. For example, the method or part of the method may be performed again a matter of days, e.g. between 5 and 60 days (for example 7, 14, 15, 21, 22, 42 or 51 days), e.g. 7-20 days, preferably 14 days, or weeks, e.g. between 1 and 5 weeks (for example, 1, 2, 3 or 4 weeks) after it was first performed. All or part of the method may be repeated multiple times at appropriate intervals of time, e.g. every two weeks or 14 days. In a preferred embodiment the method is repeated at least once. In another embodiment the method is repeated twice.

In one embodiment, in the second or subsequent time the method is carried out the antigenic molecule is administered in combination with the photosensitiser and illumination, i.e. the TLR ligand is not administered in the second or subsequent time the method is carried out.

In an alternative embodiment, parts of the method of the invention may be carried out prior to the method of the invention being carried out. For example, the method may be carried out one or more times, for example twice, in the absence of TLR ligand before the method of the invention is carried out. Alternatively, the method may be carried out one or more times, for example twice, in the absence of photosensitiser and illumination before the method of the invention is carried out. Part of the method may be carried out a matter of days, e.g. 7 or 14 days, or weeks, e.g. 1, 3 or 4 weeks before the method of the invention is carried out. Part of the method may be repeated one or more times at these time intervals before the method of the invention is carried out. Thus, in a preferred aspect, the antigenic molecule is administered (e.g. to the subject) equal to or greater than 2 times (e.g. at the time intervals discussed above), wherein at least the administration of said antigenic molecule is performed in accordance with the method of the invention.

"Irradiation" to activate the photosensitising agent refers to the administration of light directly or indirectly as described hereinafter. Thus subjects or cells may be illuminated with a light source for example directly (e.g. on single cells in vitro) or indirectly, e.g. in vivo when the cells are below the surface of the skin or are in the form of a layer of cells not all of which are directly illuminated, i.e. without the screen of other cells. Illumination of the cell or subject may occur approximately 18-24 hours after administration of the photosensitizing agent, antigenic molecule and the TLR ligand as defined herein.

The light irradiation step to activate the photosensitising agent may take place according to techniques and procedures well known in the art. The wavelength of light to be used is selected according to the photosensitising agent to be used. Suitable artificial light sources are well known in the art, e.g. using blue (400-475 nm) or red (620-750 nm) wavelength light. For $TPCS_{2a}$ for example a wavelength of between 400 and 500 nm, more preferably between 400 and 450 nm, e.g. from 430-440 nm, and even more preferably approximately 435 nm, or 435 nm may be used. Where appropriate the photosensitiser, e.g. a porphyrin or chlorin, may be activated by green light, for example the KillerRed (Evrogen, Moscow, Russia) photosensitizer may be activated by green light.

Suitable light sources are well known in the art, for example the LumiSource® lamp of PCI Biotech AS. Alternatively, an LED-based illumination device which has an adjustable output power of up to 60 mW and an emission spectra of 430-435 nm may be used. For red light, a suitable source of illumination is the PCI Biotech AS 652 nm laser system SN576003 diode laser, although any suitable red light source may be used.

The time for which the cells are exposed to light in the methods of the present invention may vary. The efficiency of the internalisation of a molecule into the cytosol increases with increased exposure to light to a maximum beyond which cell damage and hence cell death increases.

A preferred length of time for the irradiation step depends on factors such as the target, the photosensitizer, the amount of the photosensitizer accumulated in the target cells or tissue and the overlap between the absorption spectrum of the photosensitizer and the emission spectrum of the light source. Generally, the length of time for the irradiation step is in the order of seconds to minutes or up to several hours (even up to 12 hours), e.g. preferably up to 60 minutes e.g. from 0.25 or 1 to 30 minutes, e.g. from 0.5 to 3 minutes or from 1 to 5 minutes or from 1 to 10 minutes e.g. from 3 to 7 minutes, and preferably approximately 3 minutes, e.g. 2.5 to 3.5 minutes. Shorter irradiation times may also be used, for example 1 to 60 seconds, e.g. 10-50, 20-40 or 25-35 seconds.

Appropriate light doses can be selected by a person skilled in the art and again will depend on the photosensitizer used and the amount of photosensitizer accumulated in the target cells or tissues. The light doses are usually lower when photosensitizers with higher extinction coefficients (e.g. in the red area, or blue area if blue light is used, depending on the photosensitiser used) of the visible spectrum are used. For example, a light dose in the range of 0.24-7.2 J/cm$^2$ at a fluence range of 0.05-20 mW/cm$^2$, e.g. 2.0 mW/cm$^2$, may be used when an LED-based illumination device which has an adjustable output power of up to 60 mW and an emission spectra of 430-435 nm is employed. Alternatively, e.g. if the LumiSource® lamp is employed a light dose in the range of 0.1-6 J/cm$^2$ at a fluence range of 0.1-20 (e.g. 13 as provided by Lumisource®) mW/cm$^2$ is appropriate. For red light, a light dose of 0.03-1 J/cm$^2$, e.g. 0.3 J/cm$^2$, at a fluence range of 0.1-5 mW/cm$^2$, e.g. 0.81 mW/cm$^2$, may be used.

Furthermore, if cell viability is to be maintained, the generation of excessive levels of toxic species is to be avoided and the relevant parameters may be adjusted accordingly.

The methods of the invention may inevitably give rise to some cell damage by virtue of the photochemical treatment i.e. by photodynamic therapy effects through the generation of toxic species on activation of the photosensitizing agent. Depending on the proposed use, this cell death may not be of consequence and may indeed be advantageous for some applications (e.g. cancer treatment). In most embodiments, however, cell death is avoided to allow the generation of an immune response from the presenting cell. The methods of the invention may be modified such that the fraction or proportion of the surviving cells is regulated by selecting the light dose in relation to the concentration of the photosensitizing agent. Again, such techniques are known in the art.

Preferably, substantially all of the cells, or a significant majority (e.g. at least 75%, more preferably at least 80, 85, 90 or 95% of the cells) are not killed. In vitro cell viability following PCI treatment can be measured by standard techniques known in the art such as the MTS test. In vivo cell death of one or more cell types may be assessed within a 1 cm radius of the point of administration (or at a certain depth of tissue), e.g. by microscopy. As cell death may not occur instantly, the % cell death refers to the percent of cells which remain viable within a few hours of irradiation (e.g. up to 4 hours after irradiation) but preferably refers to the % viable cells 4 or more hours after irradiation.

The method may be performed in vivo, in vitro or ex vivo. Preferably the method is used in vitro or ex vivo to generate cells for administration in vivo or the method is used in vivo. Thus in a preferred feature, the method may be used to generate an immune response in a subject.

Thus, in a further aspect the present invention provides a method of generating an immune response in a subject, comprising administering to said subject an antigenic molecule, a photosensitizing agent, and a TLR ligand as defined hereinbefore, and irradiating said subject with light of a wavelength effective to activate said photosensitizing agent, wherein an immune response is generated.

An "immune response" which may be generated may be humoral and cell-mediated immunity, for example the stimulation of antibody production, or the stimulation of cytotoxic or killer cells, which may recognise and destroy (or otherwise eliminate) cells expressing "foreign" antigens on their surface. The term "stimulating an immune response" thus includes all types of immune responses and mechanisms for stimulating them and encompasses stimulating CTLs which forms a preferred aspect of the invention. Preferably the immune response which is stimulated is cytotoxic CD8 T cells. The extent of an immune response may be assessed by markers of an immune response, e.g. secreted molecules such as IL-2 or IFNγ or the production of antigen specific T cells (e.g. assessed as described in the Examples).

The stimulation of cytotoxic cells or antibody-producing cells, requires antigens to be presented to the cell to be stimulated in a particular manner by the antigen-presenting cells, for example MHC Class I presentation (e.g. activation of CD8$^+$ cytotoxic T-cells requires MHC-I antigen presentation). Preferably the immune response is stimulated via MHC-I presentation.

Preferably the immune response is used to treat or prevent a disease, disorder or infection, e.g. cancer.

In one embodiment the cancer is melanoma. Melanoma is a malignant tumour of melanocytes, which are the cells responsible for producing melanin, the dark pigment responsible for skin colour. These cells occur predominantly in the skin, but are also found in other parts of the body, including the bowel and the eye. Melanoma can originate in any part of the body that contains melanocytes.

"Melanoma" as referred to herein includes all types of melanoma, including for example superficial spreading melanoma, nodular melanoma, lentigo maligna melanoma, desmoplastic melanoma, acral lentiginous melanoma and amelanotic melanoma, polypoid melanoma, melanoma with small nevus-like cells and melanoma with features of a Spitz nevus.

Whilst the majority of melanomas occur cutaneously (cutaneous malignant melanoma), melanoma can also occur elsewhere in the body, for example in the internal organs, e.g. in the mucosal membranes. Clear cell sarcoma is a malignant melanoma of the soft tissues. Melanoma can also occur in the eye (uveal melanoma), vulva, vagina or rectum. These melanomas are also included in the scope of the invention. Preferably the melanomas to be treated are skin melanomas. Melanoma also extends to metastatic melanoma, i.e. cells that have originated from a primary melanoma but which have metastasised to a different location to yield secondary tumours. Treatment or prevention of melanoma as described herein extends to treatment of primary melanomas and/or secondary tumours deriving from the primary melanoma. As such, the invention also has utility in treating metastatic melanoma.

In an alternative embodiment, the cancer is associated with or caused/induced by a papillomavirus, particularly a human papillomavirus (HPV). As discussed above, the papillomavirus genome is divided into an early region (E), encoding six (E1, E2, E4, E5, E6, and E7) open reading frames (ORF) that are expressed immediately after initial infection of a host cell, and a late region (L) encoding a major capsid protein L1 and a minor capsid protein L2. All viral ORFs are encoded on one DNA strand. The HPV antigen which may be used according to the invention, which can be associated with cancers resulting from HPV infection, can be one or more known antigenic peptide or T-cell epitope as discussed herein. As discussed above, there are several types of HPV, and the cancer associated with HPV according to the present invention may be associated with, or result from, any type of HPV, for example HPV-16 and/or HPV-18, or HPV-31 or HPV-45. The antigen to be used according to the invention may be derived from any of the E1, E2, E4, E5, E6 or E7 proteins or any of the L1 and L2 proteins. Thus, the antigenic molecule may be derived from one or more of the E2, E6, and E7 proteins of HPV-16 and 18. In a preferred embodiment the antigenic molecule contains the HPV-16 E7 sequence GQAEPDRAHYNIVT-FCCKCDSTLRLCVQSTHVDIR (SEQ ID NO:1; the CD8 epitope is shown in bold). Thus, the HPV antigen may be a 35 amino acid peptide. Alternatively, the antigenic molecule may be only the CD8 epitope RAHYNIVTF (SEQ ID NO:2), i.e. a shorter peptide.

In an alternative embodiment, the disease, disorder or infection is a viral infection, preferably a papillomavirus infection, particularly a human papillomavirus (HPV) infection.

Preferably the method is used for vaccination. As referred to herein, "vaccination" is the use of an antigen (or a molecule containing an antigen) to elicit an immune response which is prophylactic or therapeutic against the development (or further development) of a disease, disorder or infection, wherein that disease, disorder or infection is associated with abnormal expression or presence of that antigen. Preferably the disease is cancer, for example melanoma or a cancer associated with a papillomavirus such as HPV. In one embodiment the vaccination is therapeutic, for example in the treatment of cancers discussed herein. In an alternative embodiment the vaccination is prophylactic, for example to prevent a cancer or to reduce further cancers developing following treatment of an earlier cancer with a therapeutic vaccination. In a further embodiment when an immune response to an infection is to be generated, e.g. a viral infection such as HPV infection, the vaccination is prophylactic in nature.

In a preferred embodiment of the present invention, the subject of the method, e.g. vaccination, is a mammal, preferably a cat, dog, horse, donkey, sheep, pig, goat, cow, mouse, rat, rabbit or guinea pig, but most preferably the subject is a human.

Preferably the methods described herein achieve synergy, i.e. the extent of cell surface presentation or the immune response generated is enhanced more than the combined enhancement observed by (i) performing the method with the antigenic molecule in the absence of the TLR ligand and (ii) performing the method with the antigenic molecule in the absence of the photosensitizing agent and the irradiation step, i.e. synergy between the methods is observed. The level of cell surface presentation or immune response generation may be assessed by appropriate means, e.g. number of antigen-specific CD8+ cells or levels of markers of immune response activation, e.g. IFNγ or IL-2.

"Synergy" as used to herein refers to a quantitative improvement over merely additive effects.

The various agents used in the methods of the invention may be administered to the subject separately, sequentially or simultaneously.

Aspects and features discussed above in relation to the method of expressing an antigenic molecule or a part thereof on the surface of a cell of the present invention, where appropriate, are also applicable to the method of generating an immune response above.

The invention also provides a method for introducing an antigenic molecule into the cytosol of a cell, comprising contacting said cell with the antigenic molecule to be introduced, a photosensitising agent and a TLR ligand as defined herein, and irradiating the cell with light of a wavelength effective to activate the photosensitising agent. Once activated, intracellular compartments within said cell containing said compound release the molecule contained in these compartments into the cytosol.

The methods of the invention above may be used in vitro or in vivo, for example either for in situ treatment or for ex vivo treatment followed by the administration of the treated cells to the body.

The invention further provides a cell expressing an antigenic molecule, or a part thereof, on its surface, or a population thereof, which cell is obtainable (or obtained) by any of the methods as defined herein. Also provided is the cell or cell population for use in prophylaxis, or therapy, as described hereinafter.

The cell population may be provided in a pharmaceutical composition comprising in addition one or more pharmaceutically acceptable diluents, carriers or excipients.

The present invention also provides a pharmaceutical composition comprising an antigenic molecule, a photosensitizing agent, and a TLR ligand as defined herein and one or more pharmaceutically acceptable diluents, carriers or excipients.

These compositions (and products of the invention) may be formulated in any convenient manner according to techniques and procedures known in the pharmaceutical art, e.g. using one or more pharmaceutically acceptable diluents, carriers or excipients. "Pharmaceutically acceptable" as referred to herein refers to ingredients that are compatible with other ingredients of the compositions (or products) as well as physiologically acceptable to the recipient. The nature of the composition and carriers or excipient materials, dosages etc. may be selected in routine manner according to choice and the desired route of administration, purpose of treatment etc. Dosages may likewise be determined in routine manner and may depend upon the nature of the molecule (or components of the composition or product), purpose of treatment, age of patient, mode of administration etc. In connection with the photosensitizing agent, the potency/ability to disrupt membranes on irradiation, should also be taken into account.

The cells, for example antigen presenting cells, may be prepared in vitro. In treatment methods, these cells may be administered to a body in vivo or a body tissue ex vivo such that those cells may stimulate an immune response, e.g. for prophylactic or therapeutic purposes.

Thus the invention further provides a cell population (or composition containing the same) as defined herein, or an antigenic molecule, a photosensitizing agent, and a TLR ligand as defined herein, for use in prophylaxis or therapy or for use in stimulating an immune response, for example for vaccination purposes, e.g. for stimulating CTLs, in a subject, preferably for treating or preventing a disease, disorder or infection in said subject, particularly for treating or preventing cancer, such as melanoma or cancers associated with a papillomavirus such as HPV. Alternatively defined the present invention provides use of (i) a cell population, (ii) a composition as defined herein, or (iii) an antigenic molecule and/or a photosensitizing agent and/or a TLR ligand, for the preparation of a medicament for use in stimulating an immune response (e.g. for stimulating CTLs) in a subject, preferably for treating or preventing a disease, disorder or infection in said subject, preferably for vaccination and/or for treating or preventing cancer, such as melanoma or cancers associated with a papillomavirus such as HPV, wherein preferably said immune response is stimulated by a method as defined herein.

Said stimulation, treatment or prevention preferably comprises administering said medicament to said subject.

The antigenic molecule, photosensitizing agent and the TLR ligand may be combined and presented in a composition. Alternatively expressed, the invention provides use of an antigenic molecule and/or a photosensitizing agent and/or a TLR ligand as defined herein in the manufacture of a medicament for stimulating an immune response (e.g. for stimulating CTLs in a subject), preferably to treat or prevent a disease, disorder or infection in said subject, particularly for vaccination purposes, wherein said medicament comprises a population of cells expressing an antigenic molecule or a part thereof on the surface of said cells obtainable by a method as defined herein, for administration to said subject. Preferably the cell population is obtained by such methods. The population is for administration to the subject.

In an alternative embodiment the present invention provides an antigenic molecule, photosensitizing agent and a TLR ligand as defined herein for use in expressing said antigenic molecule or a part thereof on the surface of a cell to stimulate an immune response (e.g. for stimulating CTLs) in a subject, preferably to treat or prevent a disease, disorder or infection in said subject, wherein said use comprises a method as defined herein, preferably to prepare a population of cells, e.g. dendritic cells. These cells may then be administered to the subject.

The invention further provides a product comprising an antigenic molecule, photosensitizing agent and a TLR ligand as defined herein as a combined preparation for simultaneous, separate or sequential use in stimulating an immune response in a subject (or for expressing an antigenic molecule or a part thereof on the surface of a cell or for internalising an antigenic molecule into the cytosol of a cell) in a method as defined herein, preferably to treat or prevent a disease, disorder or infection in a subject.

The present invention also provides a kit for use in stimulating an immune response in a subject, preferably for treating or preventing a disease, disorder or infection in said subject, for example for use in vaccination or immunisation, or for expressing an antigenic molecule or a part thereof on the surface of a cell or for internalising an antigenic molecule into the cytosol of a cell in a method as defined herein, said kit comprising a first container containing a photosensitizing agent as defined herein;
a second container containing said antigenic molecule as defined herein; and
a third container containing a TLR ligand as defined herein.

The products and kits of the invention may be used to achieve cell surface presentation (or therapeutic methods) as defined herein.

In a yet further embodiment the present invention provides a method of generating an immune response (e.g. for stimulating CTLs) in a subject, preferably to treat or prevent a disease, disorder or infection in said subject, comprising preparing a population of cells according to the method defined herein, and subsequently administering said cells to said subject.

The antigenic presentation achieved by the claimed invention may advantageously result in the stimulation of an immune response when the treated cells are administered in vivo. Preferably an immune response which confers protection against subsequent challenge by an entity comprising or containing said antigenic molecule or part thereof is generated, and consequently the invention finds particular utility as a method of vaccination.

The disease, disorder or infection is any disease, disorder or infection which may be treated or prevented by the generation of an immune response, e.g. by eliminating abnormal or foreign cells which may be identified on the basis of an antigen (or its level of expression) which allows discrimination (and elimination) relative to normal cells. Selection of the antigenic molecule to be used determines the disease, disorder or infection to be treated. Based on the antigenic molecules discussed above, the methods, uses, compositions, products, kits and so forth, described herein may be used to treat or prevent against, for example, infections (e.g. viral or bacterial as mentioned hereinbefore), cancers or multiple sclerosis. Prevention of such diseases, disorders or infection may constitute vaccination.

As defined herein "treatment" refers to reducing, alleviating or eliminating one or more symptoms of the disease, disorder or infection which is being treated, relative to the symptoms prior to treatment. "Prevention" (or prophylaxis) refers to delaying or preventing the onset of the symptoms of the disease, disorder or infection. Prevention may be absolute (such that no disease occurs) or may be effective only in some individuals or for a limited amount of time.

For in vivo administration of the cells, any mode of administration of the cell population which is common or standard in the art may be used, e.g. injection or infusion, by an appropriate route. Conveniently, the cells are administered by intralymphatic injection. Preferably $1\times10^4$ to $1\times10^8$ cells are administered per kg of subject (e.g. $1.4\times10^4$ to $2.8\times10^6$ per kg in human). Thus, for example, in a human, a dose of $0.1$-$20\times10^7$ cells may be administered in a dose, i.e. per dose, for example as a vaccination dose. The dose can be repeated at later times if necessary.

The invention will now be described in more detail in the following non-limiting Examples with reference to the following drawings in which:

FIGS. 1A-1C show % antigen specific T-cells in the blood (FIG. 1A) and spleen (FIG. 1B and FIG. 1C) after in vivo vaccination of mice with a mixture of the antigen ovalbumin (OVA), and where stated $TPCS_{2a}$ (PCI) and CpG or R848. FIG. 1A shows the % of antigen specific CD8+ T-cells in blood 7 days after vaccination, each circle represents one animal. FIG. 1B shows the % of antigen specific CD8+ T-cells in spleen 14 days after vaccination, each circle represents one animal. FIG. 1C is a bar diagram representation of the same data as shown in FIG. 1B.

FIGS. 2A-2B show the extent of IFN-γ production in CD8+ spleen cells from mice vaccinated as described in the legend for FIG. 1, after in vitro stimulation with the SIINFEKL antigen peptide (SEQ ID NO:9). The analysis was done by intracellular staining for IFN-γ and analysis of the cells by flow cytometry. FIG. 2B is a bar diagram representation of the data shown in FIG. 2A.

FIGS. 3A-3B show the amount of IFN-γ and IL-2 production in total spleen cells from mice vaccinated as described in the legend for FIG. 1, after in vitro stimulation with the SIINFEKL antigen peptide (SEQ ID NO:9). The analysis was done by ELISA. FIGS. 3A and 3C show the results with and without SIINFEKL restimulation, the results are shown as the direct readout from the ELISA assay without correction according to the respective standard curves. FIGS. 3B and 3D shows the same data for the SIINFEKL stimulated samples, where the concentrations of IFN-γ and IL-2 have been calculated based on the respective standard curves.

FIGS. 4A-4F show routes of synthesis. FIG. 4A shows Scheme 1: synthetic route for synthesis of compound 5. Reagents and conditions: (a) propionic acid, reflux, 1 h (20%); (b) $NaNO_2$ (1.8 eq), TFA, rt, 3 min. 67%); (c) $SnCl_2.2H_2O$, conc. HCl, 60° C., 1 h (88%); (d) Bromoacetyl bromide, $Et_3N$, $CH_2Cl_2$, rt, 1 h (64%) (e) Piperazine, $CH_2Cl_2$, rt, 1 h (94%).

FIG. 4B shows Scheme 2. Synthesis of N-modified Chitosan derivatives (TPP-CS-TMA & TPP-CS-MP). Here A-represents $1^{st}$ batch compounds and B-presents $2^{nd}$ batch compounds. Reagents and conditions: (a) $MeSO_3H/H_2O$, 10° C.-rt, 1 h, (90%); (b) TBDMSCl, imidazole, DMSO, rt, 24 h (96%); (c) Bromoacetyl bromide, $Et_3N$, $CH_2Cl_2$, −20° C., 1 h (92%); (d) compound 5 i.e. TPP-NH-Pip (0.1 or 0.25 eq), $Et_3N$, $CHCl_3$, rt, 2 h (92-90%) (e) $NMe_3$ or 1-methyl piperazine, $CHCl_3$, rt, 24 h (f) TBAF, NMP, 55° C., 24 h or conc. HCl/MeOH, rt, 24 h.

FIG. 4C shows Scheme 3—Synthesis scheme for compounds 1, 3 20 and 21. Reactions and conditions: ((a) Propionic acid, reflux, 1 h, (20%); (b) $NaNO_2$ (1.8 eq.), TFA, rt, 3 min.; (c) $SnCl_2.2H_2O$, conc. HCl, 60° C., 1 h, (54%); ($d_1$) p-Toluenesulfonylhydrazide, $K_2CO_3$, pyridine, reflux, 24 h; ($d_2$) o-Chloranil, $CH_2Cl_2$, rt, (80%); (e) Chloroacetyl chloride, $Et_3N$, $CH_2Cl_2$, rt, 2 h, in situ-(f) Piperazine, $CH_2Cl_2$, rt, 12 h, (61%). All derivatives of compound 20 and 21 will contain the $TPCa_1$ and the $TPCa_2$ isomer. However only the $TPCa_1$ structure is shown in schemes and in the structure drawings.

FIG. 4D shows Scheme 4—synthesis scheme for compounds 22-28. Reactions and conditions: (a) Acetyl chloride, MeOH, reflux, 24 h, (87%); (b) $BF_3.Et_2O$, $CHCl_3$, rt, p-chloranil, 48 h, (14%); (c) 2N KOH (in MeOH), THF: Pyridine (10:1), reflux, 24 h (71%); ($d_1$) p-Toluenesulfonylhydrazide, $K_2CO_3$, Pyridine, reflux, 24 h; ($d_2$) o-chloranil, $CH_2Cl_2$: MeOH (75:25), rt, (70%); (e) EDCl.HCl, HOBT, $Et_3N$, N-Boc-piperazine 5, DMF, rt, 24 h (54%) (f) TFA, $CH_2Cl_2$, rt, 1 h (89%). All derivatives of compound 26-28 will contain the $TPCc_1$ and the $TPCc_2$ isomer. However, only the $TPCc_1$ structure is shown in schemes and in the structure drawings.

FIGS. 4E and 4F show Scheme 5A and 5B respectively. Reagents and conditions (6A): (a) compound 21 i.e. TPC-NH-Pip (0.1 eq), $Et_3N$, $CHCl_3$, 2 h (78%) (b) $NMe_3$ or 1-methyl piperazine, $CHCl_3$, rt, 24 h. Reagents and conditions (6b): a) compound 28 i.e. TPC-CO-Pip (0.1 eq), $Et_3N$, NMP, 75° C., 12 h (89%) (b) $NMe_3$ or 1-methyl piperazine, $CHCl_3$, rt, 24 h.

FIGS. 5A-5B shown the effect of the adjuvants poly(IC) and CpG. Mice were immunised with 10 μg of OVA, with 100 μg OVA, with 10 μg OVA and 150 μg $TPCS_{2a}$, with 10 μg OVA and 50 μg ODN2395 CpG oligonucleotide, with 10 μg OVA, 50 μg ODN2395 CpG oligonucleotide and 150 μg $TPCS_{2a}$, with 10 μg OVA and 50 μg Poly(IC), with 10 μg OVA, 50 μg Poly(IC) and 150 μg $TPCS_{2a}$ or left untreated. Mice receiving $TPCS_{2a}$ were illuminated. Mice were bled on day 7 and the frequency of OVA-specific CD8 T-cells was analysed by flow cytometry. On day 14 spleen cells were obtained and restimulated by SIINFEKL peptide (SEQ ID NO:9) and analysed by Interferon-gamma ELISA. FIG. 5A shows the average values (% antigen-specific, $CD44^+$ cells of the total $CD8^+$ cells) in blood at day 7 for the experimental groups (5 animals in each group, error bars: standard error of the mean). FIG. 5B shows results from interferon-gamma (IFN-gamma) ELISA after restimulation of day 14 spleen cells with SIINFEKL peptide (SEQ ID NO:9).

EXAMPLES

Materials and Methods

Mice

Figure 1A:
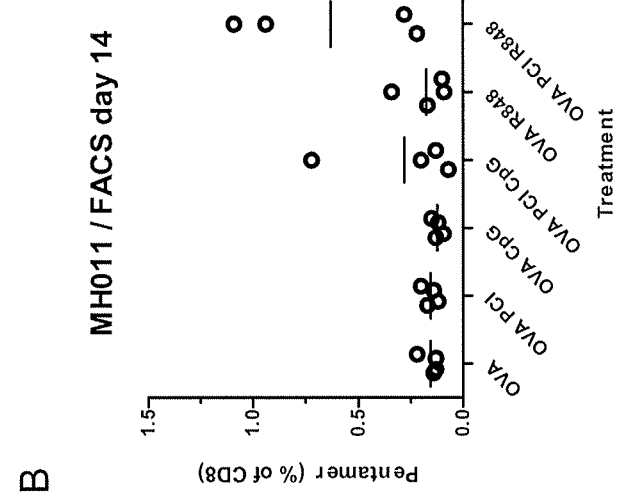

C57BL/6 mice were purchased from Harlan (Horst, The Netherlands). OT-I mice transgenic for the T-cell receptor that recognises the MHC class-I restricted epitope $OVA_{257-264}$ from ovalbumin (OVA) were bred in facilities at the University of Zurich (originally purchased from Taconic Europe (Ry, Denmark)). All mice were kept under specified pathogen-free (SPF) conditions, and the procedures performed were approved by Swiss Veterinary authorities. In the OT-1 mice, the gene for the T-cell receptor has been engineered in such a way that nearly all of the CD8+ T-cells in these mice (called OT-1 cells) will specifically recognize the specific peptide epitope (SIINFEKL) (SEQ ID NO:9) from the ovalbumin (OVA) antigen.

Immunisation Protocol

On day 0 female C57BL/6 mice were injected with $1.5 \times 10^6$ splenocytes from Rag2/OT-1 mice intravenously in the tail vein. In this way the mice that are vaccinated have a "background" of CD8 T-cells that can respond to the SIINFEKL-epitope (SEQ ID NO:9) from OVA if, and only if, this is properly presented on MHC class I on antigen presenting cells. Thus, the transfer of OT-1 cells "amplifies" the detection system in the vaccinated mice making it possible to easily assay for the effect of in vivo vaccination by measuring antigen specific CD8+ T-cells and IFN-γ and IL-2 production.

4 hours later the animals were vaccinated by intradermal injection at the abdomen (2×50 µl of solutions containing the ingredients specified below). 6 groups of 4 animals received total doses of:

Group 1:25 µg $TPCS_{2a}$ (Amphinex)+10 µg ovalbumin (OVA, Grade V, Sigma-Aldrich).
Group 2: 25 µg $TPCS_{2a}$+10 µg ovalbumin+60 µg CpG.
Group 3: 25 µg $TPCS_{2a}$+10 µg ovalbumin+100 µg R848 (resiquimod).
Group 4: 10 µg ovalbumin.
Group 5: 10 µg ovalbumin+60 µg CpG.
Group 6: 10 µg ovalbumin+100 µg R848 (resiquimod).

The CpG oligonucleotide used was the Type B 20-mer ODN 1826 (synthesised by Microsynth (Balgach, Switzerland)), with the sequence (5'-TCC ATG ACG TTC CTG ACG TT-3'; SEQ ID NO:4), with a fully phosphorothioated (PS-modified) backbone.

On day 1 the animals in groups 1, 2 and 3 were anaesthetized and illuminated for 6 minutes with blue light using a LumiSource lamp (PCI Biotech AS). The animals were illuminated about 18 h after injection of the antigen solution, the fluence rate of the illumination was about 13 mW/cm². On day 7 the mice were bled from the tail vein and the blood cells were stained with SIINFEKL pentamer (ProImmune), and CD8 and CD44 antibodies for flow cytometry analysis (see protocols below). On day 14 the mice were euthanized and the spleens were collected. One aliquot of the splenocytes was restimulated with the SIINFEKL peptide (SEQ ID NO:9) (EMC microcollections, Tuebingen, Germany), stained for intracellular IFN-γ expression and analysed by Flow cytometry analysis (see below). Another aliquot of the splenocytes was resuspended in cell culture medium, kept in this medium overnight (purely for practical reasons) without restimulation, stained by SIINFEKL-pentamer as described above and analysed by flow cytometry (see protocol below).

SIINFEKL-Pentamer-Staining of Spleen Cells

SIINFEKL-pentamer staining and flow cytometry on spleen cells was performed on cells that had been resuspended in cell medium and kept in this medium overnight (purely for practical reasons) without restimulation.

SIINFEKL-Pentamer Staining and Flow Cytometry 5-10 drops of whole tail blood were collected and 0.5 ml of Red Cell Lyse solution (Sigma) was added. After 5-6 minutes, cells were spun down and washed twice with 0.5 ml PBS. The cell pellet was resuspended in FACS buffer (2% FCS/PBS with 0.01% Na-azide), transferred to a U-formed 96 well plate and incubated with FcR-blocking antibodies (1.0 µl Anti-CD16/CD32 from Pharmingen) for 10 min on ice, (1 µl+49 µl FACS buffer). Without washing, the SIINFEKL-pentamer-PE (ProImmune; 5 ul per sample) was added, mixed and incubated at 37° C. for 15 min. Without washing, a fluorescence-labeled CD8 or CD44 was added to a final concentration of 1:100, and incubated on ice for 25-45 min. Cells were washed in 100 µl FACS buffer and suspended in 100 µl FACS buffer. Cells were analysed with FACSCanto.

Splenocyte Restimulation Ex Vivo

Splenocytes were isolated and prepared for intracellular staining by crushing the spleen and separating cells in 2% FCS/PBS, by agitation in lysis buffer (Sigma) for 1-2 minutes and washing in 2% FCS/PBS. 1 ml of the cell suspension in complete medium was added per well of a 24-well plate (500,000 cells/ml) and 5 µg/ml SIINFEKL (SEQ ID NO:9) was added to each well and incubated overnight at 37° C. Brefeldin A (1-2 µg/ml) was added to each well and incubated for 4 hours at 37° C. Cells were transferred to U-formed 96 well plates, washed in 2% FCS/PBS and resuspended in 50 µl FACS buffer with FcR-blocking antibodies (1.0 µl anti-CD16/CD32 from Pharmingen), and incubated on ice for 10 minutes. Without washing, cells were incubated with surface antibodies CD8 or CD44 for 20-45 min on ice (dark), washed in FACS buffer and fixed by resuspending in 100 ul paraformaldehyde (PFA) (1% in PBS) for 10-20 minutes on ice. Cells were washed in FACS buffer, resuspended in 100 µl NP40 (0.1% in PBS) and incubated for 3 minutes on ice. After washing in FACS buffer, a fluorescence-labeled interferon-gamma antibody was added and incubated for 35 min on ice in the dark. After washing and suspension in FACS buffer, the cells were analysed with FACSCanto using FlowJo 8.5.2 software (Tree Star, Inc., Ashland, Oreg.).

Flow Cytometry

The frequency of OVA-specific T-cells was determined by flow cytometry (FACSCanto from BD Biosciences, San Jose, USA). Before the flow cytometry run a compensation was performed using beads stained with each antibody separately. Before antibody staining, the red blood cells were lysed using Red Cell Lyse solution (Sigma). 10 000 $CD8^+$ events were recorded for each sample, and the percentage of SIINFEKL-pentamer positive cells was calculated using FlowJo 8.5.2 software from Tree Star, Inc. (Ashland, Oreg.) http://www.flowjo.com/.

ELISA

ELISA was performed using the Ready-set Go! kit (eBioscience) for the relevant molecules according to the manufacturer's instructions.

Example 1: Effect of TLR Ligands on In Vivo Vaccination with OVA

Mice were vaccinated in vivo by the immunisation protocol described above. Blood was isolated after 7 days and spleen after 14 days. Blood was analysed for antigen-specific CD8+ T cells and spleen cells were either analysed directly for antigen-specific CD8+ T-cells or for IFN-γ or IL-2 production after restimulation in vitro.

Level of Antigen-Specific T-Cells in Blood and Spleen

The level of antigen-specific T-cells was measured by flow cytometry, using a fluorescently labelled antigen-specific "pentamer" that binds specifically to the antigen-specific T-cells. The number of antigen specific CD8+ T-cells in % of the total CD8+ T-cells in the animal was determined (see the staining and flow cytometry analysis described in the immunisation protocol and details of SIINFEKL staining).

The endogenous T-cells serve as an internal control for the antigen-specificity of the effect, since a general stimulation effect on T-cells will affect also the endogenous T-cells not leading to an increase in the % of the antigen-specific cells. Typically the % of OT-1 cells was measured before vaccination and at time point(s) after vaccination. The effect of the antigen alone ("conventional vaccination") was compared to the effect of antigen+PCI.

Level of IFN-γ Production in Spleen Cells after Ex Vivo Stimulation with Antigen (Flow Cytometry)

Spleens removed on day 14 of vaccination were subject to splenocyte isolation and restimulation with SIINFEKL antigen peptide (SEQ ID NO:9) and intracellular staining for IFN-γ production for analysis of CD8+ T cells by flow cytometry as described in the protocols above.

Level of IFN-γ and IL-2 Production in Spleen Cells after Ex Vivo Stimulation with Antigen (ELISA)

Spleens removed on day 14 of vaccination were subject to splenocyte isolation and restimulation with SIINFEKL antigen peptide (SEQ ID NO:9) and IFN-γ and IL-2 production analysis by ELISA as described in the protocols above.

Results

Level of Antigen-Specific T-Cells in Blood and Spleen

Figure 1B:
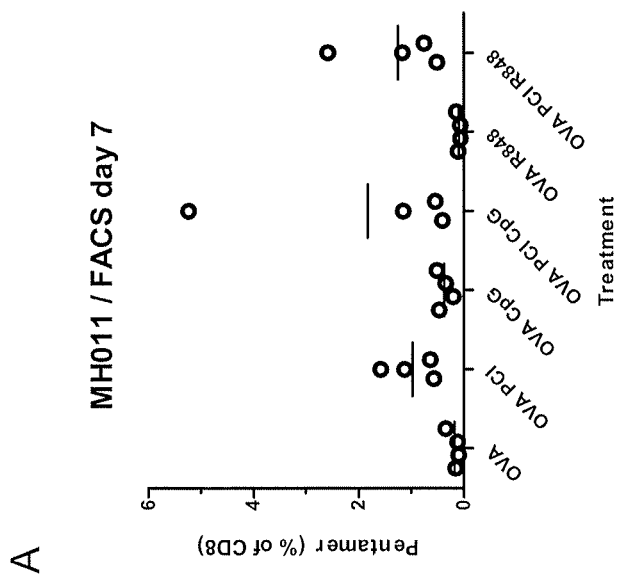
Figure 1C:
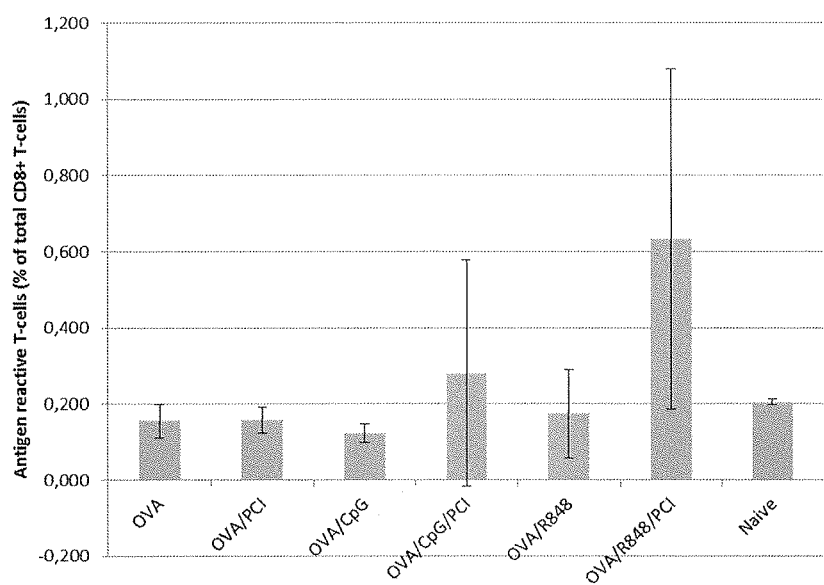

The results are shown in FIG. 1. It can be seen that when assayed at day 7 PCI induced a significantly better effect than the OVA antigen alone (A). The CpG oligonucleotide also improved vaccination over OVA alone, but not as much as PCI. R848 alone did not improve vaccination over OVA alone, rather it seemed to somewhat inhibit the effect of the vaccination. Combining PCI with either R848 or CpG improved vaccination as compared to the effect of PCI+OVA. This improvement was even more pronounced when analyzing the spleen cells 14 days after vaccination (B and C). It can be seen that at this time point the effect of the PCI+OVA treatment alone had returned to the background level, the same was the case for the groups with R848/CpG+OVA without PCI. However, in the two groups where R484 or CpG where combined with PCI a substantially better effect was observed, especially pronounced for R848.

Level of IFN-γ Production in Spleen Cells after Ex Vivo Stimulation with Antigen (Flow Cytometry)

Figure 2A:
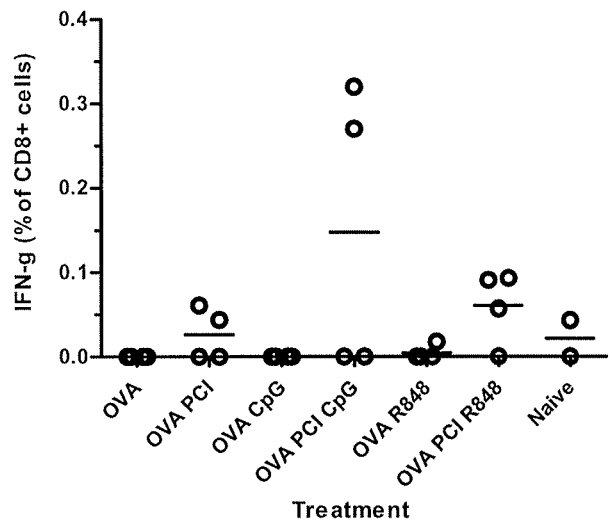
Figure 2B:
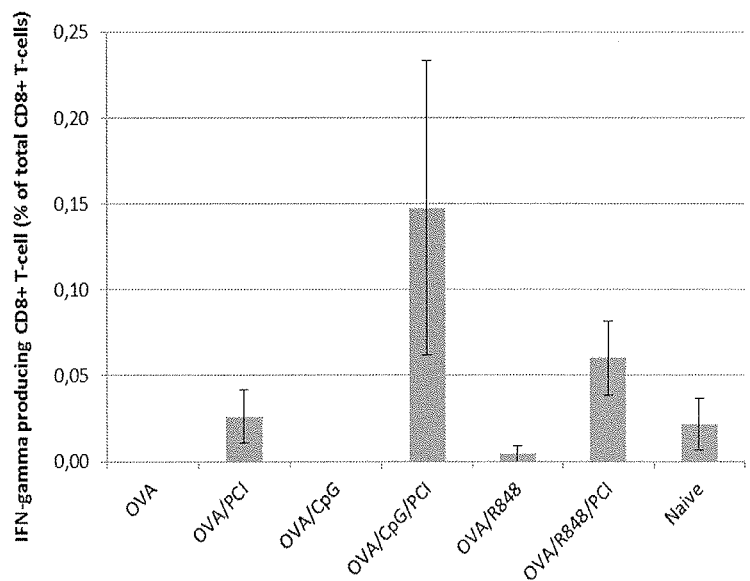

IFN-γ and IL-2 are cytokines produced by CD8+ T-cells after stimulation with antigen. The results are shown in FIG. 2. In accordance with the results shown in FIG. 1, FIG. 2 shows that the best effect was achieved by the combination of CpG/R848 and PCI, with CpG+PCI seemingly being better than R848+PCI when assaying for this parameter. It can also be seen that the antigen alone (OVA) gave no detectable effect, while OVA+PCI induced an observable effect. The groups with CpG/R848+OVA without PCI gave no (CpG) or only a barely detectable (R848) effect, while the combinations of OVA+CpG+PCI and OVA+R848+PCI, was about 6 times and 2.5 times better than OVA+PCI, respectively.

Level of IFN-γ Production in Spleen Cells after Ex Vivo Stimulation with Antigen (ELISA)

Figures 3A, 3B:
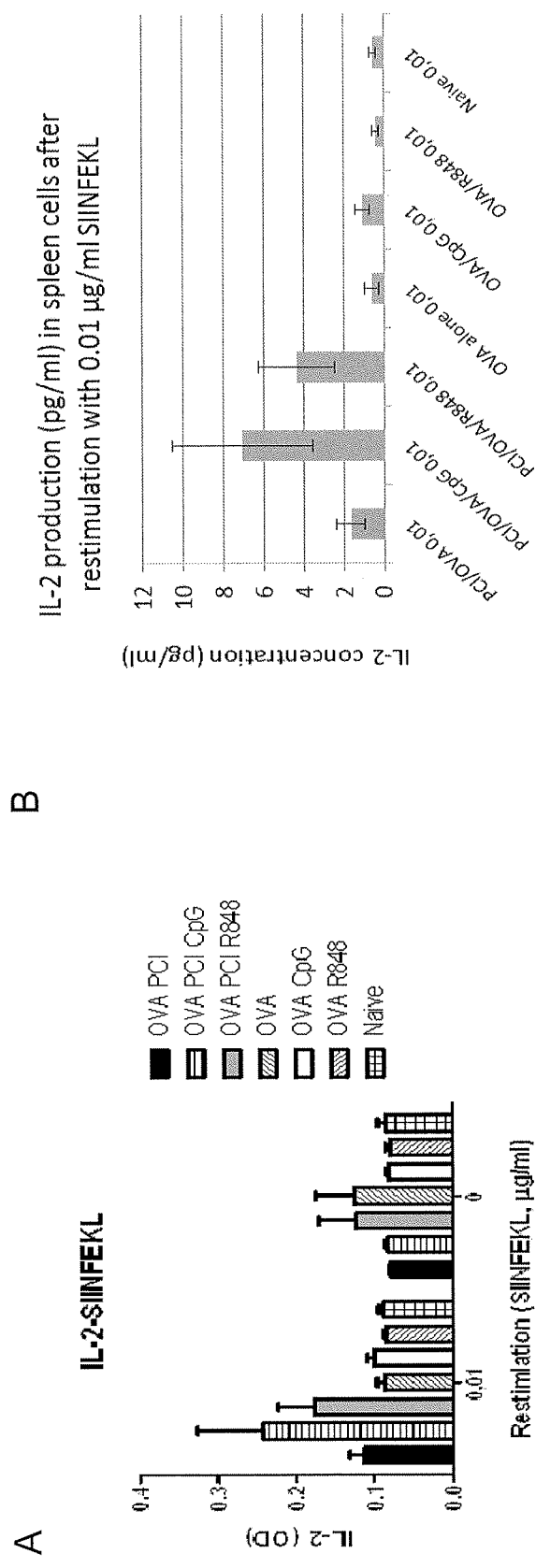
Figure 3C:
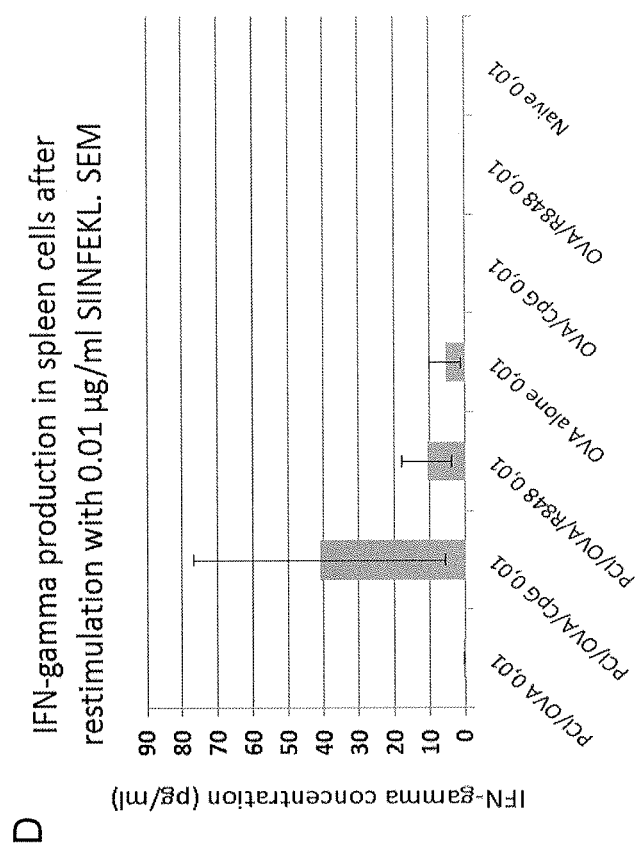
Figure 3D:
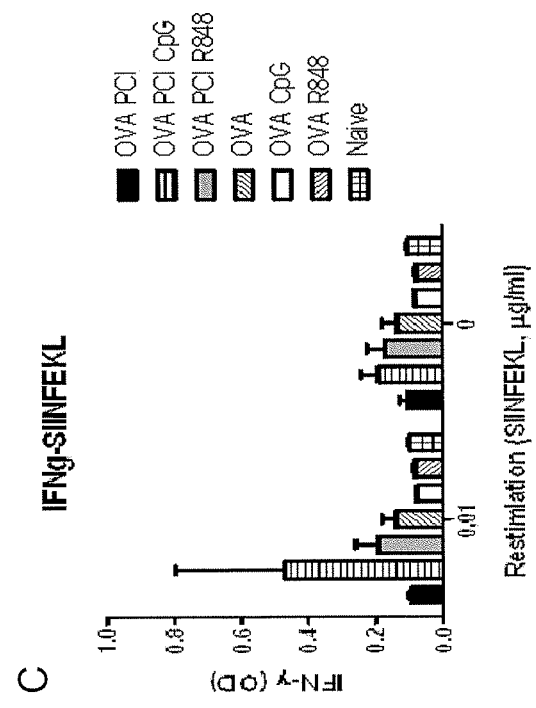
Figure 4A:
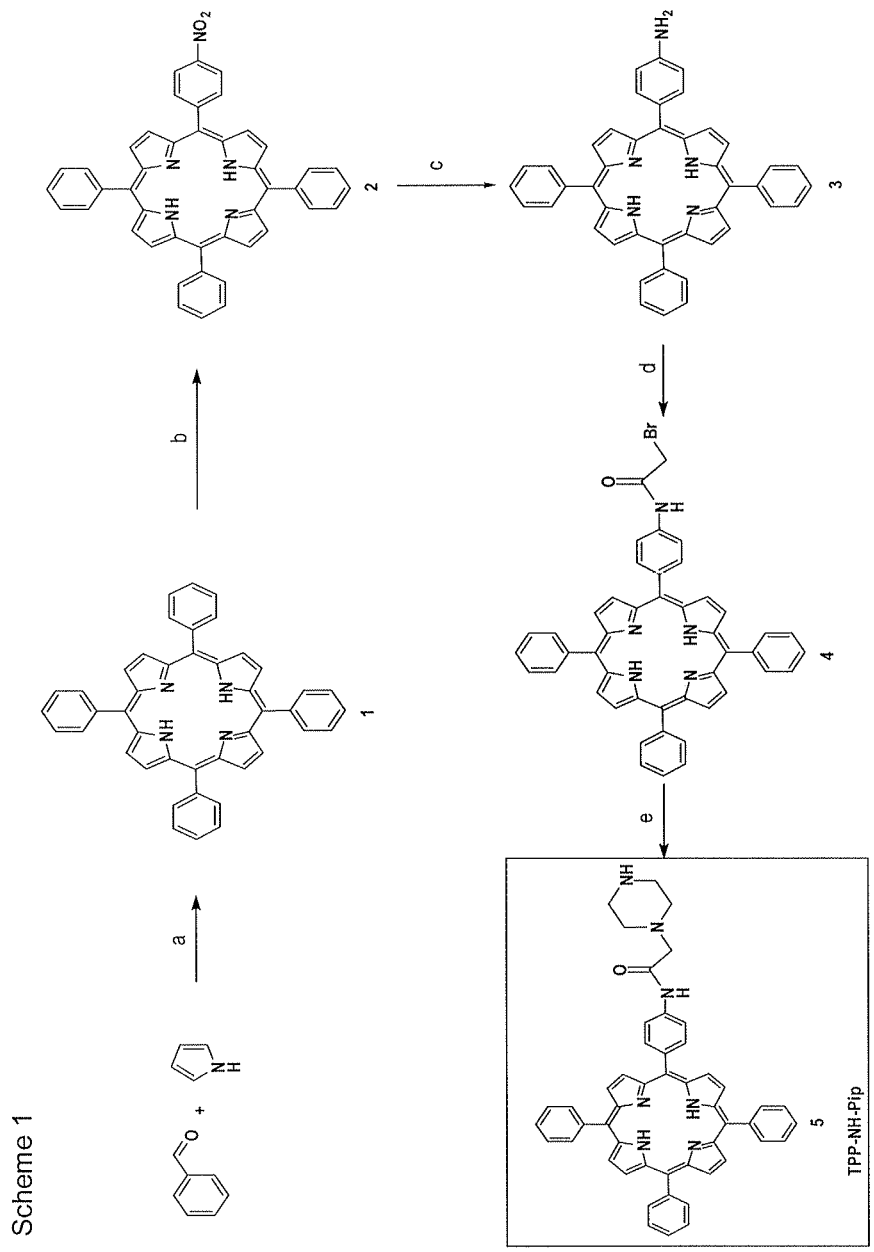
Figure 4B:
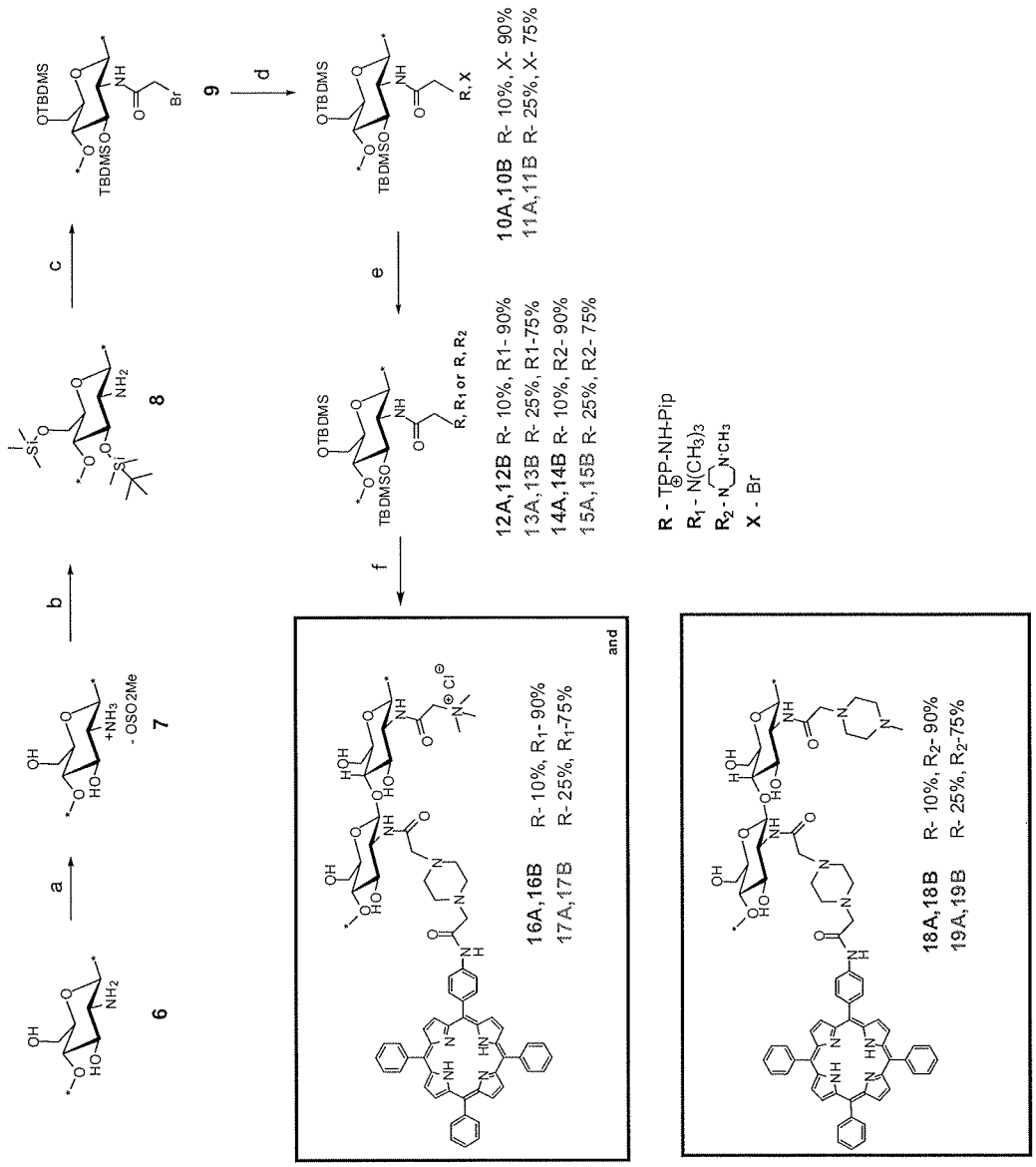
Figure 4C:
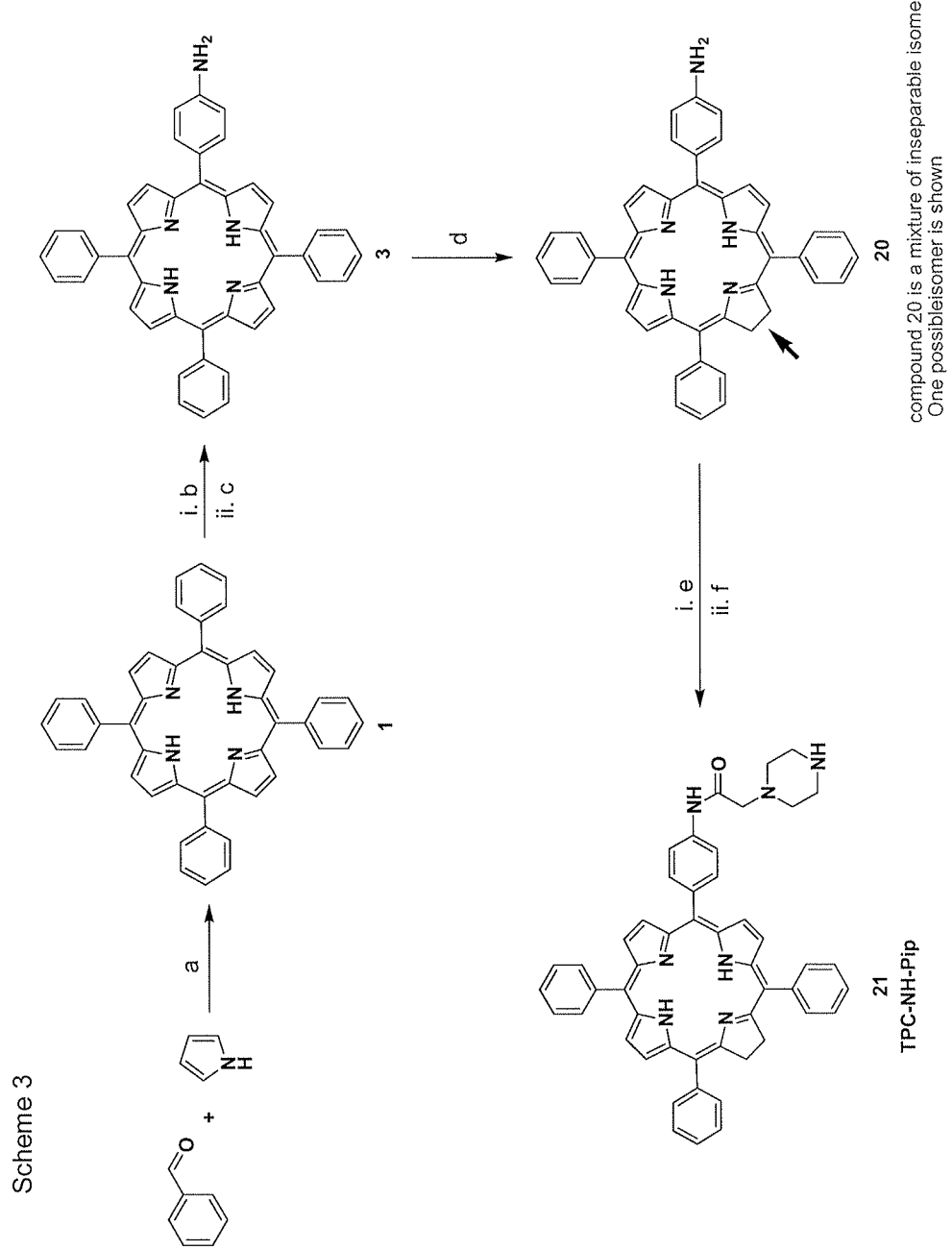
Figure 4D:
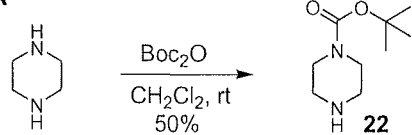
Figure 4D:
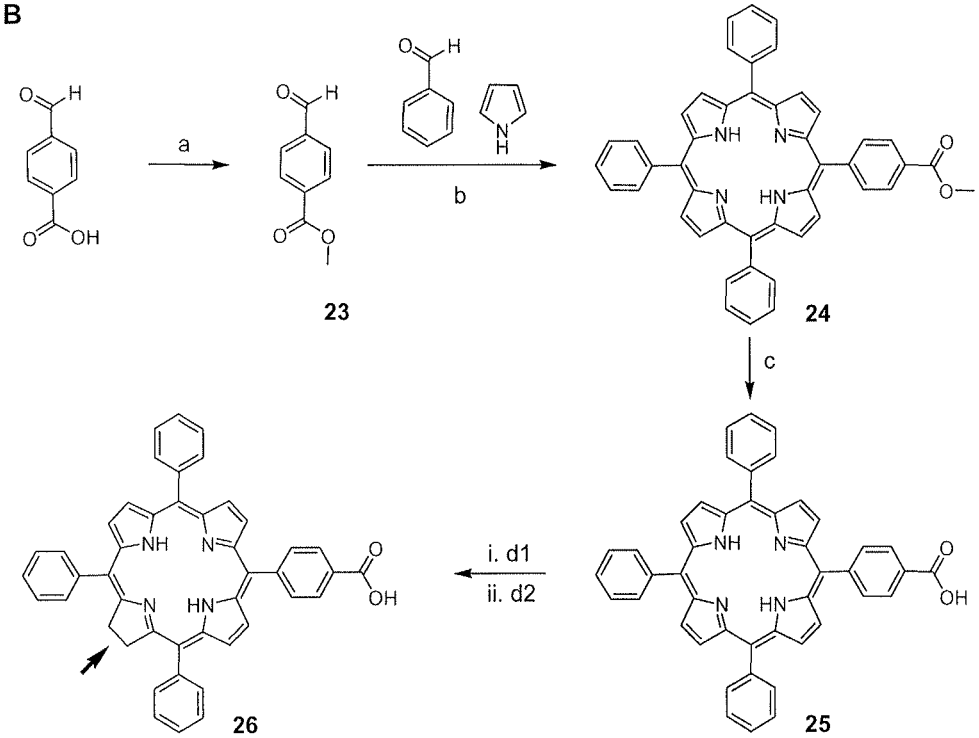
Figure 4D:
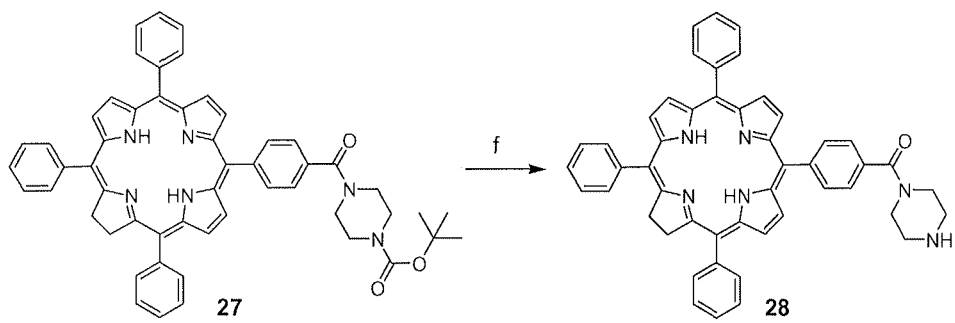
Figure 4E:
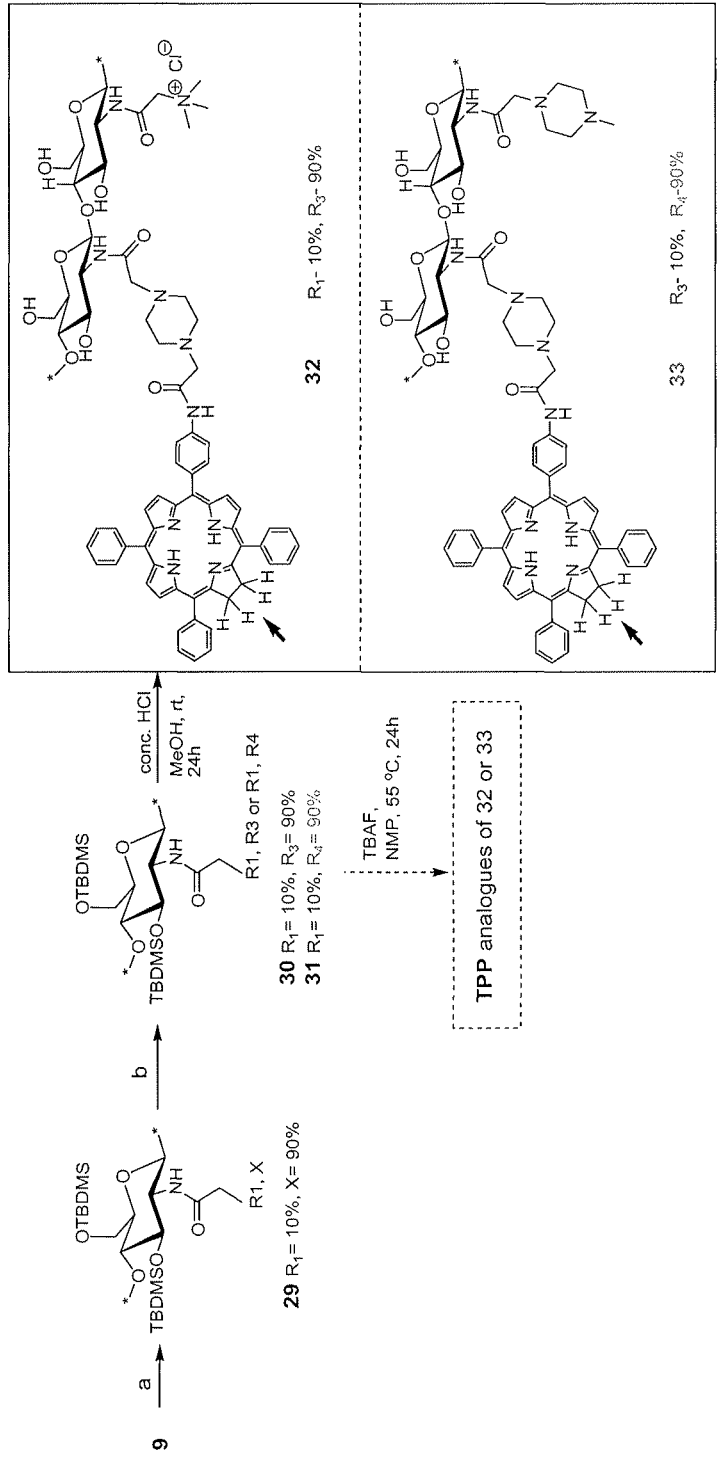
Figure 4F:
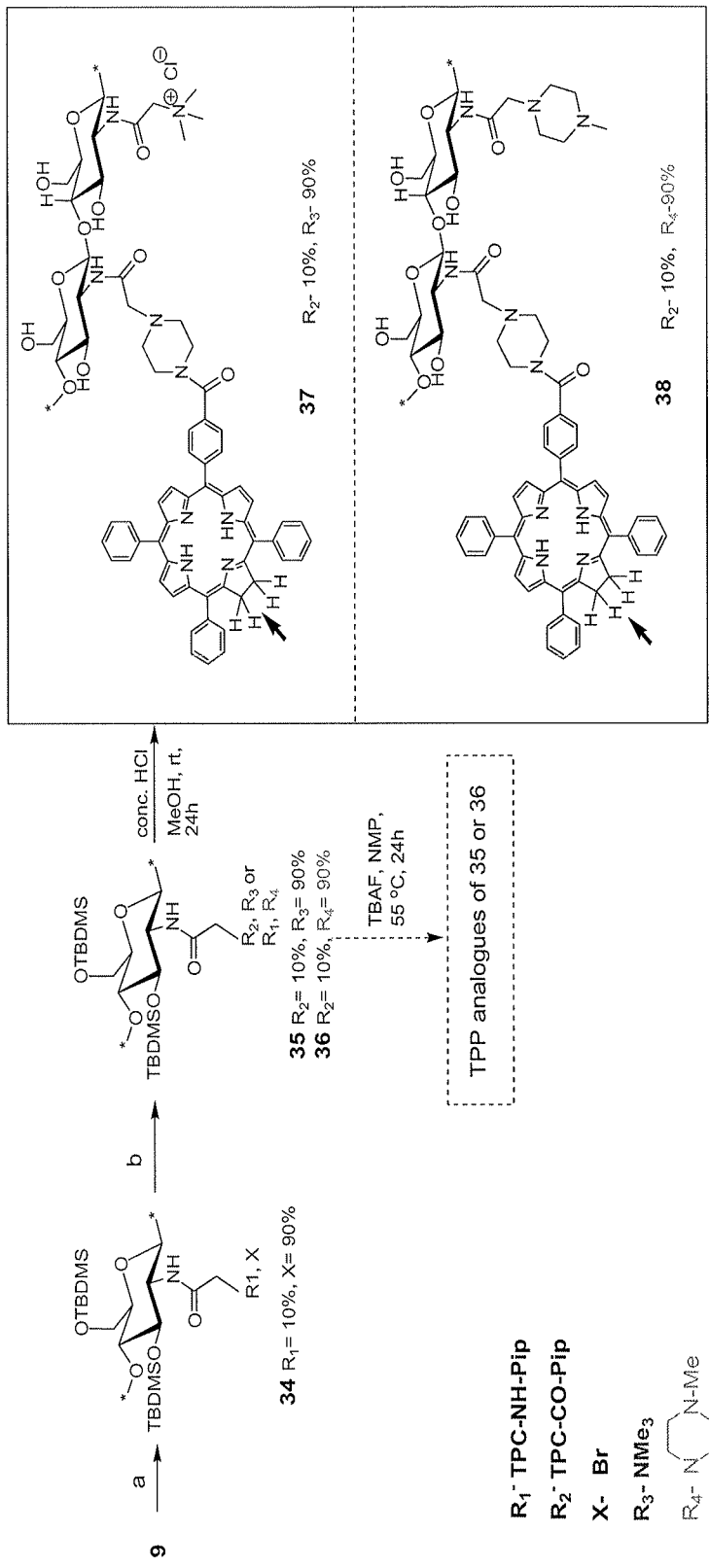

The results are shown in FIG. 3. FIG. 3 in panels A and C shows that both the IFN-γ and the IL-2 production was highest in the OVA+CpG/R848+PCI groups, and that the production was dependent on the stimulation by the SIINFEKL peptide antigen (SEQ ID NO:9), showing that it is an antigen specific effect. Panels B and D show that the effect in the CpG/R848+OVA+PCI groups was substantially better than in the other treatment groups.

Example 2: Effect of Other TLR Ligands on In Vivo Vaccination with OVA

The above methods are used to perform vaccination in vivo. Thus the above described methods may be performed in which 14 groups of 4 animals receive total doses of:

Group 1: 250 µg $TPCS_{2a}$ (Amphinex)+10 µg ovalbumin (OVA, Grade V, Sigma-Aldrich).
Group 2: 250 µg $TPCS_{2a}$+10 µg ovalbumin+50 µg LPS (*Porphyromonas Gingivalis*).
Group 3: 250 µg $TPCS_{2a}$+10 µg ovalbumin+50 µg LPS (*E. coli*).
Group 4: 250 µg $TPCS_{2a}$+10 µg ovalbumin+50 µg LPS (*Salmonella minnesota*).
Group 5: 250 µg $TPCS_{2a}$+10 µg ovalbumin+100 µg MPLA (*Salmonella minnesota*).
Group 6: 250 µg $TPCS_{2a}$+10 µg ovalbumin+1 mg Poly (I:C).
Group 7: 250 µg $TPCS_{2a}$+10 µg ovalbumin+1 mg ssPolyU.
Group 8: 10 µg ovalbumin.
Group 9: 10 µg ovalbumin+50 µg LPS (*Porphyromonas Gingivalis*).
Group 10: 10 µg ovalbumin+50 µg LPS (*E. coli*).
Group 11: 10 µg ovalbumin+50 µg LPS (*Salmonella minnesota*).
Group 12: 10 µg ovalbumin+100 µg MPLA (*Salmonella minnesota*).
Group 13: 10 µg ovalbumin+1 mg Poly(I:C).
Group 14: 10 µg ovalbumin+1 mg ssPolyU.
Poly(I:C), LPS, MPLA and ssPolyU are all obtained from Invivogen.

Example 3: Effect of Poly(IC) and CpG on In Vivo Vaccination with OVA

Materials and Methods

Animals

C57BL/6 mice were purchased from Harlan (Horst, The Netherlands). CD8 T-cell receptor transgenic OT-I mice (B6.129S6-Rag2tm1Fwa Tg(TcraTcrb)1100Mjb) were purchased from Taconic Europe (Ry, Denmark) or from Jackson Laboratories (Bar Harbor, Me.). The OT-I CD8 T cells recognise the $H-2K^b$-restricted epitope SIINFEKL (SEQ ID NO:9) from ovalbumin (OVA, aa257-264). All mice were kept under SPF conditions, and the procedures performed were approved by the veterinary authorities in Switzerland and Norway.

Materials and Cells

Chicken OVA was purchased from Sigma-Aldrich (Buchs, Switzerland), the SIINFEKL peptide (SEQ ID NO:9)

from EMC microcollections (Tuebingen, Germany), and Poly(IC) (high MW) and CpG oligonucleotide ODN2395 from InvivoGen (San Diego, USA). The photosensitiser tetraphenyl chlorine disulfonate (TPCS$_{2a}$) was from PCI Biotech (Lysaker, Norway). OVA, TPCS$_{2a}$ and, when relevant, Poly(IC) were mixed in PBS, kept light protected, and administered to mice within 60 minutes of preparation. TPCS$_{2a}$ was activated by illumination with LumiSource™ (PCI Biotech).

Intradermal Photosensitisation and Immunisation of Mice

One day prior to the immunisation, spleens and lymph nodes were isolated from female OT-1 mice, and erythrocytes were removed by lysis (RBC Lysing Buffer Hybri-Max from Sigma-Aldrich) from the homogenised cell suspensions. The remaining cells were washed in PBS, filtered through 70 micron nylon strainers, and 2×10$^6$ OT-1 cells were administered by intravenous injection into recipient female C57BL/6 mice; the adoptive transfer of SIINFEKL-specific CD8 T cells facilitates monitoring of the immune response by flow cytometry. One day or 8 hours later, mice were bled by tail bleeding, and the blood was collected in heparin-containing tubes for analysis of the baseline frequency of OVA-specific CD8 T cells.

Then, the mice were shaved on the abdominal area, and the vaccines, consisting of OVA or of different mixtures of OVA, TPCS$_{2a}$, Poly(IC) (50 μg) or CpG oligonucleotide (50 μg) were injected intradermally using syringes with 29G needles. The vaccines were kept light protected and used within 60 minutes of preparation. The vaccines were given in two injections of 50 μl each, on the left and right side of the abdominal mid line. OVA was used in a dose of 10 or 100 μg, and the TPCS$_{2a}$ dose was 150 μg. 18 hours after the vaccine injection, the mice were anaesthetised by intraperitoneal injection of a mixture of ketamine (25 mg/kg body weight) and xylazin (4 mg/kg) and placed on the LumiSource light source (for illumination and activation of the photosensitiser TPCS$_{2a}$). The illumination time was 6 minutes.

On days 7 and 14 thereafter mice were bled by tail bleeding and erythrocytes were removed by lysis, before analysis of antigen-specific CD8 T cells by flow cytometry. At the end of the experiment (day 14), the mice were euthanized and the splenocytes analysed ex vivo.

Analysis of Immune Responses

The frequency of OVA-specific CD8 T-cells in blood was monitored by staining the cells with anti-CD8 antibody and H-2K$^b$/SIINFEKL Pro5 pentamer (Proimmune, Oxford, UK) for analysis by flow cytometry. The activation status of the cells was further analysed by testing the expression of CD44 by flow cytometry. The cells were analysed using FACSCanto (BD Biosciences, San Jose, USA) and analysed using FlowJo 8.5.2 software (Tree Star, Inc., Ashland, Oreg.).

For ELISA analysis 2×10$^5$ splenocytes were re-stimulated in 96-well plates with 0.005 μg/ml of the SIINFEKL peptide (SEQ ID NO:9). After 72 hours, supernatants were collected and analysed for IFN-γ by ELISA (eBioscience—performed according to the manufacturer's instructions).

Poly(IC) and CpG Experiment.

The experiment was performed as described under Materials and Methods, and mouse blood samples from day 7 after vaccination were analysed by flow cytometry as described. Spleen cells from day 14 were restimulated by SIINFEKL peptide (SEQ ID NO:9) and analysed by Interferon-gamma ELISA as described. All mice received OT-1 cells as described.

The following experimental groups were included:
1. Untreated: Mice received OT-1 cells, but were not vaccinated or illuminated.
2. OVA: Mice were vaccinated with 10 μg of OVA. They were not illuminated.
3. OVA 100 μg: Mice were vaccinated with a mixture of 100 μg OVA. They were not illuminated.
4. OVA 10 μg PCI: Mice were vaccinated with a mixture of 10 μg OVA+150 μg TPCS$_{2a}$. Illuminated as described.
5. CpG OVA: Mice were vaccinated with a mixture of 10 μg OVA+50 μg ODN2395 CpG oligonucleotide. They were not illuminated.
6. CpG OVA/PCI: Mice were vaccinated with a mixture of 10 μg OVA+50 μg ODN2395 CpG oligonucleotide+150 μg TPCS$_{2a}$. Illuminated as described.
7. Poly(IC) OVA: Mice were vaccinated with a mixture of 10 μg OVA+50 μg Poly(IC). They were not illuminated.
8. Poly(IC) OVA/PCI: Mice were vaccinated with a mixture of 10 μg OVA+50 μg Poly(IC)+150 μg TPCS$_{2a}$. Illuminated as described.

Figure 5A:
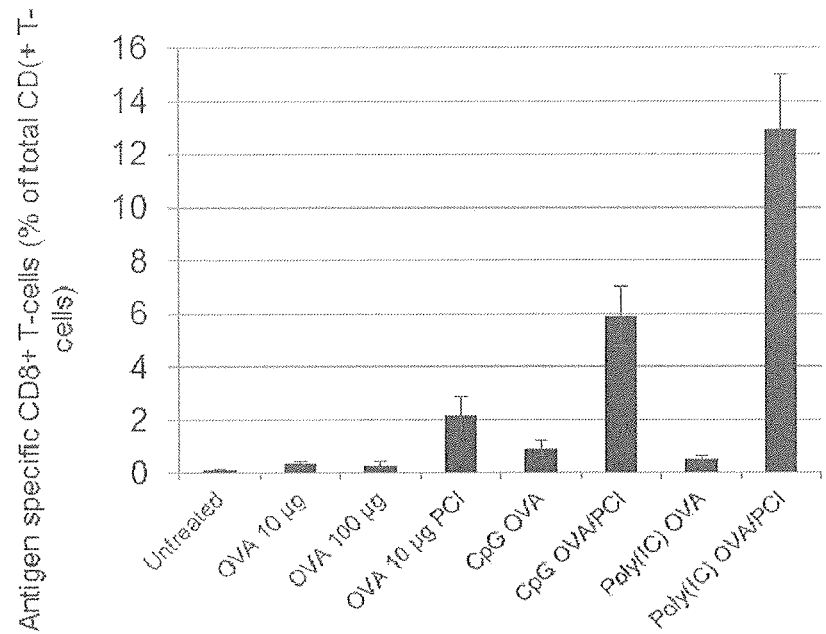

FIG. 5A shows the average values (% antigen-specific, CD44$^+$ cells of the total CD8$^+$ cells) for the experimental groups. It can be seen that the CpG and Poly(IC) adjuvants when used alone had only a very modest (for CpG) or no significant (for Poly(IC) effect, and that PCI used alone was substantially more potent than either of these adjuvants. However, a clear synergistic effect was seen when PCI was used in combination with CpG or Poly(IC), and was most prominent for the combination PCI+Poly(IC).

Figure 5B:
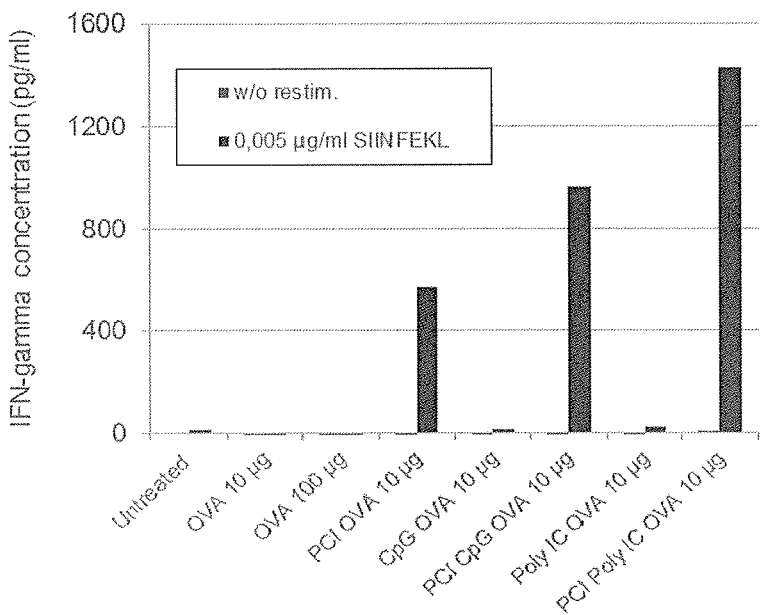

FIG. 5B shows the results from interferon-gamma (IFN-gamma) ELISA after restimulation of spleen cells with SIINFEKL peptide (SEQ ID NO:9). Firstly it can be seen that the IFN-gamma production was totally dependent on restimulation (bars from unstimulated cells are barely visible) showing that the production was strictly antigen specific. It can also be seen that while there was virtually no effect with the cells from the CpG or Poly(IC) groups (nor with OVA alone), in all the PCI-treated groups a strong effect of restimulation could be observed, again with a synergistic effect in the PCI+CpG and the PCI+Poly(IC) groups, with the latter representing the better combination.

For Examples 4 to 16 the Following Materials and Methods were Employed: Animals

C57BL/6 mice were purchased from Harlan (Horst, The Netherlands). CD8 T-cell receptor transgenic OT-I mice (B6.129S6-Rag2tm1Fwa Tg(TcraTcrb)1100Mjb) from Taconic Europe (Ry, Denmark) or from Jackson Laboratories (Bar Harbor, Me.). The OT-I CD8 T cells recognise the H-2K$^b$-restricted epitope SIINFEKL from ovalbumin (OVA, aa257-264; SEQ ID NO:9). All mice were kept under SPF conditions, and the procedures performed were approved by the veterinary authorities in Switzerland and Norway.

Materials and Cells

Chicken OVA was purchased from Sigma-Aldrich (Buchs, Switzerland), the SIINFEKL peptide (SEQ ID NO:9) from EMC microcollections (Tuebingen, Germany), and the TRP-2 (sequence SVYDFFVWL; SEQ ID NO:10), gp100 (sequence KVPRNQDWL; SEQ ID NO:11) and HPV 67 E7 (sequence GQAEPDRAHYNIVTFCCKCDSTLRL-CVQSTHVDIR (SEQ ID NO:1), the CD8 epitope is underlined) was obtained from United Peptides (Herndon, Va.). Poly(IC), CpG oligonucleotide ODN2395, MPLA-SM, imiquimod and resiquimod was from InvivoGen (San Diego, USA). The photosensitiser tetraphenyl chlorin disulfonate (TPCS$_{2a}$) was from PCI Biotech (Lysaker, Norway).

SIINFEKL (SEQ ID NO:9), TRP-2 and HPV pentamers were from Proimmune (Oxford, UK), (Proimmune peptide codes 093, 185 and 502H, respectively).

Intradermal Photosensitisation and Immunisation of Mice with Adoptively Transferred OT-1 Cells.

One day prior to the immunisation, spleens and lymph nodes were isolated from female OT-1 mice, and erythrocytes were removed by lysis (RBC Lysing Buffer Hybri-Max from Sigma-Aldrich) from the homogenised cell suspensions. The remaining cells were washed in PBS, filtered through 70 micron nylon strainers, and $2\times10^6$ OT-1 cells were administered by intravenous injection into recipient female C57BL/6 mice; the adoptive transfer of SIINFEKL-specific CD8 T cells facilitates monitoring of the immune response by flow cytometry. One day or 8 hours later, mice were bled by tail bleeding, and the blood was collected in heparin-containing tubes for analysis of the baseline frequency of OVA-specific CD8 T cells.

For intradermal immunisation the mice were shaved on the abdominal area, and the vaccines, consisting of OVA or of mixtures of OVA, $TPCS_{2a}$ and different adjuvants were injected intradermally using syringes with 29 G needles. The vaccines were kept light protected and used within 60 minutes of preparation. The vaccines were given in two injections of 50 µl each, on the left and right side of the abdominal mid line. 18 hours after the vaccine injection, the mice were anaesthetised by intraperitoneal injection of a mixture of ketamine (25 mg/kg body weight) and xylazin (4 mg/kg) and illuminated as described below according to the individual experiments.

On day 7 mice were bled by tail bleeding and erythrocytes were removed by lysis, before analysis of antigen-specific CD8 T cells by flow cytometry. At the end of the experiment (day 14), the mice were euthanized and the splenocytes analysed ex vivo.

Intradermal Photosensitisation and Immunisation of Normal Mice.

The mice were shaved on the abdominal area, and the vaccines, consisting of OVA protein or different peptide antigens (specified under individual experiments), $TPCS_{2a}$ and different vaccine adjuvants were injected intradermally using syringes with 29 G needles. The vaccines were kept light protected and used within 60 minutes of preparation. The vaccines were given in two injections of 50 µl each, on the left and right side of the abdominal mid line. Antigen and $TPCS_{2a}$ were used in different doses (specified under the individual experiments). At a specified time point after vaccine injection (usually 18 hours, but different in some experiments), the mice were anaesthetised by intraperitoneal injection of a mixture of ketamine (25 mg/kg body weight) and xylazin (4 mg/kg) and illuminated as described according to the individual experiments.

On day 7 (or in some cases day 6) after immunisation mice were bled by tail bleeding and erythrocytes were removed by lysis, before analysis of antigen-specific CD8 T cells by flow cytometry. In some experiments the mice received multiple (2 or 3) immunisations at time points specified according to the individual experiments. In these cases blood samples were drawn 6 or 7 days after immunisation and analysed by flow cytometry as described below.

Illumination of Immunised Mice.

In some experiments $TPCS_{2a}$ was activated by illumination with LumiSource™ (PCI Biotech). In general illumination with LumiSource was performed for 6 min, 18 hours after immunisation, but with some variation in some experiments as described below. In other experiments an LED-based illumination device emitting blue light was used as described below (PCI Biotech AS), and in some experiments the PCI 652 nm laser system SN 576003 diode laser (PCI Biotech AS) was used for illumination.

Analysis of Immune Responses by Pentamer Staining.

The frequency of antigen specific CD8 T-cells in blood was monitored by flow cytometry after staining the cells with anti-CD8 and anti-CD44 antibodies and different pentamers corresponding to the antigen used. The activation status of the cells was analysed by testing the expression of CD44 by flow cytometry. The cells were analysed using FACSCanto (BD Biosciences, San Jose, USA) and analysed using FlowJo 8.5.2 software (Tree Star, Inc., Ashland, Oreg.).

Analysis of Immune Responses by ELISA.

For ELISA analysis $2\times10^5$ splenocytes were re-stimulated in 96-well plates with 0.005 µg/ml of the SIINFEKL peptide (SEQ ID NO:9). After 72 hours, supernatants were collected and analysed for IFN-γ by ELISA (eBioscience—performed according to the manufacturer's instructions).

Example 4: Effect of PCI with OVA and Poly(IC) in Normal Mice

The experiment was performed as described above for vaccination of normal mice. The animals were immunised at day 0 and at day 14 with a mixture of 200 µg OVA protein, 150 µg $TPCS_{2a}$ and 50 µg poly(IC) as specified below. Illumination for 6 minutes was performed with the LumiSource illumination device, 18 hours after immunisation. Blood samples from day 7 after each immunisation were stained by SIINFEKL pentamer, CD8 and CD44 antibodies, and analysed by flow cytometry as described. The following experimental groups were included:

1. Untreated: Mice were not immunised or illuminated.
2. OVA 200: Mice were immunised with 200 µg of OVA. They were not illuminated.
3. OVA 200/PCI: Mice were immunised with a mixture of 200 µg OVA and 150 µg $TPCS_{2a}$ and illuminated.
4. OVA 200/poly(IC): Mice were immunised with a mixture of 200 µg OVA and 50 µg poly(IC). They were not illuminated.
5. OVA 200/poly(IC): Mice were immunised with a mixture of 200 µg OVA, 150 µg $TPCS_{2a}$ and 50 µg poly(IC) and illuminated.

Figure 6:
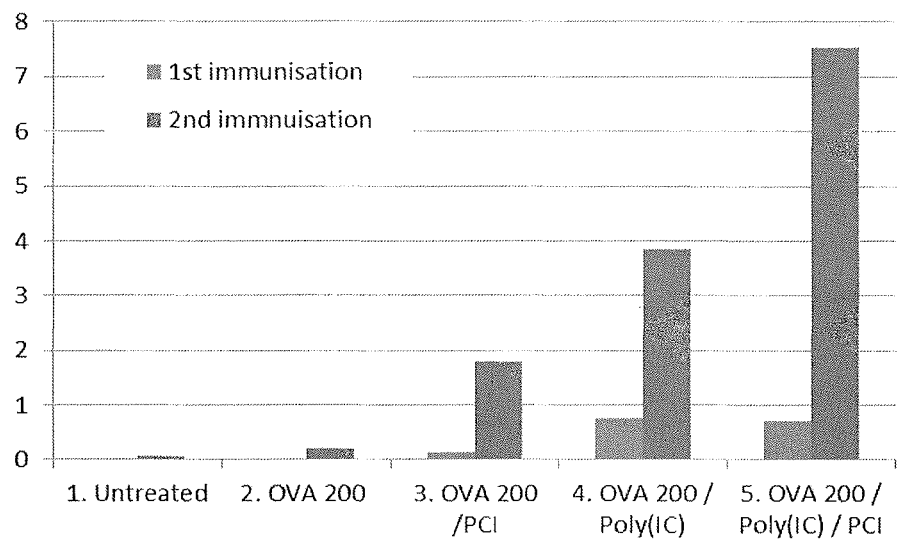
FIG. 6 shows the average values (% antigen-specific, CD44+ cells of the total CD8+ cells) after the $1^{st}$ and $2^{nd}$ immunisation of mice with OVA and poly(IC).

FIG. 6 shows the average values (% antigen-specific, CD44+ cells of the total CD8+ cells) for the experimental groups (5 animals in each group) after the $1^{st}$ and $2^{nd}$ immunisation. It can be seen that particularly after the $2^{nd}$ immunisation the combination of PCI and poly(IC) (group 5) gave substantially better immunisation than only poly(IC) (group 4) or only PCI (group 3).

Example 5: Effect of PCI with SIINFEKL and Poly(IC) in Normal Mice

The experiment was performed as described above for vaccination of normal mice. The animals were immunised at day 0 and at day 15 with a mixture of 100 µg SIINFEKL peptide (SEQ ID NO:9), 100 µg $TPCS_{2a}$ and 10 µg poly(IC) as specified below. Illumination for 6 minutes was performed with the LumiSource illumination device, 18 hours after immunisation. Blood samples from day 7 after each immunisation were stained by SIINFEKL pentamer, CD8 and CD44 antibodies, and analysed by flow cytometry as described. The following experimental groups were included:

1. Untreated: Mice were not immunised or illuminated.
2. SIIN 100: Mice were immunised with 100 µg of SIINFEKL peptide (SEQ ID NO:9). They were not illuminated.

3. SIIN 100/PCI: Mice were immunised with a mixture of 100 µg of SIINFEKL peptide (SEQ ID NO:9) and 100 µg TPCS$_{2a}$ and illuminated.
4. SIIN 100/poly(IC): Mice were immunised with a mixture of 100 µg of SIINFEKL peptide (SEQ ID NO:9) and 10 µg poly(IC). They were not illuminated.
5. SIIN 100/poly(IC)/PCI: Mice were immunised with a mixture of 100 µg of SIINFEKL peptide (SEQ ID NO:9), 100 µg TPCS$_{2a}$ and 10 µg of Poly(IC) and illuminated.

Figure 7:
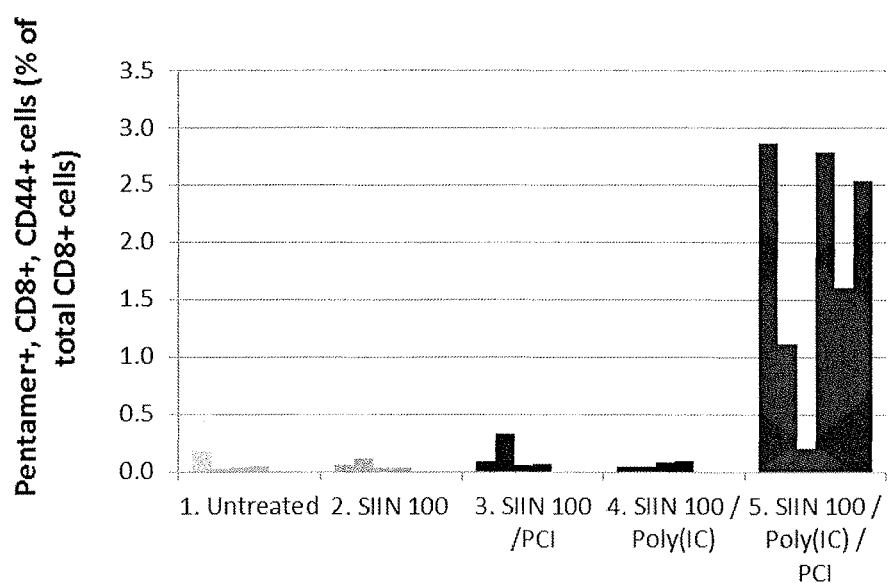
FIG. 7 shows the values for the individual animals in the experiment after the $2^{nd}$ immunisation (% antigen-specific, CD44+ cells of the total CD8+ cells) (error bars are standard deviation) after the $2^{nd}$ (day 22) immunisation.

FIG. 7 shows the values for the individual animals in the experiment after the 2$^{nd}$ immunisation, showing that with the PCI+Poly(IC) combination (group 5) all the animals responded to the immunisation, while in the other groups there was only one weakly responding animal (in the SIIN 100/PCI group).

Example 6: Effect of PCI with Melanoma Antigen Peptides and Poly(IC) in Normal Mice The experiment was performed as described above for vaccination of normal mice. The animals were immunised at day 0 and at day 14 with a mixture of TRP-2 peptide and gp-100 peptide (50 µg of each), 100 µg TPCS$_{2a}$ and 10 µg poly(IC) as specified below. Illumination for 6 min was performed with the LumiSource illumination device, 18 hours after immunisation. Blood samples from day 7 after each immunisation were stained with TRP-2 pentamers, CD8 and CD44 antibodies, and analysed by flow cytometry as described. The following experimental groups were included:
1. Untreated TRP-2: Mice were not immunised or illuminated, blood samples were stained with TRP-2 pentamer.
2. TRP-2/poly(IC): Mice were immunised with the mixture of TRP-2 and gp100 peptides and 10 µg poly(IC). They were not illuminated. Blood samples were stained with TRP-2 pentamer.
3. TRP-2/PCI: Mice were immunised with the mixture of TRP-2 and gp100 peptides and 100 µg TPCS$_{2a}$ and illuminated. Blood samples were stained with TRP-2 pentamer.
4. TRP-2/poly(IC)/PCI: Mice were immunised with the mixture of TRP-2 and gp100 peptides, 100 µg TPCS$_{2a}$ and 10 µg poly(IC) and illuminated. Blood samples were stained with TRP-2 pentamer.

Figure 8:
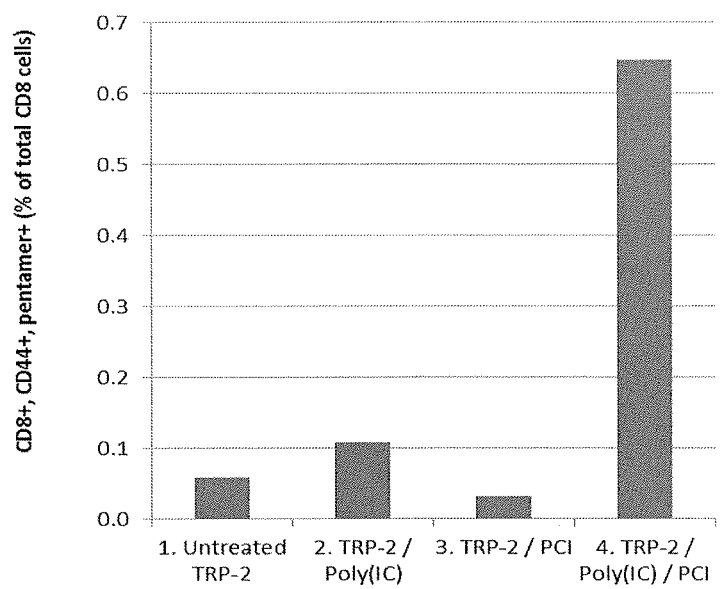
FIG. 8 shows the average values (% antigen-specific, CD44+ cells of the total CD8+ cells) for the TRP-2 pentamer stained experimental groups after the $2^{nd}$ immunisation.

FIG. 8 shows the average values (% antigen-specific, CD44+ cells of the total CD8+ cells) for the TRP-2 pentamer stained experimental groups after the 2$^{nd}$ immunisation. It can be seen that when the TRP-2 antigen was used with poly(IC) alone (group 2) or with PCI alone (group 3) no significant increase in antigen-specific cells were observed over what was seen in untreated animals. In comparison the combination of poly(IC) and PCI (group 4) gave a clear synergistic effect leading to a significant increase in the number of antigen-specific CD8+ T-cells.

Example 7: Analysis of PCI with OVA and Poly(IC) in Normal Mice with Red Light Illumination The experiment was performed as described for vaccination of normal mice under Materials and Methods. The animals were immunised at day 0 and at day 14 with a mixture of 10 or 100 µg OVA protein, 150 µg TPCS$_{2a}$ and 10 or 50 µg poly(IC) as specified below. Illumination was performed with the PCI 652 nm laser system SN 576003 diode laser with a light dose of 0.3 J/cm$^2$, delivered with a fluence rate of 0.81 mW/cm$^2$ (i.e. Illumination time about 6 min). Blood samples from day 7 after each immunisation were stained by SIINFEKL pentamer, CD8 and CD44 antibodies, and analysed by flow cytometry as described. The following experimental groups were included:
1. Untreated: Mice were not immunised or illuminated.
2. OVA 10: Mice were immunised with 10 µg of OVA. They were not illuminated.
3. OVA 100: Mice were immunised with 100 µg of OVA. They were not illuminated.
4. OVA 10/red light PCI: Mice were immunised with a mixture of 10 µg OVA and 150 µg TPCS$_{2a}$ and illuminated.
5. OVA 100/red light PCI: Mice were immunised with a mixture of 100 µg OVA and 150 µg TPCS$_{2a}$ and illuminated.
6. OVA 10/red light PCI+poly(IC): Mice were immunised with a mixture of 10 µg OVA, 150 µg TPCS$_{2a}$ and 50 µg poly(IC) (1$^{st}$ vaccination) or 10 µg poly(IC) (2$^{nd}$ vaccination), and Illuminated.
7. OVA 100/red light PCI+poly(IC): Mice were immunised with a mixture of 100 µg OVA, 150 µg TPCS$_{2a}$ and 50 µg poly(IC) (1$^{st}$ immunisation) or 10 µg poly(IC) (2$^{nd}$ immunisation), and Illuminated.

Figure 9:
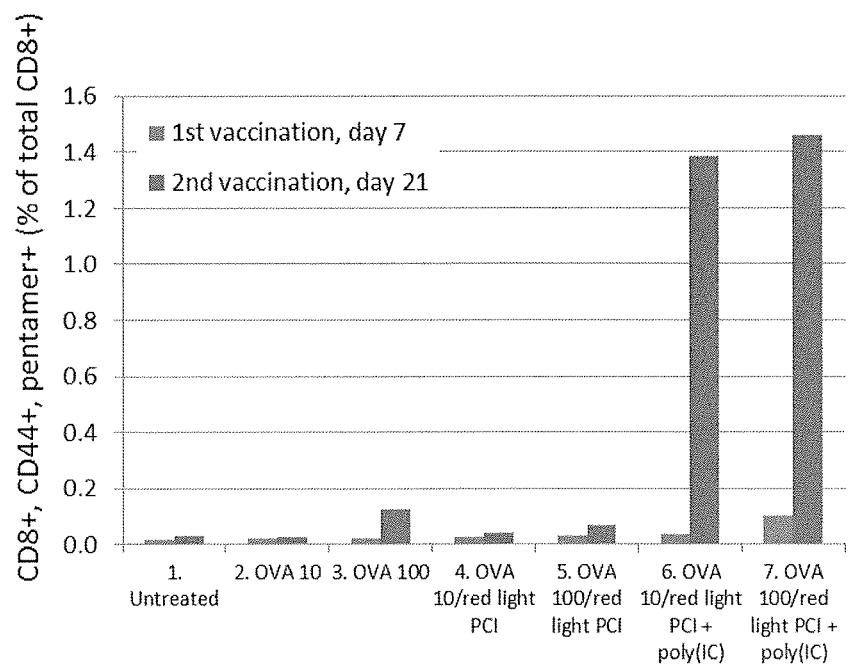
FIG. 9 shows the average values (% antigen-specific, CD44+ cells of the total CD8+ cells) for the experimental groups after the $1^{st}$ and $2^{nd}$ immunisation using red light illumination to activate the photosensitiser.

FIG. 9 shows the average values (% antigen-specific, CD44+ cells of the total CD8+ cells) for the experimental groups after the 1$^{st}$ and 2$^{nd}$ immunisation using red light illumination to activate the photosensitiser. It can be seen that with 10 µg of OVA antigen the combination of poly(IC) and PCI (group 6) was required to achieve an immune response, the antigen alone or combined with PCI (group 4) gave no immunisation effect. With 100 µg of OVA antigen there was a slight effect with the antigen alone (group 3), but the effect with the poly(IC)+PCI combination (group 7) was substantially better.

Example 8: Analysis of PCI with SIINFEKL and Poly(IC) in Normal Mice

The experiment was performed as described above for vaccination of normal mice. The animals were immunised at day 0 and at day 14 with a mixture of 50 µg SIINFEKL peptide (SEQ ID NO:9), 100 µg TPCS$_{2a}$ and 10 µg poly(IC) as specified below. Illumination for 6 min was performed with the LumiSource illumination device, 18 hours after immunisation. Blood samples from day 7 after each immunisation were stained with SIINFEKL pentamer, CD8 and CD44 antibodies, and analysed by flow cytometry as described. The following experimental groups were included:
1. Untreated: Mice were not immunised or illuminated.
2. SIIN 50: Mice were immunised with 50 µg of SIINFEKL peptide (SEQ ID NO:9). They were not illuminated.
3. SIIN 50/PCI: Mice were immunised with a mixture of 50 µg of SIINFEKL peptide (SEQ ID NO:9) and 100 µg TPCS$_{2a}$ and illuminated.
4. SIIN 50/poly(IC): Mice were immunised with a mixture of 100 µg of SIINFEKL peptide (SEQ ID NO:9) and 10 µg poly(IC). They were not illuminated.
5. SIIN 50/poly(IC)/PCI: Mice were immunised with a mixture of 50 µg of SIINFEKL peptide (SEQ ID NO:9), 100 µg TPCS$_{2a}$ and 10 µg of Poly(IC) and illuminated.

Figure 10:
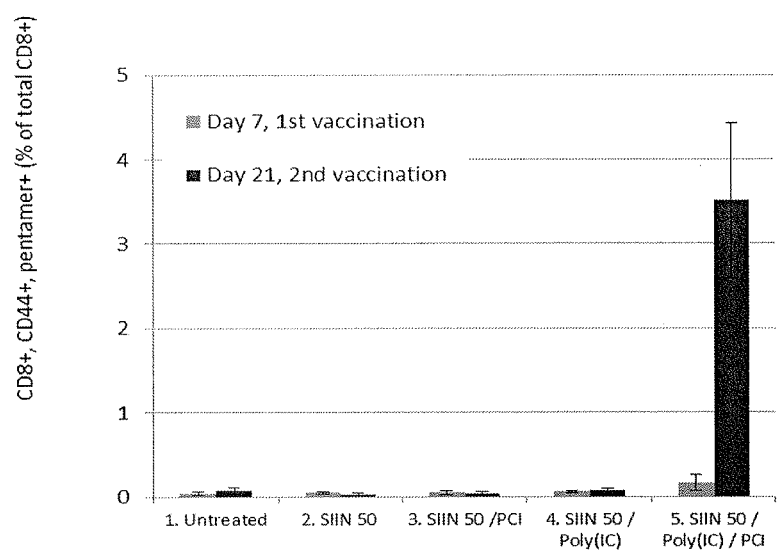
FIG. 10 shows the average values (% antigen-specific, CD44+ cells of the total CD8+ cells) for the experimental groups (error bars are standard error of the mean) after the $1^{st}$ (day 7) and $2^{nd}$ (day 21) immunisation.

FIG. 10 shows the average values (% antigen-specific, CD44+ cells of the total CD8+ cells) for the experimental groups (error bars are standard error of the mean) after the 1$^{st}$ (day 7) and 2$^{nd}$ (day 21) immunisation. It can be seen that the combination of poly(IC) and PCI (group 5) gave a strong immunisation response while no response was seen in any of the other groups. The poly(IC)+PCI combination thus gives a strongly synergistic effect.

Example 9: Analysis of PCI with SIINFEKL and Poly(IC) in Normal Mice

The experiment was performed as described above for vaccination of normal mice. The animals were immunised at day 0 and at day 14 with a mixture of 100 µg SIINFEKL peptide (SEQ ID NO:9), 150 µg $TPCS_{2a}$ and 50 µg poly(IC) (latter only in the $1^{st}$ immunisation) as specified below. Illumination for 6 min was performed with the LumiSource illumination device, 18 hours after immunisation. Blood samples from day 7 after each immunisation were stained with SIINFEKL pentamer, CD8 and CD44 antibodies, and analysed by flow cytometry as described. At day 28 the animals were sacrificed, the spleens were harvested and spleen cells were re-stimulated with SIINFEKL peptide (SEQ ID NO:9) and analysed by ELISA as described under methods. The following experimental groups were included:
1. Untreated: Mice were not immunised or illuminated.
2. 2×SIIN 100: Mice were immunised with 100 µg of SIINFEKL peptide (SEQ ID NO:9) in both immunisations. They were not illuminated.
3. 2×SIIN 100/PCI: Mice were immunised with 100 µg of SIINFEKL peptide (SEQ ID NO:9) and 150 µg $TPCS_{2a}$ in both immunisations, and illuminated.
4. 1×SIIN 100/poly(IC)/1x SIIN 100: Mice were immunised with a mixture of 100 µg of SIINFEKL peptide (SEQ ID NO:9) and 50 µg poly(IC) ($1^{st}$ immunisation); and 100 µg of SIINFEKL peptide (SEQ ID NO:9) ($2^{nd}$ immunisation). They were not illuminated.
5. 1×SIIN 100/poly(IC)/PCI; 1x SIIN 100/PCI: Mice were immunised with a mixture of 100 µg of SIINFEKL peptide (SEQ ID NO:9), 150 µg $TPCS_{2a}$ and 50 µg poly(IC) ($1^{st}$ immunisation); and 100 µg of SIINFEKL peptide (SEQ ID NO:9) and 150 µg $TPCS_{2a}$ ($2^{nd}$ immunisation). They were illuminated in both immunisations.

Figure 11:
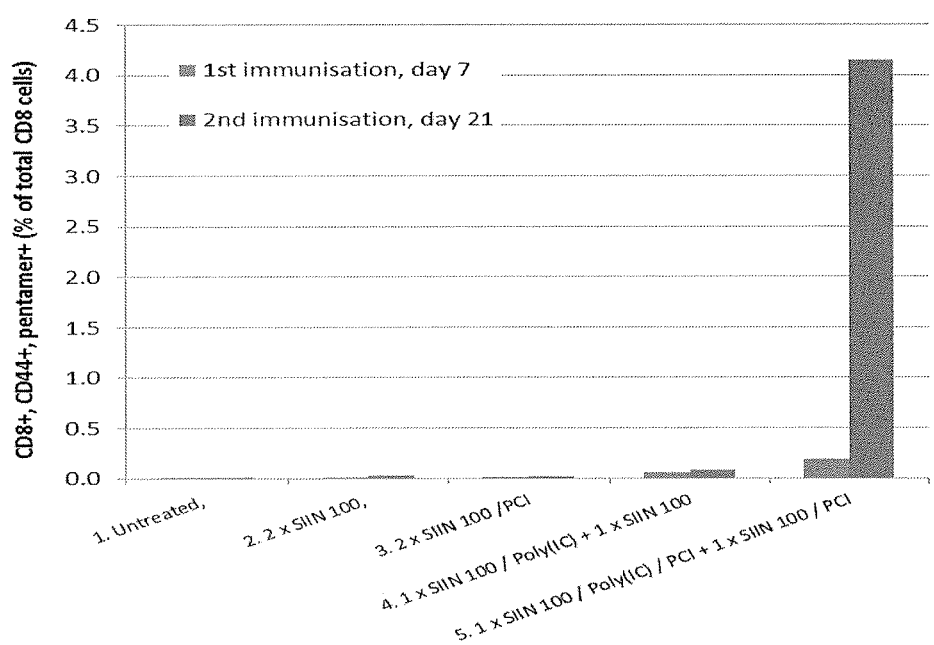
FIG. 11 shows the average values (% antigen-specific, CD44+ cells of the total CD8+ cells) for the experimental groups after the $1^{st}$ (day 7) and $2^{nd}$ (day 21) immunisation.

FIG. 11 shows the average values (% antigen-specific, CD44+ cells of the total CD8+ cells) for the experimental groups after the $1^{st}$ (day 7) and $2^{nd}$ (day 21) immunisation. It can be seen that the combination of poly(IC) and PCI (group 5) gives a very good immune response, even if this combination is used only in the $1^{st}$ immunisation, using only PCI for the $2^{nd}$ immunisation.

Figure 12:
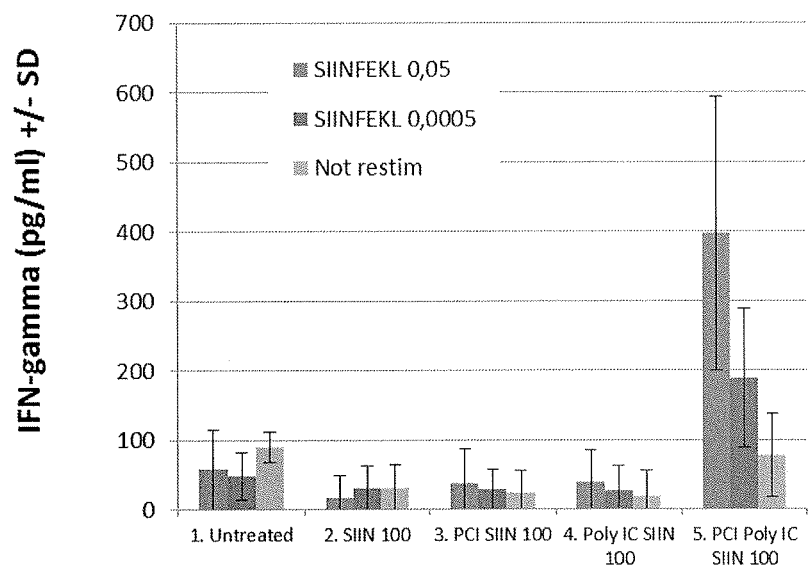
FIG. 12 shows average ELISA values in spleen cells with or without re-stimulation with SIINFEKL peptide (SEQ ID NO:9) as indicated on the figure.

FIG. 12 shows average ELISA values in spleen cells with or without re-stimulation with SIINFEKL peptide (SEQ ID NO:9) as indicated on the figure. It can be seen that while the treatment performed in experimental group 5 ($1^{st}$ immunisation with the combination of PCI and poly(IC); $2^{nd}$ immunisation with PCI only) induced a substantial increase in interferon-gamma production after re-stimulation, this could not be observed in any other of the experimental groups.

Example 10: Analysis of the Effects of MPLA or Imiquimod

The experiment was performed as described above for vaccination of normal mice. The animals were immunised at day 0 and at day 14 with a mixture of 200 µg OVA protein, 100 µg $TPCS_{2a}$ and 50 µg imiquimod or 10 µg MPLA-SM as specified below. Illumination for 6 min was performed with the LumiSource illumination device, 18 hours after immunisation. Blood samples from day 7 after each immunisation were stained by SIINFEKL pentamer, CD8 and CD44 antibodies, and analysed by flow cytometry as described. The following experimental groups were included:
1. Untreated: Mice were not immunised or illuminated.
2. OVA 200: Mice were immunised with 200 µg of OVA. They were not illuminated.
3. OVA 200/PCI: Mice were immunised with a mixture of 200 µg OVA and 100 µg $TPCS_{2a}$ and illuminated.
4. OVA 200/imiquimod: Mice were immunised with a mixture of 200 µg OVA and 50 µg imiquimod. They were not illuminated.
5. OVA 200/imiquimod/PCI: Mice were immunised with a mixture of 200 µg OVA, 100 µg $TPCS_{2a}$ and 50 µg imiquimod, and illuminated.
6. OVA 200/MPLA: Mice were immunised with a mixture of 200 µg OVA and 10 µg MPLA-SM. They were not illuminated.
7. OVA 200/MPLA/PCI: Mice were immunised with a mixture of 200 µg OVA, 100 µg $TPCS_{2a}$ and 10 µg MPLA-SM, and illuminated.

Figure 13:
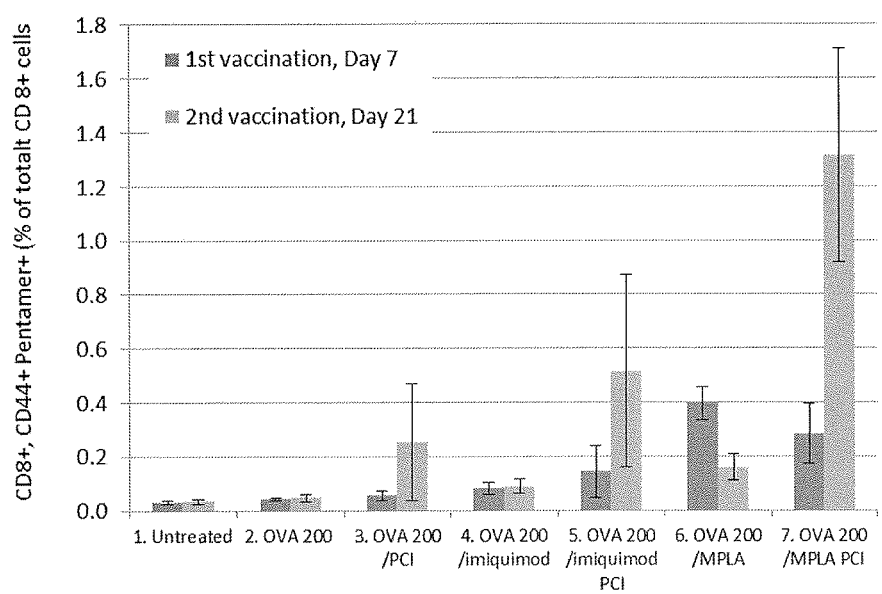
FIG. 13 shows the average values (% antigen-specific, CD44+ cells of the total CD8+ cells) for the experimental groups (5 animals in each group, error bars are standard deviation) after the $1^{st}$ and $2^{nd}$ immunisation.

FIG. 13 shows the average values (% antigen-specific, CD44+ cells of the total CD8+ cells) for the experimental groups (5 animals in each group, error bars are standard deviation) after the $1^{st}$ and $2^{nd}$ immunisation. It can be seen that when using OVA protein as the antigen both for the imiquimod (group 5) and for the MPLA adjuvants (group 7) the combination with PCI induced a substantially better immunisation effect than what was achieved using the adjuvants alone (groups 4 and 6, respectively).

Example 11: PCI with SIINFEKL and Poly(IC) in Normal Mice, Memory Response after $3^{rd}$ Immunisation The experiment was performed as described for vaccination of normal mice under Materials and Methods. The animals were immunised at day 0 and at day 14 with a mixture of 50 µg SIINFEKL peptide (SEQ ID NO:9), 100 µg $TPCS_{2a}$ and 10 µg poly(IC) as specified below. The generation of immunological memory was tested by a $3^{rd}$ immunisation at day 51 with a poly(IC)+PCI treatment. Illumination for 6 min was performed with the LumiSource illumination device, 18 hours after immunisation. Blood samples from day 8 ($1^{ST}$ immunisation), 7 ($2^{nd}$ immunisation) or 6 ($3^{rd}$ immunisation) after each immunisation were stained with SIINFEKL pentamer, CD8 and CD44 antibodies, and analysed by flow cytometry as described. The following experimental groups were included:
1. Untreated: Mice were not immunised or illuminated.
2. SIIN50 Poly(IC)/Poly(IC)+PCI: In the first two immunisations mice were immunised with 50 µg of SIINFEKL peptide (SEQ ID NO:9) and 10 µg of poly(IC). They were not illuminated. In the $3^{rd}$ immunisation the mice were immunised with 50 µg of SIINFEKL peptide (SEQ ID NO:9), 100 µg of $TPCS_{2a}$ and 10 µg of poly(IC). The mice were illuminated.
3. SIIN50 Poly(IC)+PCI/SIIN 50 PCI: In the first two immunisations mice were immunised with 50 µg of SIINFEKL peptide (SEQ ID NO:9), 100 µg of $TPCS_{2a}$ and 10 µg of poly(IC). In the $3^{rd}$ immunisation the mice were immunised with 50 µg of SIINFEKL peptide (SEQ ID NO:9) and 100 µg of $TPCS_{2a}$. The mice were illuminated in all three immunisations.

Figure 14:
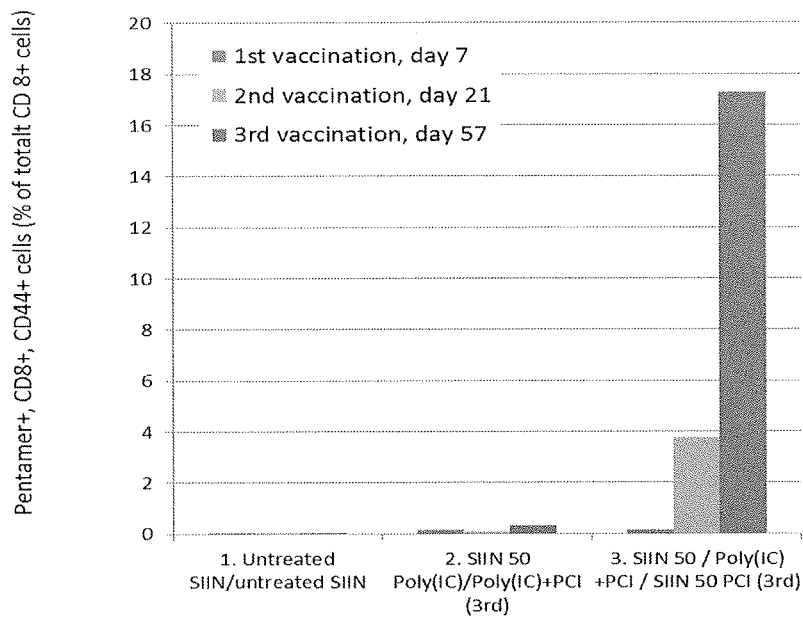
FIG. 14 shows % antigen-specific, CD44+ cells of the total CD8+ cells for the experimental groups after each of the three immunisations.

FIG. 14 shows (% antigen-specific, CD44+ cells of the total CD8+ cells) for the experimental groups after each of the three immunisations. It can be seen that the combination of poly(IC) and PCI induced a very strong immune response, and a significant increase due to the $3^{rd}$ immunisation, even when the $3^{rd}$ immunisation was performed with PCI only (group 3). In contrast when poly(IC) only was used in the first two immunisations there was virtually no immune response, and performing a 3$^{rd}$ immunisation with poly(IC)+PCI did not seem to boost immunisation to any significant degree. Taken together with the results shown in FIG. 11 and FIG. 12 the results indicate that with peptide antigens the combination of poly(IC) and PCI is necessary and sufficient for initiating an immune response, but that this immune response can subsequently be boosted with PCI only. Conversely poly(IC) alone is not able to initiate an immune response, even after two immunisation with poly(IC) and immune response was not observed and trying to boost the response by a third vaccination with poly(IC)+PCI was not successful, indicating the total lack of initiation of an immune response with poly(IC) alone. The data also show that the immune response generated with the poly(IC)+PCI combination is long-lasting since it could be strongly boosted by a 3$^{rd}$ immunisation given 37 days after the 2$^{nd}$ immunisation.

Example 12: Effect of PCI with HPV Peptide Antigen and Poly(IC) in Normal Mice

The experiment was performed as described for vaccination of normal mice under Materials and Methods. The animals were immunised at day 0 and at day 14 with a mixture of 50 µg HPV or SIINFEKL peptide (SEQ ID NO:9) antigens, 100 µg TPCS$_{2a}$ and 10 µg poly(IC) as specified below. The animals were subjected to 3 immunisations at days 7, 14 and 51 as specified below. Illumination for 6 min was performed with the LumiSource illumination device, 18 hours after immunisation. Blood samples from day 8 (1$^{ST}$ immunisation), 7 (2$^{nd}$ immunisation) or 6 (3$^{rd}$ immunisation) after each immunisation were stained with HPV or SIINFEKL pentamer, CD8 and CD44 antibodies, and analysed by flow cytometry as described. The following experimental groups were included:
1. Untreated SIIN: Mice were not immunised or illuminated. Blood samples were stained with SIINFEKL pentamer.
2. Untreated HPV: Mice were not immunised or illuminated. Blood samples were stained with HPV pentamer.
3. SIIN50 Poly(IC)/Poly(IC)+PCI: In the first two immunisations mice were immunised with 50 µg of SIINFEKL peptide (SEQ ID NO:9) and 10 µg of poly(IC). They were not illuminated. In the 3$^{rd}$ immunisation the mice were immunised with 50 µg of SIINFEKL peptide (SEQ ID NO:9), 100 µg of TPCS$_{2a}$ and 10 µg of poly(IC). The mice were illuminated.
4. HPV 50: Mice were immunised with 50 µg of HPV peptide in all three immunisations. The mice were not illuminated.
5. HPV 50/PCI/HPV 50 poly(IC)+PCI (3$^{rd}$): In the first two immunisations mice were immunised with 50 µg of HPV peptide and 100 µg of TPCS$_{2a}$. In the 3$^{rd}$ immunisation the mice were immunised with 50 µg of HPV peptide, 100 µg of TPCS$_{2a}$ and 10 µg of poly(IC). The mice were illuminated in all three immunisations.
6. HPV 50/Poly(IC)/HPV 50 poly(IC)+PCI (3$^{rd}$): In the first two immunisations mice were immunised with 50 µg of HPV peptide and 10 µg of poly(IC). They were not illuminated. In the 3$^{rd}$ immunisation the mice were immunised with 50 µg of HPV peptide, 100 µg of TPCS$_{2a}$ and 10 µg of poly(IC). The mice were illuminated.

Figure 15:
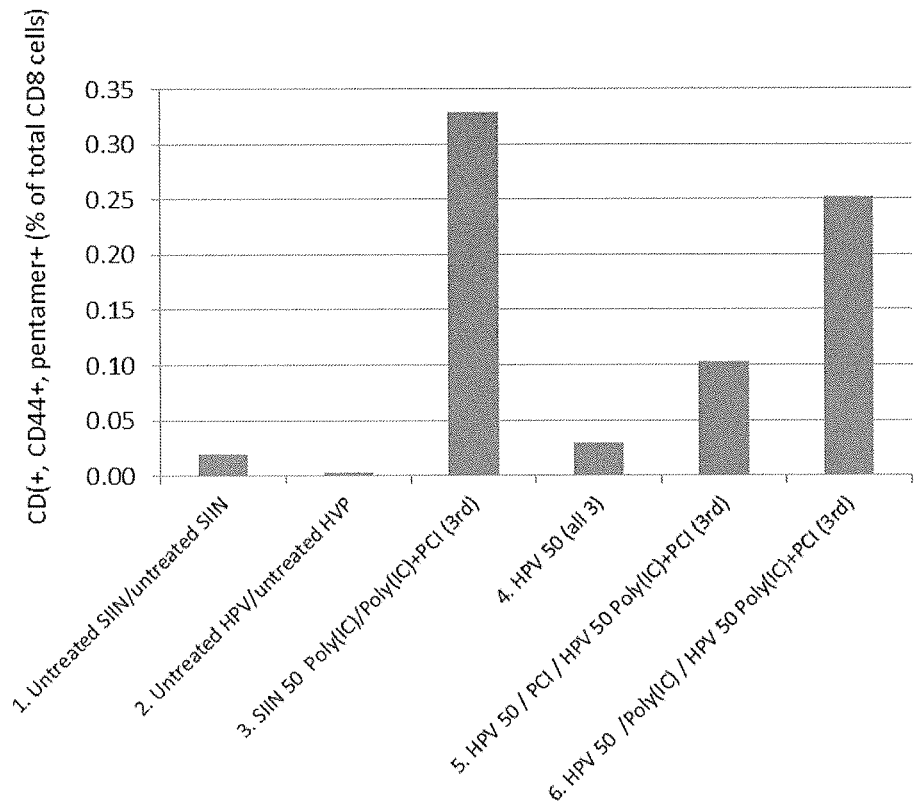
FIG. 15 shows % antigen-specific, CD44+ cells of the total CD8+ cells for the experimental groups after three immunisations.

FIG. 15 shows (% antigen-specific, CD44+ cells of the total CD8+ cells) for the experimental groups after three immunisations. It can be seen that in group 6 an HPV-specific immune response was induced, of about the same magnitude as that achieved with the SIINFEKL peptide (SEQ ID NO:9) with identical immunisation conditions (group 3). This indicates that the combination of PCI and poly(IC) is also efficient in inducing an immune response to the viral and cancer associated HPV E7 antigen, and also the PCI+Poly(IC) induces an immune response to a long peptide antigen (35 amino acids), that probably needs intracellular uptake and proteolytic processing before it can be presented on MHC class I. This is in contrast to the SIINFEKL and the melanoma peptide antigens that may be presented without processing.

Example 13: Effect of Timing of Illumination

The experiment was performed as described above for vaccination of normal mice. The animals were immunised at day 0 and at day 14 with 200 µg OVA protein, 150 µg TPCS$_{2a}$ and 10 µg of poly(IC) as specified below. In all groups TPCS$_{2a}$ was injected 18 h before illumination, while OVA antigen and poly(IC) was either injected 18 h before illumination in a mixture with TPCS$_{2a}$, or 2 h before illumination as a separate injection. Illumination was for 6 min with the LumiSource illumination device. Blood samples from day 7 after each immunisation were stained by SIINFEKL pentamer, CD8 and CD44 antibodies, and analysed by flow cytometry as described. The following experimental groups were included:
1. Untreated: Mice were not immunised or illuminated.
2. OVA 200: Mice were immunised with 200 µg of OVA. They did not receive TPCS$_{2a}$ and were not illuminated.
3. OVA 200 PCI (2 h): Mice were injected with TPCS$_{2a}$ 18 h before illumination and immunised with 200 µg of OVA 2 h before illumination.
4. OVA 200 PCI (18 h): Mice were immunised with TPCS$_{2a}$ and OVA 18 h before illumination.
5. OVA 200 PCI P(IC) (2 h): Mice were injected with TPCS$_{2a}$ 18 h before illumination and immunised with 200 µg of OVA+10 µg Poly(IC) 2 h before illumination.

Figure 16:
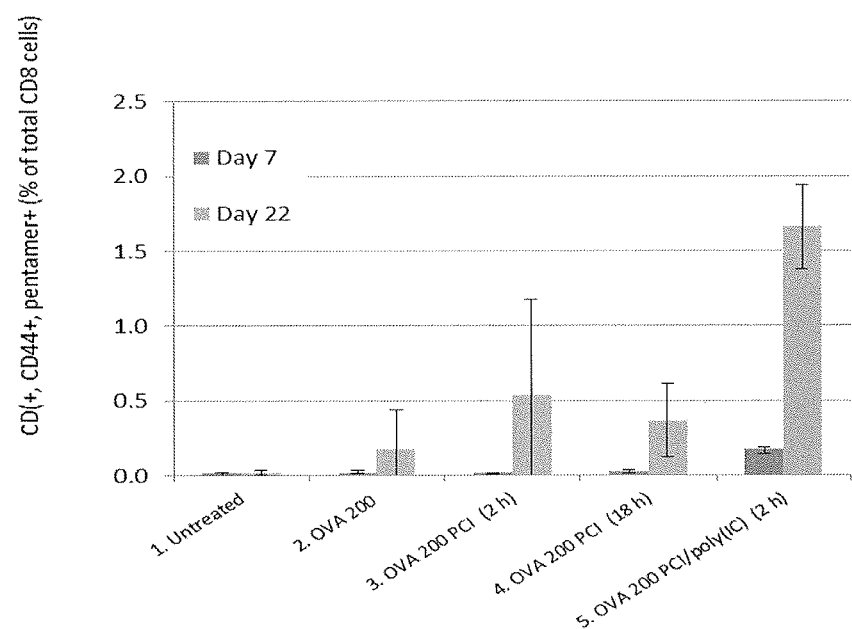
FIG. 16 shows the average values (% antigen-specific, CD44+ cells of the total CD8+ cells) for the experimental groups (5 animals in each group, error bars are standard deviation) after the $1^{st}$ and $2^{nd}$ immunisation.

FIG. 16 shows the average values (% antigen-specific, CD44+ cells of the total CD8+ cells) for the experimental groups (5 animals in each group, error bars are standard deviation) after the 1$^{st}$ and 2$^{nd}$ immunisation. It can be seen that the immune response is enhance by the poly(IC)+PCI combination also when the antigen+poly(IC) is administered only 2 hours before illumination.

Example 14: Effect of PCI with SIINFEKL Peptide and Poly(IC) in Normal Mice

PCI+Poly(IC) as Compared to Poly(IC) with Three Immunisations.

The experiment was performed as described for vaccination of normal mice under Materials and Methods. The animals were immunised at day 0, day 14 and day 42 with a mixture of 50 µg SIINFEKL peptide (SEQ ID NO:9) and 100 µg TPCS$_{2a}$ and 10 µg poly(IC) as specified below. Illumination for 6 min was performed with the LumiSource illumination device, 18 hours after immunisation. Blood samples from day 7 after each immunisation were stained by SIINFEKL pentamer, CD8 and CD44 antibodies, and analysed by flow cytometry as described. The following experimental groups were included:
1. Untreated SIIN: Mice were not immunised or illuminated, blood samples were stained with SIIN pentamer.
2. SIIN/poly(IC): Mice were immunised three times with a mixture of 50 µg SIINFEKL peptide (SEQ ID NO:9) and 10 µg poly(IC). They were not illuminated.

3. SIIN/poly(IC)/PCI: Mice were immunised with a mixture of 50 µg SIINFEKL peptide (SEQ ID NO:9), 100 µg TPCS$_{2a}$ and 10 µg poly(IC) and illuminated.

Figure 17:
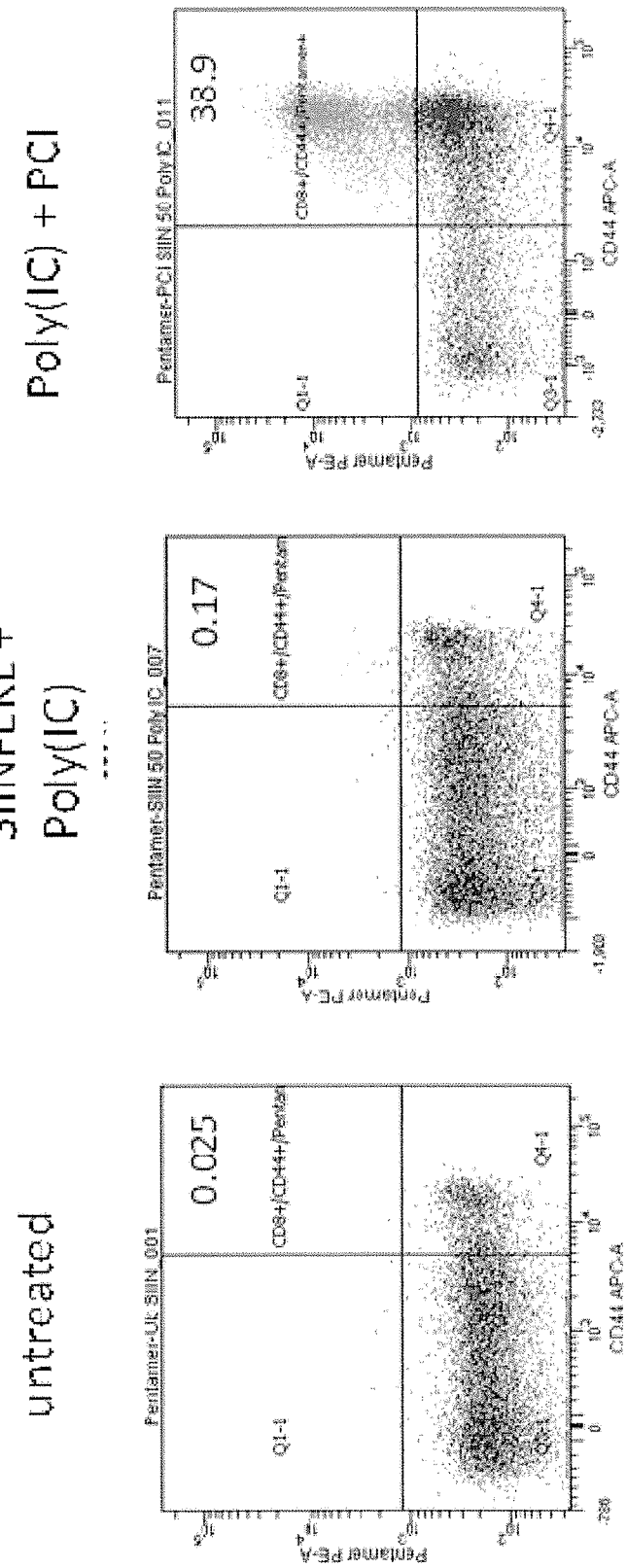
FIG. 17 shows a flow cytometry dot plot after the $3^{rd}$ immunisation from a typical animal in the three experimental groups.

FIG. 17 shows a flow cytometry dot plot after the 3$^{rd}$ immunisation from a typical animal in the three experimental groups clearly showing the very strong response induced by the poly(IC)+PCI combination.

Figure 18:
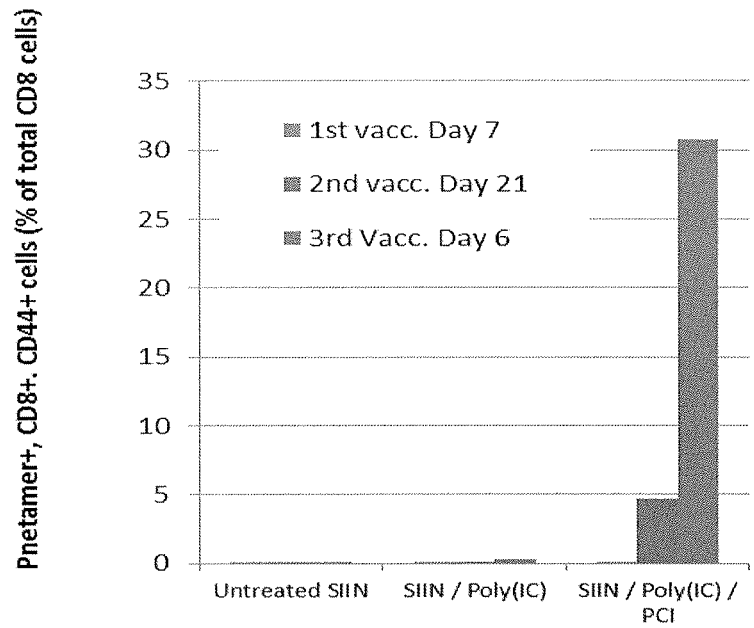
FIG. 18 shows the average values (% antigen-specific, CD44+ cells of the total CD8+ cells) after each of the 3 immunisations.

FIG. 18 shows the average values (% antigen-specific, CD44+ cells of the total CD8+ cells) after each of the 3 immunisations. It can be seen that the PCI+Poly(IC) combination induced a very strong immune response resulting in about 30% of antigen specific CD8 T-cells in the blood samples after the 3$^{rd}$ immunisation. In comparison 3 immunisations with antigen and the poly(IC) adjuvant alone had only a very minor effect (0.28% positive cells after 3$^{rd}$ immunisation).

Example 15: Effect of PCI with HPV Long Peptide Antigen and Poly(IC) in Normal Mice The experiment was performed as described above for vaccination of normal mice.

The HPV 16 E7 sequence GQAEPDRAHYNIVTFCCK-CDSTLRLCVQSTHVDIR (SEQ ID NO:1) was used as the "long" peptide antigen. The animals were immunised at day 0 and at day 14 with a mixture of 50 µg HPV long peptide antigen, 100 µg TPCS$_{2a}$ and 10 µg poly(IC) (p(IC) as specified below). The animals were subjected to 2 immunisations at days 7 and 14 as specified below. Illumination for 6 min was performed with the LumiSource illumination device, 18 hours after immunisation. Blood samples from day 6 after each immunisation were stained with HPV pentamer, CD8 and CD44 antibodies, and analysed by flow cytometry as described. The following experimental groups were included:

1. 2×HPV: Mice were immunised 2 times with 50 µg HPV long peptide. The mice were not illuminated
2. 2×HPV+p(IC): Mice were immunised 2 times with a mixture of 50 µg HPV long peptide and 10 µg poly(IC). The mice were not illuminated.
3. 2×HPV+p(IC)+PCI: Mice were immunised 2 times with a mixture of 50 µg HPV long peptide, 10 µg poly(IC) and 100 µg TPCS$_{2a}$. The mice were illuminated at both immunisations.
4. 1: HPV+p(IC)+PCI. 2: HPV+PCI: Mice were immunised with a mixture of 50 µg HPV long peptide, 10 µg poly(IC) and 100 µg TPCS$_{2a}$ (1$^{st}$ immunisation), and 50 µg HPV long peptide and 100 µg TPCS$_{2a}$ (2$^{nd}$ immunisation). The mice were illuminated at both immunisations.
5. 1: HPV+PCI. 2: HPV+p(IC)+PCI: Mice were immunised with a mixture of 50 µg HPV long peptide and 100 µg TPCS$_{2a}$ (1$^{st}$ immunisation), and 50 µg HPV long peptide, 10 µg poly(IC) and 100 µg TPCS$_{2a}$ (2nd immunisation). The mice were illuminated at both immunisations.

Figure 19:
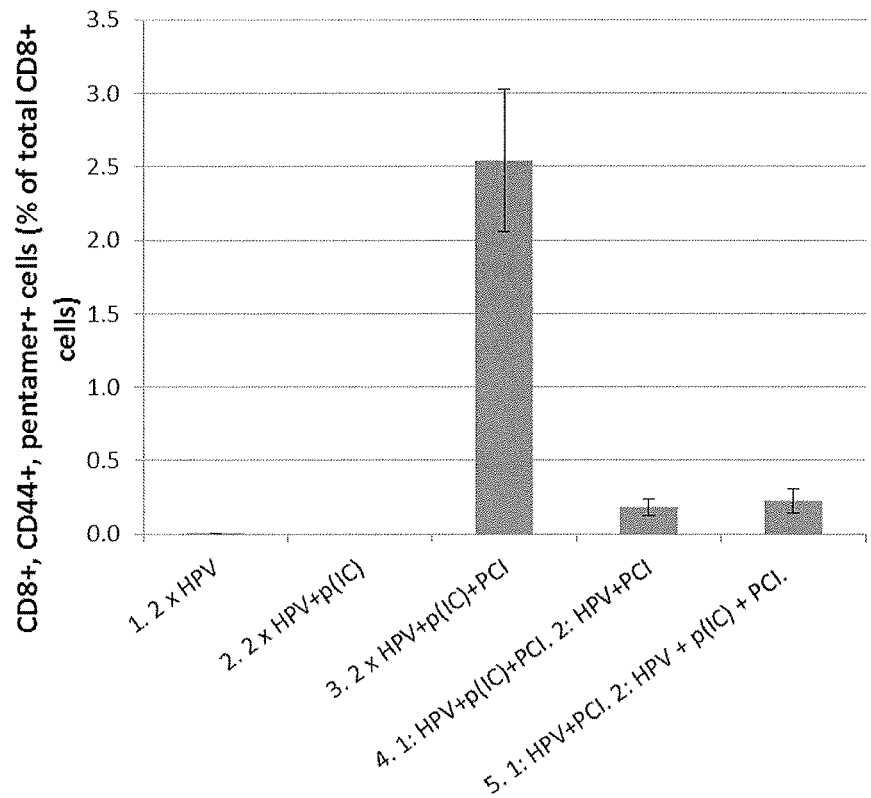
FIG. 19 shows % antigen-specific, CD44+ cells of the total CD8+ cells for the experimental groups after two immunisations.

FIG. 19 shows (% antigen-specific, CD44+ cells of the total CD8+ cells) for the experimental groups after two immunisations. It can be seen that in group 3 (2 immunisations with the PCI+p(IC) combination) a strong HPV-specific immune response was induced, while in groups 4 and 5 (one immunisation with PCI+p(IC) combination, one with only PCI) a weaker, but still significant immune response was observed, as compared to the experimental groups where PCI were not employed (groups 1 and 2). This shows that the combination of PCI and poly(IC) is efficient in inducing an immune response to the viral and cancer associated HPV E7 antigen, and that two immunisations with this combination is more effective that one such immunisation combined with one immunisation with only PCI. It also shows that with the HPV long peptide antigen the p(IC) adjuvant has no effect when used without the combination with PCI.

Example 16: Effect of PCI with HPV Short Peptide Antigen and Poly(IC) in Normal Mice The experiment was performed as described above for vaccination of normal mice. The HPV 16 E7 CD8 epitope RAHYNIVTF (SEQ ID NO:2) was used as the "short" peptide antigen. The animals were immunised at day 0 and at day 13 with a mixture of 50 µg HPV short peptide antigen, 100 µg TPCS$_{2a}$ and 10 µg poly(IC) (p(IC) as specified below). The animals were subjected to 2 immunisations at days 7 and 13 as specified below. Illumination for 6 min was performed with the LumiSource illumination device, 18 hours after immunisation. Blood samples from day 6 after each immunisation were stained with HPV pentamer, CD8 and CD44 antibodies, and analysed by flow cytometry as described. The following experimental groups were included:

1. Untreated. The mice were not immunised or illuminated.
2. 2×HPV short: Mice were immunised 2 times with 50 µg HPV short peptide. The mice were not illuminated
3. 2×HPV short+p(IC): Mice were immunised 2 times with a mixture of 50 µg HPV short peptide and 10 µg poly(IC). The mice were not illuminated.
4. 2×HPV short+PCI: Mice were immunised 2 times with a mixture of 50 µg HPV short peptide, 10 µg poly(IC) and 100 µg TPCS$_{2a}$. The mice were illuminated at both immunisations.
5. 2×HPV short+p(IC)+PCI: Mice were immunised 2 times with a mixture of 50 µg HPV short peptide, 10 µg poly(IC) and 100 µg TPCS$_{2a}$. The mice were illuminated at both immunisations.
6. 1: HPV short+p(IC)+PCI. 2: HPV short+PCI: Mice were immunised with a mixture of 50 µg HPV short peptide, 10 µg poly(IC) and 100 µg TPCS$_{2a}$ (1$^{st}$ immunisation), and 50 µg HPV short peptide and 100 µg TPCS$_{2a}$ (2$^{nd}$ immunisation). The mice were illuminated at both immunisations.

Figure 20:
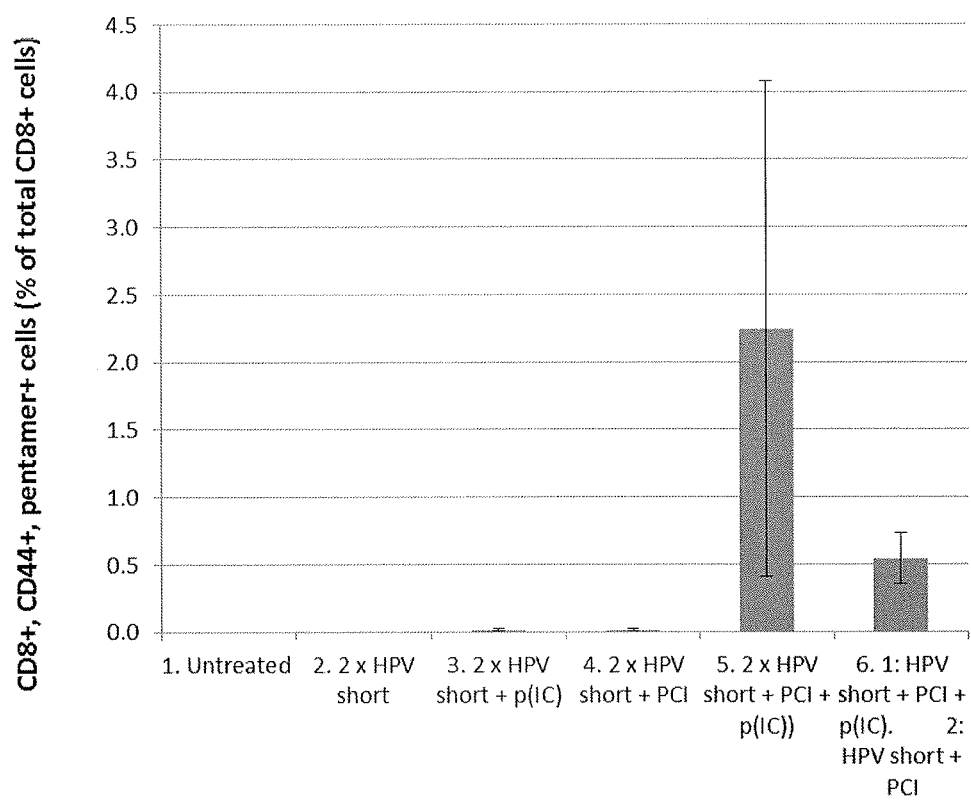
FIG. 20 shows % antigen-specific, CD44+ cells of the total CD8+ cells+/− SEM for the experimental groups after two immunisations.
Figure 21:
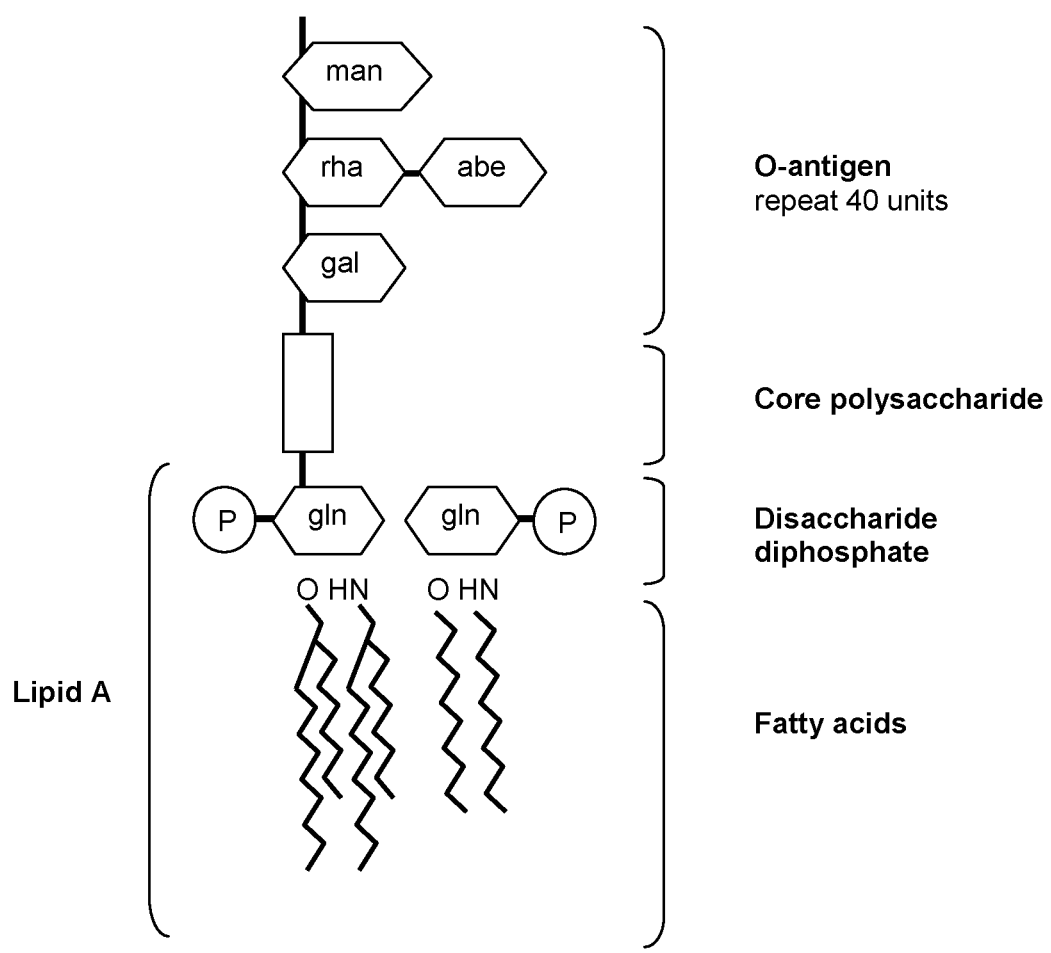
FIG. 21 shows the structure of a lipopolysaccharide.

FIG. 20 shows (% antigen-specific, CD44+ cells of the total CD8+ cells+/−SEM) for the experimental groups after two immunisations. It can be seen that in both groups (5 and 6) immunised with the p(IC)+PCI combination a significant immune response was induced, the better effect being achieved in group 5 where this combination was employed for both immunisations. In comparison in the groups where only p(IC) or only PCI were used for both immunisations no immune response was observed (compared to untreated animals (group 1) and animals immunised with the antigen only (group 2)). This shows that the combination of PCI and poly(IC) is efficient in inducing an immune response to the viral and cancer associated HPV E7 antigen also when this is delivered as a short peptide, and that two immunisations with the p(IC)+PCI combination gives a strong synergistic effect as compared to p(IC) alone or PCI alone.

The invention claimed is:

1. A method of expressing an antigenic molecule or a part thereof on the surface of a living cell, comprising conducting photochemical internalisation (PCI) by contacting a cell with an antigenic molecule, a photosensitizing agent, and a TLR ligand such that said antigenic molecule and said photosensitising agent and optionally said TLR ligand are each taken up into an intracellular vesicle in said cell, and irradiating the cell with light of a wavelength effective to activate the photosensitising agent under conditions where viability of the cell is maintained, wherein said antigenic molecule is released into the cytosol of the cell and the antigenic molecule or a part thereof is subsequently presented on the surface of the cell which has been irradiated;

wherein when said method is performed in vivo said antigenic molecule, photosensitising agent and TLR ligand are administered to the subject on which the method is performed; wherein said antigenic molecule, photosensitising agent and TLR ligand are separate molecules; and wherein said TLR ligand is not siRNA.

2. The method of claim 1, wherein said TLR ligand is selected from the group consisting of a TLR1 ligand, a TLR2 ligand, a TLR5 ligand, a TLR6 ligand, a TLR8 ligand, a TLR11 ligand, a TLR12 ligand and a TLR13 ligand.

3. The method of claim 1, wherein said TLR ligand is a TLR3 ligand.

4. The method of claim 1, wherein said TLR ligand is a TLR4 ligand.

5. The method of claim 1, wherein said TLR ligand is a TLR7 ligand.

6. The method of claim 1, wherein said TLR ligand is a TLR9 ligand.

7. The method of claim 1, wherein:
(a) the antigenic molecule is a molecule capable of stimulating an immune response;
(b) the antigenic molecule is a peptide;
(c) the antigenic presentation results in the stimulation of an immune response; and/or
(d) the photosensitising agent is selected from $TPCS_{2a}$, $AlPcS_{2a}$, $TPPS_4$ and $TPBS_{2a}$.

8. The method of claim 1, wherein the method is performed in vivo, in vitro or ex vivo.

9. The method of claim 1, wherein the cell is an antigen presenting cell, and/or wherein said cell is contacted with said antigenic molecule, photosensitising agent and TLR ligand simultaneously, separately or sequentially.

10. The method of claim 3, wherein said TLR3 ligand is a double-stranded RNA molecule.

11. The method of claim 10, wherein said double-stranded RNA molecule is poly(I:C).

12. The method of claim 7, wherein said molecule capable of stimulating an immune response is a vaccine antigen or vaccine component.

13. The method of claim 7, wherein said peptide is a melanoma peptide or human papillomavirus (HPV) peptide.

14. The method of claim 7, wherein said photosensitising agent is $TPCS_{2a}$.

15. The method of claim 9, wherein said antigen presenting cell is a dendritic cell.

16. The method of claim 7, wherein said peptide is a melanoma peptide.

17. The method of claim 16, wherein said TLR ligand is poly(I:C).

18. The method of claim 1, wherein the photosensitising agent is administered by intradermal administration.

19. The method of claim 4, wherein said TLR4 ligand is Monophosphoryl Lipid A (MPLA).

20. The method of claim 5, wherein said TLR7 ligand is:
(i) an imidazoquinoline compound of formula (1)

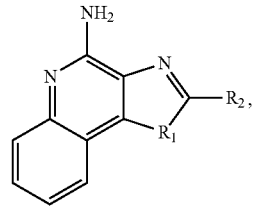

(1)

wherein
$R_1$ is an amino-alkyl group having the formula $N-CH_2-C(CH_3)_2-R_3$;
$R_2$ is a hydrogen atom or an alkyl group interrupted with an oxygen or nitrogen group having the formula $-CH_2-X-CH_2CH_3$, wherein X is O or NH; and
$R_3$ is OH or a hydrogen atom;
or a pharmaceutically acceptable salt thereof; or
(ii) a single stranded RNA molecule.

21. The method of claim 20, wherein said imidazoquinoline compound is selected from resiquimod, imiquimod and gardiquimod or a pharmaceutically acceptable salt thereof, or wherein said single stranded RNA molecule is ssPolyU.

22. The method of claim 6, wherein said TLR9 ligand is a CpG oligonucleotide, which is a single-stranded oligonucleotide of from 6-50 bases which includes at least one CpG motif and at least one base flanking said motif on each of the 3' and 5' sides.

23. The method of claim 22, wherein said CpG oligonucleotide contains a palindromic sequence 8 to 16 bases in length or has the sequence: 5'-tcgtcgttttcggcgcgcgccg-3' (SEQ ID NO:4) or 5'-tccatgacgttcctgacgtt-3 (SEQ ID NO:3).

* * * * *